US012678270B2

(12) United States Patent
Zegarelli et al.

(10) Patent No.: US 12,678,270 B2
(45) Date of Patent: Jul. 14, 2026

(54) ORAL APPLIANCE FOR TREATING INFLAMED TISSUE OF THE ORAL CAVITY USING THE TOP-DOWN METHOD

(71) Applicant: Emanate Biomedical, Inc., New York, NY (US)

(72) Inventors: Peter John Zegarelli, Sleepy Hollow, NY (US); Jarret Scott Fass, New York, NY (US)

(73) Assignee: Emanate Biomedical, Inc., Larchmont, NY (US)

( * ) Notice: Subject to any disclaimer, the term of this patent is extended or adjusted under 35 U.S.C. 154(b) by 0 days.

(21) Appl. No.: 17/775,085

(22) PCT Filed: Nov. 6, 2020

(86) PCT No.: PCT/US2020/059440
§ 371 (c)(1),
(2) Date: May 6, 2022

(87) PCT Pub. No.: WO2021/092405
PCT Pub. Date: May 14, 2021

(65) Prior Publication Data
US 2022/0395361 A1 Dec. 15, 2022

Related U.S. Application Data

(60) Provisional application No. 62/933,083, filed on Nov. 8, 2019.

(51) Int. Cl.
*A61K 31/155* (2006.01)
*A61C 19/06* (2006.01)

(52) U.S. Cl.
CPC .......... *A61C 19/063* (2013.01); *A61K 31/155* (2013.01)

(58) Field of Classification Search
CPC ........................... A61C 19/063; A61K 31/155
See application file for complete search history.

(56) References Cited

U.S. PATENT DOCUMENTS 6,966,773 B2 * 11/2005 Keller ........................ A61P 1/02
                                                    433/80
7,878,801 B2 2/2011 Abolfathi et al.
(Continued)

OTHER PUBLICATIONS

International Search Report and Written Opinion of the International Searching Authority (ISA/US) mailed on Mar. 22, 2021 in International PCT Application No. PCT/US2020/059440 filed Nov. 6, 2020.

*Primary Examiner* — Edward Moran
*Assistant Examiner* — Luis Ruiz Martin
(74) *Attorney, Agent, or Firm* — Sorell, Lenna & Schmidt, LLP

(57) ABSTRACT

An oral appliance for delivering a medicament to an inflamed tissue inside an oral cavity is provided. The oral appliance has an interior surface configured to contour at least a portion of teeth and/or soft tissue areas inside the oral cavity, the interior surface of the oral appliance having a medicament disposed at a discrete region of the interior surface of the oral appliance, the medicament configured to contact a top portion of the inflamed tissue inside the oral cavity when the oral appliance is worn to cause delivery of the medicament to at least the top portion of the inflamed tissue. A method of making the oral appliance and a method of treating an inflamed tissue inside an oral cavity using the oral appliance is also provided.

17 Claims, 18 Drawing Sheets

(56) References Cited

U.S. PATENT DOCUMENTS

| | | | |
|---|---|---|---|
| 8,075,309 B2 | 12/2011 | Li et al. | |
| 8,113,837 B2 | 2/2012 | Zegarelli | |
| 9,089,388 B2 | 7/2015 | Zegarelli | |
| 2008/0255498 A1* | 10/2008 | Houle | A61C 17/0208 |
| | | | 604/20 |
| 2014/0011162 A1* | 1/2014 | Zegarelli | A61K 9/0053 |
| | | | 433/215 |
| 2015/0306007 A1 | 10/2015 | Golas et al. | |
| 2016/0022379 A1* | 1/2016 | Keller | A61C 19/063 |
| | | | 433/136 |
| 2020/0060797 A1* | 2/2020 | Sachdeva | G16H 50/20 |
| 2020/0129421 A1* | 4/2020 | Feng | A61F 5/566 |

* cited by examiner

STAGES OF GUM DISEASE AND POCKET DEPTHS

HEALTHY GUMS
1MM - 3MM

MILD PERIODONTITIS
3MM - 5MM

MODERATE PERIODONTITIS
5MM - 7MM

SEVERE PERIODONTITIS
7MM AND ABOVE

STAGES OF TARGETED MEDICAMENT TREATMENT WITH ORAL APPLIANCE

HEALTHY GUMS
1MM - 3MM

MILD PERIODONTITIS
3MM - 5MM

MODERATE PERIODONTITIS
5MM - 7MM

SEVERE PERIODONTITIS
7MM AND ABOVE

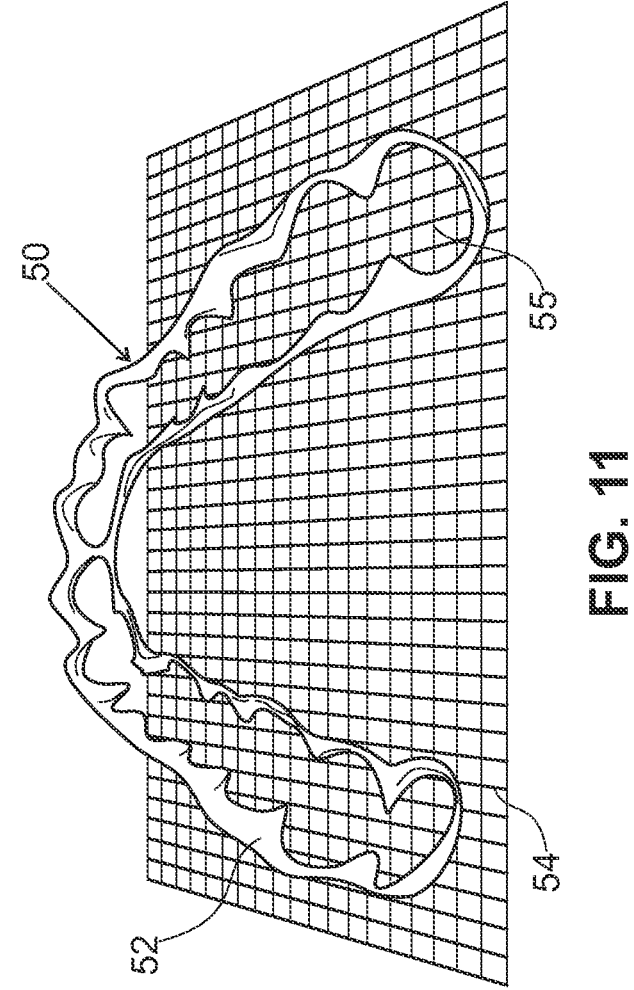
FIG. 11
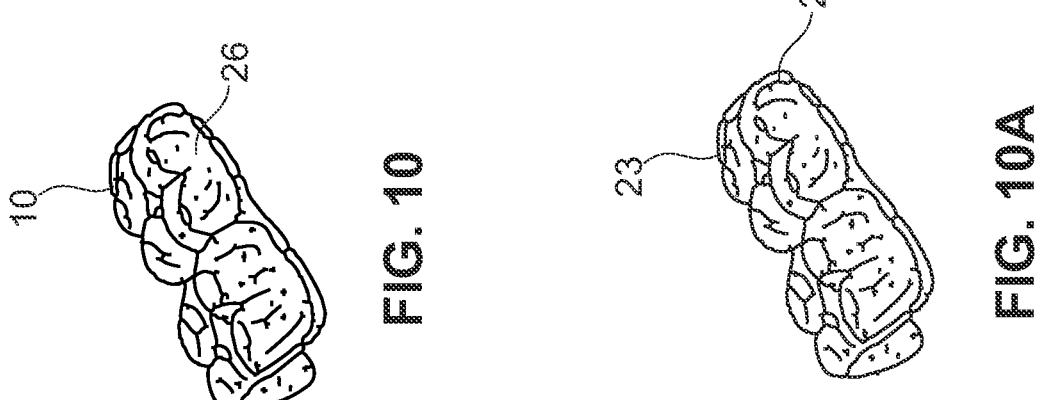
FIG. 10
FIG. 10A

ORAL APPLIANCE FOR TREATING INFLAMED TISSUE OF THE ORAL CAVITY USING THE TOP-DOWN METHOD

BACKGROUND

The present disclosure is related generally to the field of oral appliances for delivering a medicament to an inflamed or normal tissue of the oral cavity.

Dental plaque is a precursor of calculus. Dental calculus, or tartar, refers to a build-up of hardened (mineralized) plaque on the teeth, formed by the presence of saliva, debris, and minerals. Mature calculus consists of an inorganic portion which is largely calcium phosphate arranged in a hydroxyapatite crystal lattice structure similar to bone, enamel, and dentin. An organic portion is also present and consists of desquamated epithelial cells, leukocytes, salivary sediment, food debris, and various types of microorganisms. Its rough surface provides an ideal medium for bacterial growth, threatening the health of the gums and absorbing unaesthetic stains due to its porous nature far more easily than natural teeth.

Dental plaque can occur above (supragingival) and below (subgingival) the gumline. Supragingival dental plaque forms on teeth within hours after they are cleaned. In the presence of a diet rich in carbohydrates, shifts occur in the supragingival plaque to more of an acidogenic plaque, with dental caries as an outcome. Plaques that form on subgingival tooth surfaces and coat the epithelium lining of the gingival crevice lead to the development of gingival and periodontal infections (i.e., gingivitis and periodontitis, respectively).

In gingivitis, the gums become red, swollen and can bleed easily during tooth brushing. In this form of gum disease, the teeth are still firmly planted in their sockets. When left untreated, gingivitis can progress to periodontitis. In periodontitis, the inner layer of the gum pulls away from the teeth and forms pockets, which are spaces that become inflamed and infected. Bacterial toxins produced by the bacteria in plaque together with the body's natural responses to infections start to break down the bone and the connective tissue that hold the teeth in place. As the disease progresses, the tissue that supports the teeth, the bones and gums are destroyed and the teeth are no longer anchored in place, they become loose and tooth loss may ultimately occur.

Periodontal (gum) disease affects a majority of adults at some time in their lives. Periodontal disease is a chronic inflammatory condition of the gingiva (gums), the teeth and the attachment apparatus which connects the teeth to the gums and the bone. It starts out benignly enough as gingivitis. Often times, gingivitis is reversible with dental cleanings and proper oral hygiene. It is a surface condition and can be treated by surface instruments such as toothbrushes and floss. However, if left untreated, gingivitis will progress to periodontal disease (e.g., periodontitis), which will result in the breakdown of periodontal ligament that attaches the gums to the teeth, thus creating the periodontal pocket. It is the host response to the invading bacteria which breaks down the soft and hard (bone) tissues through the release of antibodies, polymorphonuclear cells (PMNs), cytokines and other inflammatory factors which end up feeding the invading bacteria. The bacteria, in response to the deepening pocket, also alter their microbiome population from an initial one of primarily aerobes at the surface to mixture of aerobes and anaerobes. The anaerobes begin to dominate the deeper the pocket gets away from the surface oxygen. The dysbiosis, characterized by a shift in microflora, perpetuates in a positive feedback loop. The red complex bacteria associated with periodontal disease are inflammophilic, which means they feed off the host's immune response. Treatment of periodontal disease falls into two broad categories: surgical (to restore supportive tissues) and non-surgical (to control bacterial growth). Traditionally, there have been two categories of non-surgical treatment for periodontal disease: personal home care and invasive services provided by dental professionals. Dental professionals often will do a cleaning to remove plaque and tartar from above and below the gumline, and a more deep-cleaning scaling and root planing. Sometimes, though not often, a chemical adjunct will be inserted into the periodontal pocket. Home care practices are divided into two categories: mechanical and chemical.

At-home mechanical tools for the control of oral bacteria include toothbrushes (manual and electric), floss, Waterpiks, toothpicks and rubber tips, and other teeth cleaning devices. These all require a certain level of dexterity and the ability to properly use the devices. At-home chemical treatments for the control of oral bacteria include antimicrobials (e.g., antiseptics and antibiotics). The most commonly used antimicrobials are in toothpastes, oral rinses, or other teeth cleaning devices. They have been used to apply medicaments topically to the soft tissues and teeth by the patient. Some crossover devices use a syringe-like tip to irrigate a solution about the gums. Tooth brushing is recommended to be done at least twice a day and the other procedures once a day.

Dental professionals provide invasive mechanical services such as curettage and scaling and root planing (SRP). Using miniature sickle-like instruments (curettes and scalers), the sulcus and pockets about the teeth are instrumented such that chronically inflamed tissue is surgically debrided from the base of the pocket up to the top portion of the pocket and removed. This chronically inflamed tissue is then discarded. Additionally, the roots of the teeth are scraped and scaled of any adherent foreign material such as for example, bacteria (e.g., plaque) and calculus (also known as tartar, which is calcified plaque), which can tenaciously adhere to the tooth. Rough spots on the tooth root are made smooth to provide a clean surface for the gums to reattach to the teeth.

Periodontal surgery is also done in severe cases using scalpel blades, periosteal elevators and other instruments, as well as electro-surgery and lasers to treat various periodontal conditions.

More recently, dental professionals have also used chemical means to treat periodontal disease such as Arestin®, which contains minocycline microspheres, and PerioChip®, which is a biodegradable chip containing chlorhexidine, along with other treatments that are invasively placed by either a syringe or by insertion under the gum line down to the base of the periodontal pocket. SRP is recommended to be done at least twice/year, more frequently for many patients with periodontal disease, in a routine periodontal maintenance therapy program (RPMT), and the chemical insertions are performed on an as-needed basis.

For both the home and office procedures, there are basically two treatment areas; surface treatments done at home and invasive ones done at the dental professional office. Patients with periodontal pockets cannot access pockets that are deeper than about 3 mm on their own. Therefore, in order to treat the infection patients with periodontitis seek treatment at the dental office. However, the surface therapies at home are primarily at the top portion of the pocket surface and stay at the top while the dental professional therapies seek to treat the disease from the base of the pocket and work their way from the bottom, up.

These mechanical and chemical procedures are based on the premise that in order to treat periodontal disease, one must start at the base of the pocket. In other words, in order to change the entire microbiome above that deepest point, the deep periodontal pocket must be accessed directly. Therefore, to summarize, periodontal disease starts at the top of the sulcus and works its way down to an ever-deepening pocket. Current treatment modalities are either surface in nature (only reaching the first 1-3 mm of free gingiva) or attack the base of the pocket.

It would therefore be desirable to provide an oral appliance that is configured to deliver a medicament in the same fashion that the inflammatory disease first progressed from the top, down the periodontal pocket and since it is a chronic inflammatory disease to treat it in a chronic sustained fashion from the top portion of the inflamed tissue and then downward, which would progressively reduce or eliminate the inflammation. This type of oral appliance would be beneficial in treating periodontal disease in a medical fashion just as other chronic inflammatory diseases, such as rheumatoid arthritis, are treated in a sustained fashion.

SUMMARY

New oral appliances are provided that can target the delivery of medicament to the top portion of the inflamed tissue (e.g., inflamed gums, gum line, teeth, etc.) within the oral cavity and then target the treatment down the inflamed tissue. This type of oral appliance is beneficial in treating periodontal disease (e.g., periodontitis). In some embodiments, the oral appliance allows treatment of the inflammatory tissue at once and constantly in a sustained fashion.

In some embodiments, the treatment provided in this application targets the gingival margin of the teeth for delivery of the medicament because periodontal disease (e.g., periodontitis) starts and, if left untreated, continues and is perpetuated at the gingival margin. The top down treatment provided by the oral appliances described in this application targets the gingival margin of the teeth on an ongoing basis until inflammation is reduced or the diseased periodontal pockets shrink to at least below about 3 mm or the gums shrink back to their normal, healed state size and become pink and firm. In some embodiments, one goal of treatment is to gradually reduce the dysbiosis of the oral microbiome over time which will manifest in both a reduction of inflammation and depending on each individual's rate of response to the treatment, a gradual reduction in pocket depth with the intention to get it to less than 4 mm depth.

In some embodiments, there is an oral appliance for delivering a medicament to an inflamed tissue inside an oral cavity, the oral appliance having an interior surface configured to contour at least a portion of teeth and/or soft tissue areas inside the oral cavity, the interior surface of the oral appliance having a medicament disposed at a discrete region of the interior surface of the oral appliance, the medicament configured to contact the top portion of the inflamed tissue inside the oral cavity when the oral appliance is worn to cause delivery of the medicament to at least the top portion of the inflamed tissue.

In some embodiments, there is a system for delivering a medicament to an inflamed tissue inside an oral cavity, the system comprising a first set of oral appliances, each of the first set of oral appliances having an interior surface configured to contour at least a portion of the teeth and/or soft tissue areas inside the oral cavity, the interior surface of each of the first set of oral appliances having a medicament disposed at a discrete region of the interior surface of each of the first set of oral appliances, the medicament configured to contact the top portion of the inflamed tissue inside the oral cavity when the oral appliance is worn to cause delivery of the medicament to at least the top portion of the inflamed tissue; and a second set of oral appliances, each of the second set of oral appliances having an interior surface configured to contour at least the portion of teeth and/or soft tissue areas inside the oral cavity, the interior surface of each of the second set of oral appliances having a medicament disposed at a discrete region of the interior surface of each of the second set of oral appliances, the medicament configured to contact the middle or mid-level portion of the inflamed tissue inside the oral cavity when the oral appliance is worn to cause delivery of the medicament to at least the middle or mid-level portion of the inflamed tissue.

In some embodiments, there is an oral appliance for delivering a probiotic to a tissue inside an oral cavity, the oral appliance having an interior surface configured to contour at least a portion of teeth and/or soft tissue areas inside the oral cavity, the interior surface of the oral appliance having a probiotic disposed at a discrete region of the interior surface of the oral appliance, the probiotic configured to contact tissue inside the oral cavity when the oral appliance is worn to cause delivery of the probiotic to the tissue.

In some embodiments, there is a method of making an oral appliance for delivering a medicament to an inflamed tissue inside an oral cavity, the method comprising providing an oral appliance having an interior surface configured to contour at least a portion of teeth and/or soft tissue areas inside the oral cavity, and disposing a medicament at a discrete region of the interior surface of the oral appliance, the medicament configured to contact the top portion of the inflamed tissue inside the oral cavity when the oral appliance is worn to cause delivery of the medicament to at least the top portion of the inflamed tissue.

In some embodiments, there is a computer implemented method of making an oral appliance for delivering a medicament to an inflamed tissue inside an oral cavity, the method comprising creating a digital record of a patient's oral cavity by obtaining a baseline digital image of at least a portion of the patient's teeth, and/or soft tissue of the patient's oral cavity using an imaging device; obtaining a first digital image (Dig1) of the oral appliance based on the baseline digital image corresponding to the at least a portion of the patient's teeth, and/or soft tissue of the patient's oral cavity of the baseline image, creating a second digital image (Dig2) by performing a digital segmentation defining at least one treatment surface area including a discrete region of the oral cavity including a top portion of inflamed tissue, the second digital image corresponding to at least a portion of the patient's teeth and/or soft tissue of the patient's oral cavity including the top portion of inflamed tissue; combining the first digital image and the second digital image to form a third digital image (Dig3) of the oral appliance, the oral appliance having an interior surface configured to contour at least a portion of teeth and/or soft tissue areas inside the oral cavity, the interior surface of the oral appliance having a medicament disposed at a discrete region of the interior surface of the oral appliance, the medicament configured to contact the top portion of the inflamed tissue inside the oral cavity when the oral appliance is worn to cause delivery of the medicament to at least the top portion of the inflamed tissue; storing the third digital image in the computer; and instructing the computer to produce the oral appliance by any method currently available such as analog—thermoforming, hybrid analog/digital, 3D printed, injection molded or other methods.

In some embodiments, there is a method of treating an inflamed tissue inside an oral cavity, the method comprising providing an oral appliance for delivering a medicament to an inflamed tissue inside an oral cavity, the oral appliance having an interior surface configured to contour at least a portion of teeth and/or soft tissue areas inside the oral cavity, the interior surface of the oral appliance having a medicament disposed at a discrete region of the interior surface of the oral appliance, the medicament configured to contact the top portion of the inflamed tissue inside the oral cavity when the oral appliance is worn to cause delivery of the medicament to at least the top portion of the inflamed tissue.

In some embodiments, there is an oral appliance for delivering a medicament to an inflamed tissue of an oral cavity, the oral appliance having an interior surface configured to contour at least a portion of teeth and/or soft tissue areas of the oral cavity including the subgingival space, the interior surface of the oral appliance having a medicament disposed at a discrete region of the interior surface of the oral appliance, the medicament configured to contact at least a portion of the subgingival space of the inflamed tissue of the oral cavity when the oral appliance is worn and cause delivery of the medicament to at least the inflamed tissue.

In some embodiments, there is a system for delivering a medicament to an inflamed tissue of an oral cavity, the system comprising a first set of oral appliances, each of the first set of oral appliances having an interior surface configured to contour at least a portion of the teeth and/or soft tissue areas of the oral cavity including the subgingival space, the interior surface of each of the first set of oral appliances having a medicament disposed at a discrete region of the interior surface of each of the first set of oral appliances, the medicament configured to contact at least a first portion of the inflamed tissue of the oral cavity including at least a first portion of the subgingival space when the oral appliance is worn to cause delivery of the medicament to at least the first portion of the subgingival space of the inflamed tissue; and a second set of oral appliances, each of the second set of oral appliances having an interior surface configured to contour at least the portion of teeth and/or soft tissue areas of the oral cavity, the interior surface of each of the second set of oral appliances having a medicament disposed at a discrete region of the interior surface of each of the second set of oral appliances, the medicament configured to contact at least a second portion of the inflamed tissue of the oral cavity including at least a second portion of the subgingival space when the oral appliance is worn to cause delivery of the medicament to at least the second portion of the subgingival space of the inflamed tissue.

In some embodiments, there is a method of making an oral appliance for delivering a medicament to an inflamed tissue of an oral cavity including at least a portion of the subgingival space, the method comprising providing an oral appliance having an interior surface configured to contour at least a portion of teeth and/or soft tissue areas inside the oral cavity including at least the portion of the subgingival space, and disposing a medicament at a discrete region of the interior surface of the oral appliance, the medicament configured to contact at least the portion of the subgingival space of the inflamed tissue inside the oral cavity when the oral appliance is worn to cause delivery of the medicament to at least the portion of the subgingival space of the inflamed tissue.

In some embodiments, there is a computer implemented method of making an oral appliance for delivering a medicament to an inflamed tissue of an oral cavity including at least a portion of the subgingival space, the method comprising creating a digital record of a patient's oral cavity by obtaining a baseline digital image of at least a portion of the patient's teeth, and/or soft tissue of the patient's oral cavity using an imaging device; obtaining a first digital image (Dig1) of the oral appliance based on the baseline digital image corresponding to the at least a portion of the patient's teeth, and/or soft tissue of the patient's oral cavity of the baseline image, creating a second digital image (Dig2) by performing a digital segmentation defining at least one treatment surface area including a discrete region of the oral cavity including at least a portion of the subgingival space of inflamed tissue, the second digital image corresponding to at least a portion of the patient's teeth and/or soft tissue of the patient's oral cavity including at least the portion of the subgingival space of inflamed tissue; combining the first digital image and the second digital image to form a third digital image (Dig3) of the oral appliance, the oral appliance having an interior surface configured to contour at least a portion of teeth and/or soft tissue areas of the oral cavity, the interior surface of the oral appliance having a medicament disposed at a discrete region of the interior surface of the oral appliance, the medicament configured to contact at least the portion of the subgingival space of the inflamed tissue of the oral cavity when the oral appliance is worn to cause delivery of the medicament to at least the portion of the subgingival space of the inflamed tissue; storing the third digital image in the computer; and instructing the computer to produce the oral appliance.

In some embodiments, there is a method of treating an inflamed tissue of an oral cavity, the method comprising providing an oral appliance for delivering a medicament to an inflamed tissue of an oral cavity including at least a portion of a subgingival space, the oral appliance having an interior surface configured to contour at least a portion of teeth and/or soft tissue areas of the oral cavity, the interior surface of the oral appliance having a medicament disposed at a discrete region of the interior surface of the oral appliance, the medicament configured to contact at least the portion of the subgingival space of the inflamed tissue of the oral cavity when the oral appliance is worn to cause delivery of the medicament to at least the portion of the subgingival space of the inflamed tissue.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings.

FIG. 10 is a perspective view of a pre-formed sheet of material forming an oral appliance containing a medicament wherein the oral appliance is contoured to fit at least a portion of teeth and/or soft tissue inside the oral cavity. This oral appliance is designed to treat with medicament discrete regions of two teeth and gums surrounding those two teeth.

FIG. 10A is a perspective view of a pre-formed sheet of material forming an oral appliance containing a medicament wherein the oral appliance is contoured to fit at least a portion of teeth and/or soft tissue inside the oral cavity wherein the oral appliance includes an antibiotic and a probiotic.

FIG. 11 illustrates an embodiment of a virtual image (Dig2) of the regions along the sulcus (gumline) where the medicament of the oral appliance will be loaded in a polymer gel material. The medicament is disposed at discrete or continuous regions throughout the polymer gel material and corresponds to the regions that will require treatment. FIG. 11 is a representation of segmenting out the gumline from the Base Image.

As the medicament is leached out of the hydrogel, empty hydrogel spaces open up and become available to absorb and remove crevicular/sulcular fluids from the environment. In this way, the hydrogel has dual ability to deliver medicament and wicking action to remove crevicular/sulcular fluids from the environment. This dual action of wicking, which then creates a negative crevicular fluid flow, allows the medicaments under pressure to enter the top portion of the pocket to fill the resultant negative pressure void, thus inserting the medicaments further into the periodontal pockets. Over sustained daily treatment regimens, the inflammation at the top portion of the pocket decreases and with decreased inflammation there is decreased swelling and therefore decreased pocket depth as well as decreased gingival crevicular flow.

In some embodiments, the oral appliance is disposable because once the medicament completely diffuses out of the hydrogel, the hydrogel then fills up with the crevicular/sulcular fluids, which need to be disposed. The medicament is now into the periodontal pockets that are now open due to the absorption void created by the departure of crevicular/sulcular fluid. This process is repeated every day and over time each periodontal pocket begins to shrink at the top. The inflamed tissue over time gradually shrinks and the outward flow of crevicular/sulcular fluids emanating from the periodontal pockets also decreases because of decreased inflammation. This improved pressure cycling further allows deeper penetration of the medicaments into ever greater depths of the pocket in a gradual top-down approach.

Figure 14:
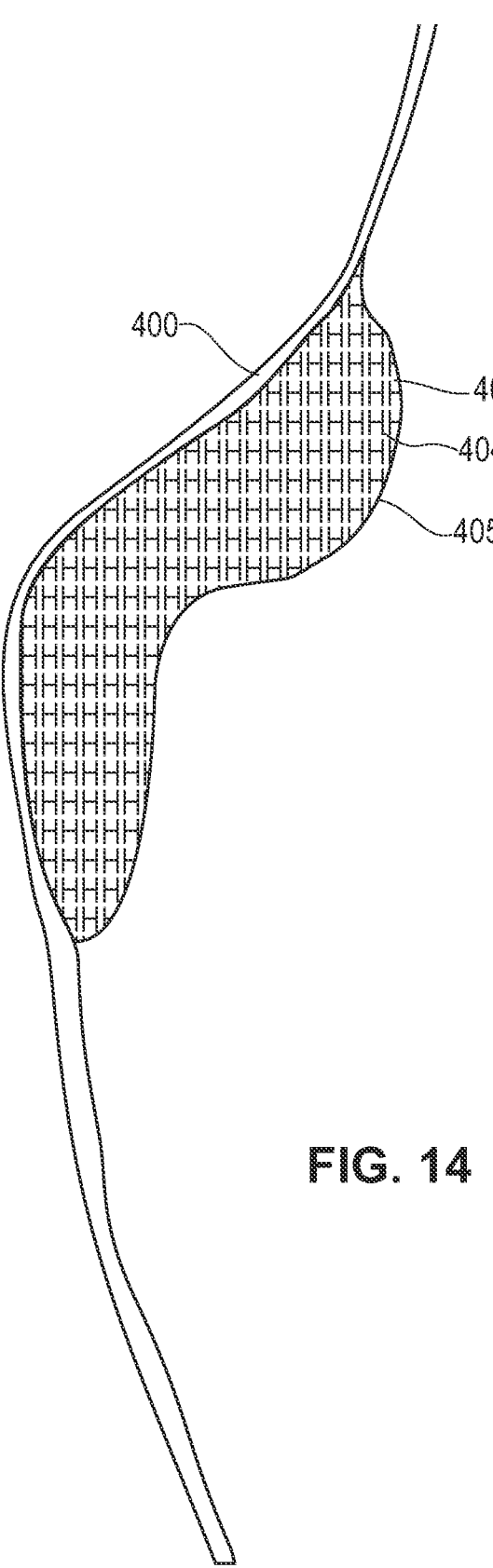

FIG. 14 illustrates an enlarged cross-sectional view of a portion of the oral appliance. In the embodiment shown, medicament is disposed in a porous material that is a hydrogel at a discrete region of the oral appliance. The hydrogel is shown in an uncompressed state and when worn with slight pressure, the hydrogel will be compressed against, among other things, the gingival crevice or periodontal pocket causing a seal or encapsulation of the entrance of the gingival crevice or periodontal pocket, which prevents oral fluids (e.g., saliva, exudate or other captured fluids upon insertion of the device, etc.) from entering the crevice or pocket, which allows release of the medicament in the gingival crevice or periodontal pocket and allows the hydrogel to absorb or wick fluid from the crevice or pocket.

Figure 15:
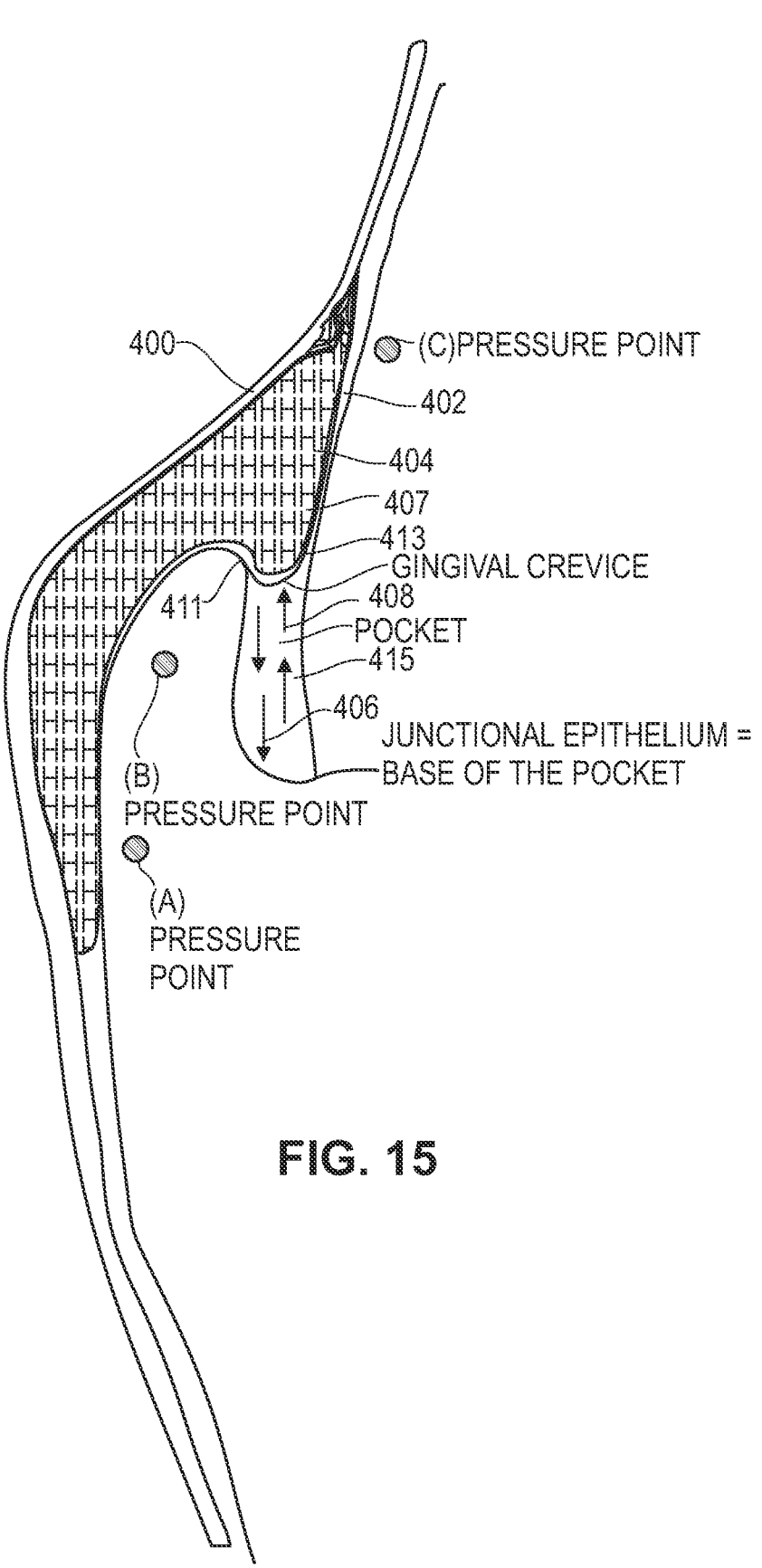

FIG. 15 illustrates an enlarged cross-sectional view of a portion of the oral appliance that is placed adjacent to the teeth and gums. In the embodiment shown, medicament is disposed in a porous material that is a hydrogel at a discrete region of the oral appliance. The hydrogel is shown in a compressed state, where the device is worn and the hydrogel is compressed against, among other things, the gingival crevice or periodontal pocket causing a seal or encapsulation of the entrance of the gingival crevice or periodontal pocket, which prevents oral fluids (e.g., saliva, exudate, or other captured fluids upon insertion of the device, etc.) from entering the crevice or pocket. The hydrogel allows release of the medicament into the gingival crevice or periodontal pocket to treat the inflamed tissue shown by the down arrows. The hydrogel also absorbs or wicks oral fluids from the crevice or pocket, which aids healing, shown by the up arrows.

Figure 15A:
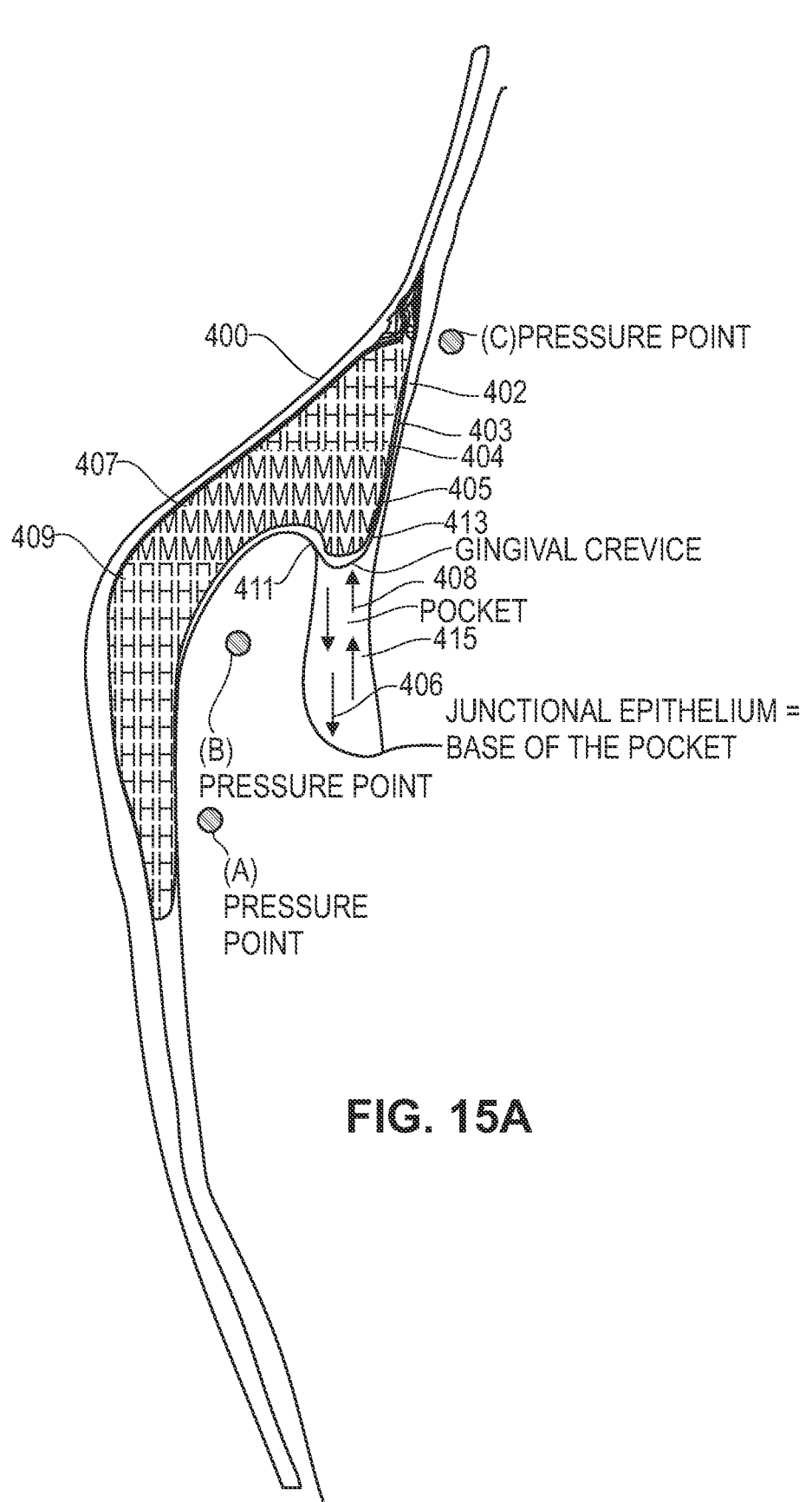

FIG. 15A illustrates an enlarged cross-sectional view of a portion of the oral appliance that is placed adjacent to the teeth and gums. In the embodiment shown, medicament is disposed in a porous material that is a hydrogel at a discrete region of the oral appliance. The hydrogel with slight pressure when the device is worn is in a compressed state, where the hydrogel is compressed against, among other things, the gingival crevice or periodontal pocket causing medicament to be released into the gingival crevice or periodontal pocket to treat the inflamed tissue shown by the down arrows. The hydrogel also seals the entrance of the gingival crevice or periodontal pocket, which prevents oral fluids (e.g., saliva, exudate or other captured fluids upon insertion of the device, etc.) from entering the crevice or pocket. The hydrogel also absorbs or wicks oral fluids from the crevice or pocket, which aides healing as the medicament is released from the hydrogel. The hydrogel is shown with an upper surface and a lower surface away from the entrance to the periodontal pocket which also transfers medicament out and absorbs captured fluids along the tooth surface on the upper aspect of the drawing alike wise transfers medicament out and absorbs external saliva which leeches under the device from the edges in at the lower portion of the drawing which allows more captured fluids and external saliva oral fluids to be absorbed by the hydrogel thus creating a barrier (H areas) to contamination and dilution of the middle surface (M areas) of the hydrogel that will thus have a higher concentration of medicament where it is needed at the entrance to the periodontal pocket than the upper and lower surfaces of the hydrogel which sacrifice their medicaments in order to protect the concentration in the middle.

Figure 15B:
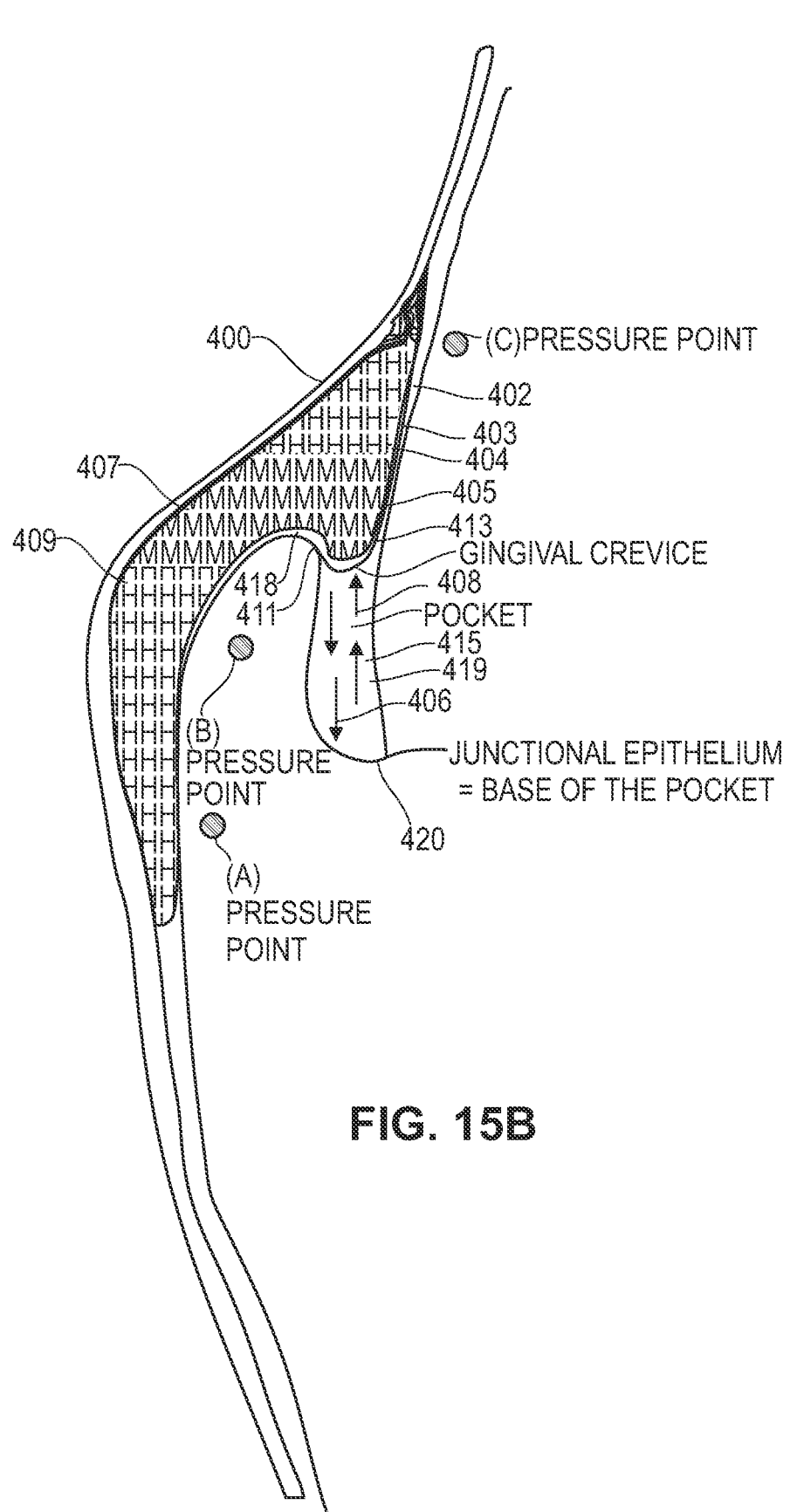

FIG. 15B illustrates an enlarged cross-sectional view of a portion of an oral appliance that is placed adjacent to the teeth and gums with respect to the top, middle and bottom portions of the periodontal pocket being treated.

Figure 16:
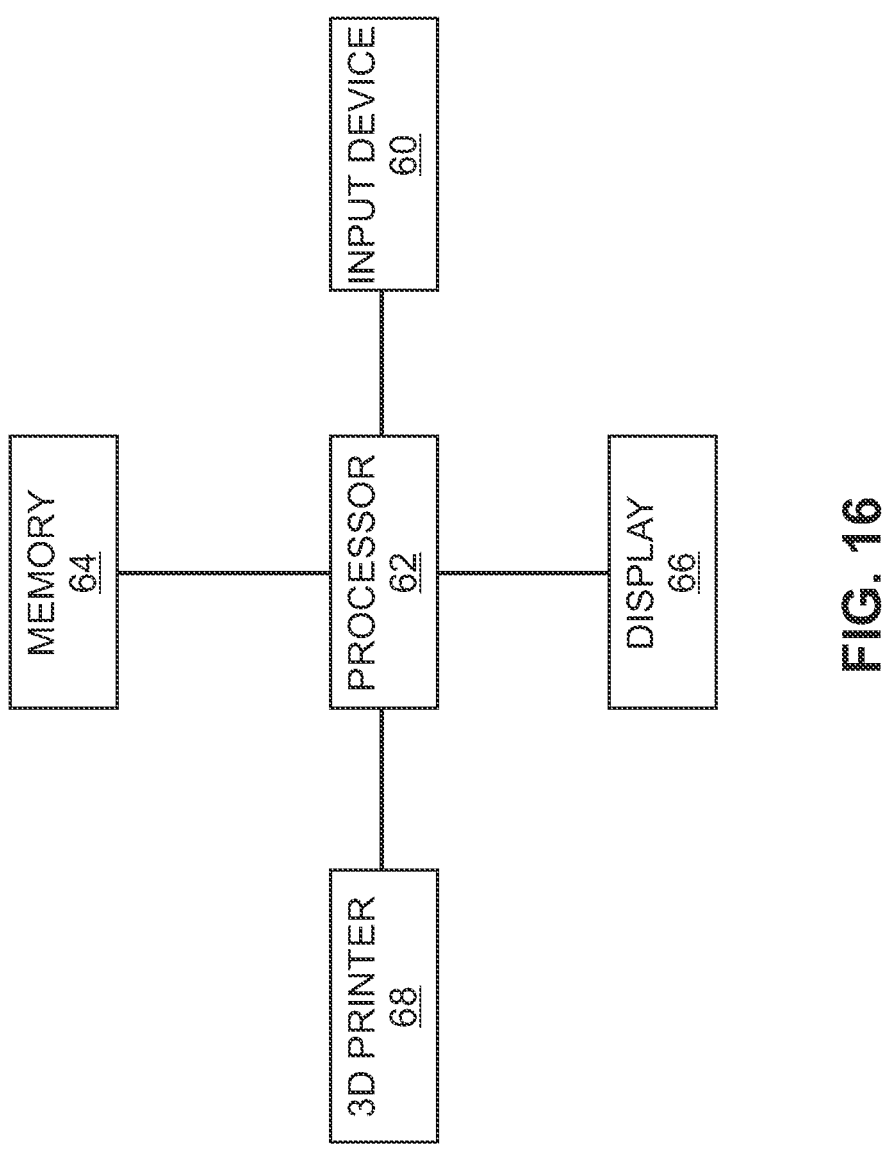

FIG. 16 illustrates an embodiment of the computer-implemented system for producing a pre-loaded oral appliance.

Figure 16A:
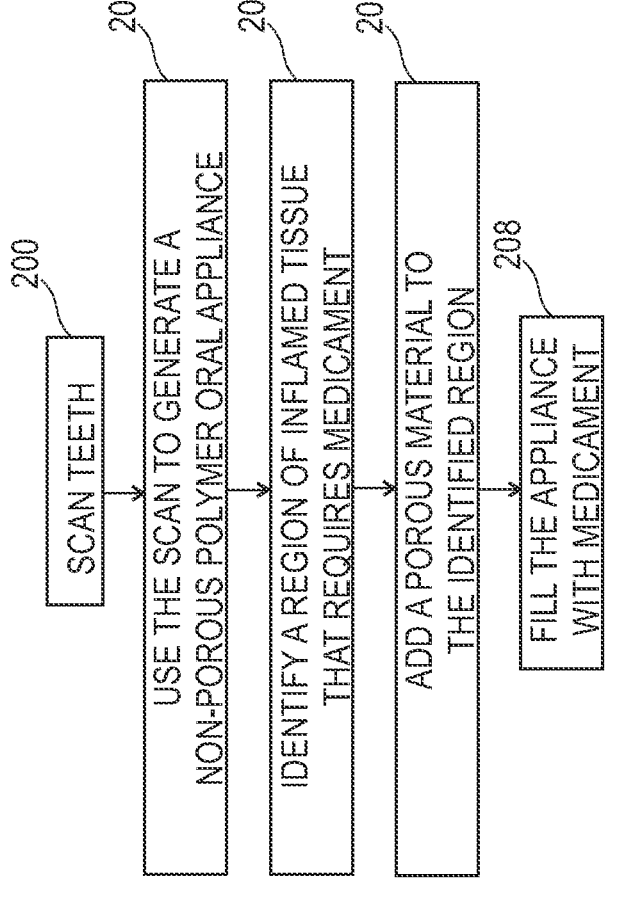

FIG. 16A is a flow chart illustrating one embodiment of the computer-implemented system and steps that the computer performs to produce a non-porous polymer oral appliance. The oral appliance also comprises discrete regions made from a porous material that is filled with the medicament.

Figure 17:
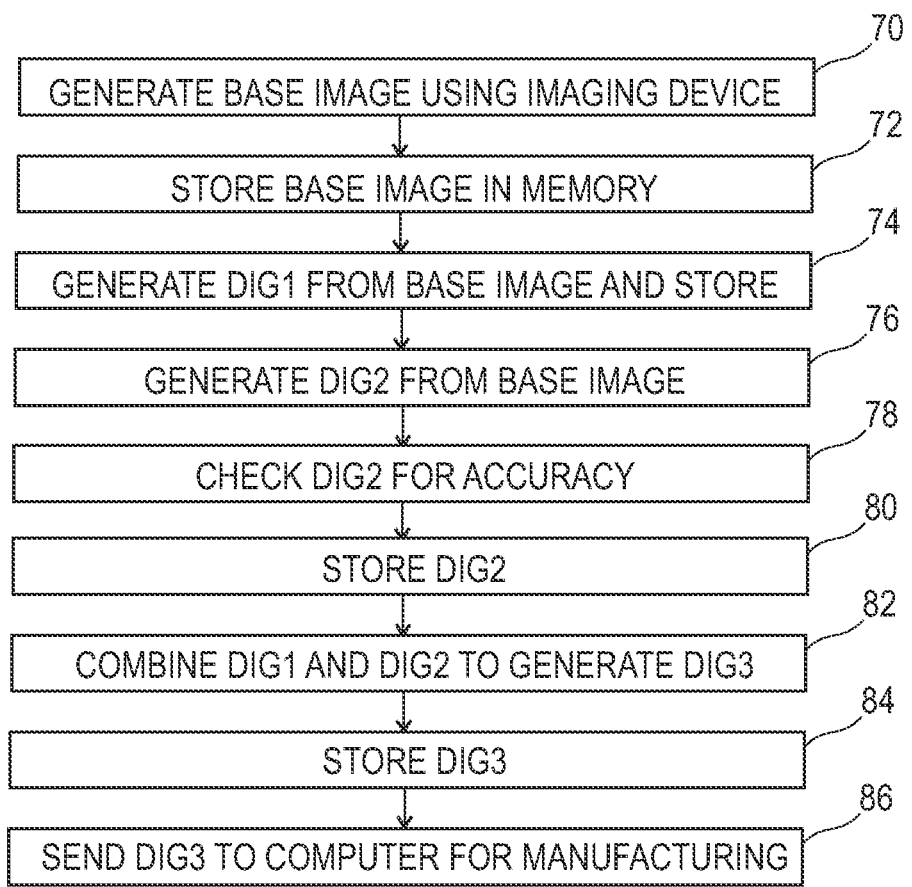

FIG. 17 is a flow chart illustrating an embodiment of the computer-implemented system for producing an oral appliance pre-loaded with medicament.

Figure 18:
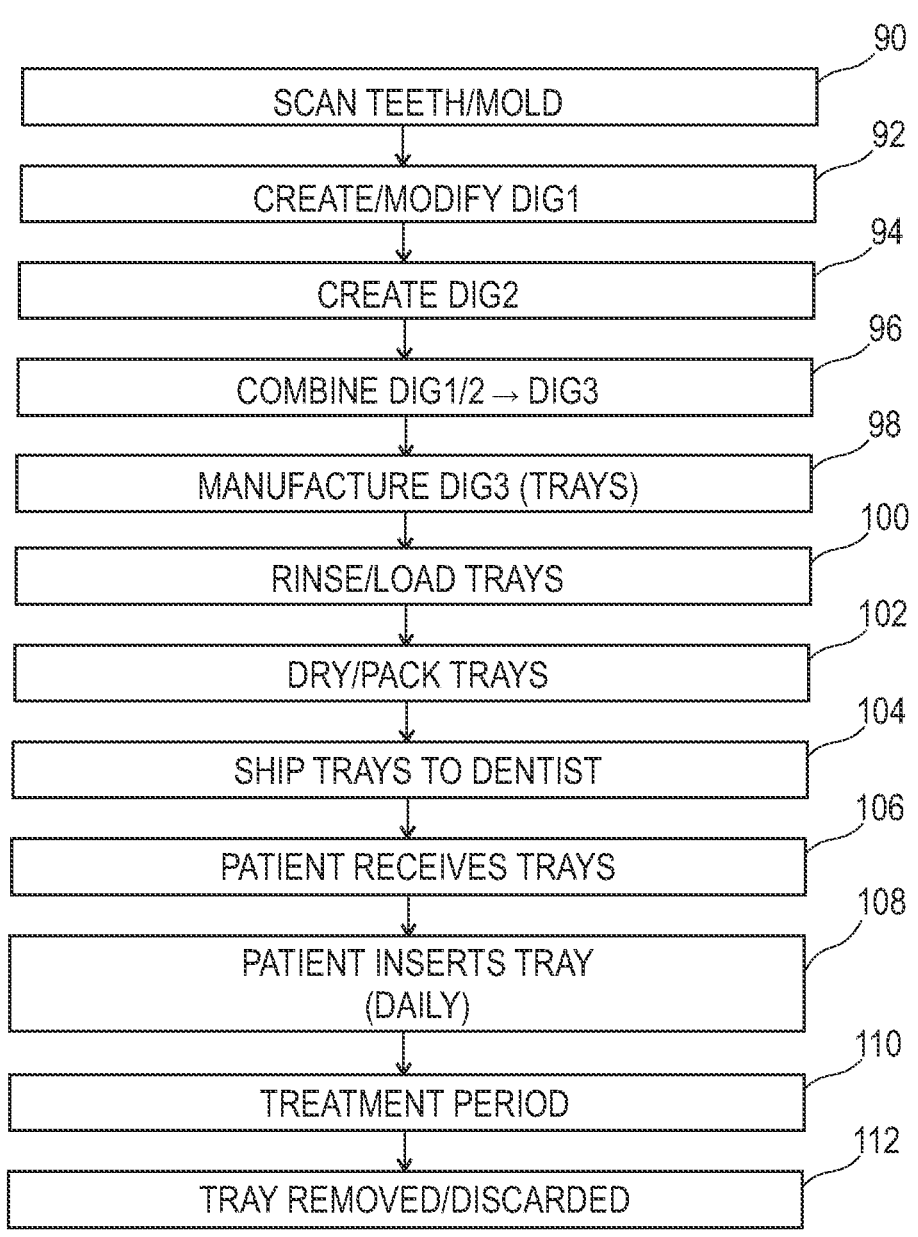

FIG. 18 is a flow chart illustrating an embodiment of the computer-implemented system to generate and manufacture an oral appliance and its use by a prospective patient.

It is to be understood that the figures are not drawn to scale. Further, the relationship between objects in a figure may not be to scale and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a medicament" includes one, two, three or more medicaments.

The term "porous" as used herein, refers to a material which is permeable such that fluids are movable therethrough by way of pores or other passages. Porous include materials that are polymers and non-polymers. An example of a porous material is a hydrogel material, a cellulosic material, concrete, ceramics, foams, sponges and derivatives thereof. The porous material may be the result of using a low or high molecular weight polymer. In some embodiments, the polymer may be porous as it is applied at a low density on the oral appliance and/or substrate, or is applied in a geometric pattern, either as a specific structure or a randomized structure.

The term "non-porous" as used herein, refers to a material which is impermeable such that fluids cannot move through the material. Non-porous include materials that are polymers and non-polymers. The non-porous material may be the result of using a low or high molecular weight polymer. In some embodiments, the polymer may be non-porous as it is applied at a high density on the oral appliance and/or substrate in a solid form with no structural spacing to hold medicaments.

The term "hydrogel" or "hydrogels" refer to a broad class of polymeric materials, that may be natural or synthetic, which have an affinity for an aqueous medium (e.g., a medicament), and are able to absorb large amounts of the aqueous medium, but which do not normally dissolve in the aqueous medium. In some embodiments, the hydrogel of the oral appliance has wicking action to absorb unwanted crevicular/sulcular fluids.

The term "medicament" as used herein, is generally meant to refer to any substance that alters the physiology of a patient. The term "medicament" may be used interchangeably herein with the terms "medicine", "medication", "drug", "therapeutic agent", "therapeutically effective amount", or "active pharmaceutical ingredient". It will be understood that a "medicament formulation" may include more than one therapeutic agent, wherein exemplary combinations of therapeutic agents include a combination of two or more medicaments.

The term "dental plaque" is a general term for the diverse microbial community (predominantly bacteria) found on the tooth surface, embedded in a matrix of polymers of bacterial and salivary origin.

The term "oral diseases" refers to diseases and disorders affecting the oral cavity or associated medical conditions. Oral diseases include, but are not limited to, inflammation, infection, dental caries, periodontal diseases (e.g., gingivitis, adult periodontitis, early-onset periodontitis, chronic periodontitis and/or aggressive periodontitis) or the like. Inflammatory diseases can also include benign and malignant tumors such as Lichen Planus and squamous cell carcinoma, respectively, as well as various yeast and fungal infections and conditions like Xerostomia.

The term "gingiva" or "gum" refers to a dense fibrous tissue and overlying mucous membrane enveloping alveolar processes of upper and lower jaws and surrounding the necks of teeth.

The term "gingivitis" refers to inflammation of gingival tissue without loss of connective tissue.

The term "inflamed tissue" refers to bone, teeth, or gingival tissue, that is red, swollen and can be painful. It will also more broadly include dental caries and/or hypersensitive areas of the teeth. Inflammation can be caused by trauma to the oral cavity, infection or other causes.

The term "periodontal disease" refers to an inflammatory process of the gingival tissues and/or periodontal membrane of the teeth, resulting in a deep gingival sulcus, possibly producing periodontal pockets and loss of alveolar bone.

The term "periodontitis" refers to inflammation and loss of connective tissue of the supporting or surrounding structure of teeth with loss of attachment. When left untreated gingivitis can progress to periodontitis, which is considered a more advanced and destructive inflammatory condition than gingivitis.

The terms, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

The term "localized" delivery includes delivery where one or more medicaments contact the tooth and/or soft tissue areas, for example, the gingival margin of the teeth or a region inside of the mouth such as the palate, or in close proximity thereto.

The term "targeted delivery" includes delivery of one or more medicaments at the target site as needed for treatment of the disease or condition including cosmetic applications. In some embodiments, the oral appliance can be used to deliver medicament to the soft tissue of the inside of the mouth, including but not limited to any soft tissue adjacent or between the teeth, including but not limited to the papilla, tissue of the upper and lower dental arches, marginal gingiva, gingival sulcus, inter-dental gingiva, gingival gum structure on lingual and buccal surfaces up to and including the muco-gingival junction and/or the palate and/or the floor of the mouth. In various embodiments, the soft tissue area includes the muco-buccal folds, hard and soft palates, the tongue (dorsal, ventral and lateral surfaces), lining mucosa (buccal and labial mucosae), and/or attached gingival tissue as well as the floor of the mouth.

The term "custom fit" as used herein, refers to an oral appliance that is specifically made via molding and/or 3D printing, to correspond to at least a portion of a tooth, a selected number of teeth, all of the teeth and/or soft tissues found in the mouth of a specific individual patient. A custom fit oral appliance is not a generic device which is then heated or otherwise manipulated by a consumer, inserted into their mouth by themselves and then molded by that consumer to fit their own mouth. The patient image is the result of an action upon that particular individual by another person whereas the consumer is acting upon himself/herself by manually manipulating the generic material.

In some embodiments, custom fit includes situations where the patient images himself or herself with a scanning device including those in a computer or smart devices (e.g., smartphones such as Apple iPhones, Android devices, Samsung Galaxy devices, or the like, as well as tablets such as Apple iPad, Microsoft Surface, or the like) and then the appliance is made as a separate act.

The top refers to the position that is the top of the inflammation on the inflamed tissue. Middle refers to the position of the inflammation that is the middle or mid-level of the inflammation. Bottom refers to inflammation that is the bottom or base of the inflammation. For example, in periodontal disease, top can refer to the top portion of the inflammation of the periodontal pocket, where the entrance of the pocket is or the gingival crest is, toward the coronal end. The bottom refers to inflammation that is at the base of the periodontal pocket, toward the apex or very end of the root or junctional epithelium or the base of the pocket. The portion between the top portion and bottom or base of the periodontal pocket is referred to as the middle portion of the periodontal pocket. Regarding inflammation of the tooth, the crown portion is considered the top of the tooth and the bottom is considered the apical portion or the very end of the root and will therefore have this spatial relationship of top and bottom no matter which jaw is being referred to or whatever the patient's position is in space.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

The headings below are not meant to limit the disclosure in any way; embodiments under anyone heading may be used in conjunction with embodiments under any other heading.

New oral appliances are provided that can target the delivery of medicament to the top portion of the inflamed tissue (e.g., inflamed gums, gum line, teeth, etc.) within the oral cavity and then target the treatment down the inflamed tissue.

Inflammation

The oral appliance can be used to treat, prevent, or reduce inflammation to the bone, teeth, or gingival tissue of the oral cavity. Inflammation can have symptoms of redness, swelling, stomatitis, bleeding of the tissue and can be painful. Inflammation can be caused by trauma to the oral cavity, infection (e.g., bacterial, fungal, viral, yeast infection), halitosis, dry mouth syndrome caused by the natural aging process with decreased salivary flow, disease such as Sjogrens, a systemic disease, a physical or chemical irritant, radiation, chemotherapy, drug induced inflammation, or an allergic reaction. Diseases associated with inflammation include, but are not limited to, gum disease, periodontal disease, peri-implantitis and oral candidiasis.

Gum disease is a common infection of both the periodontal soft tissue and bone tissue supporting the tooth. Bacterial plaque, a type of biofilm or mass of bacteria that forms a sticky membrane that develops along the gumline and then spreads over the surface of teeth, is the most common initiator of periodontal disease. The plaque triggers an immune response, which, in turn, can eventually lead to the destruction of gingival, or gum, tissue. It may also, eventually, lead to further complications, including the loss of teeth. Without treatment, the alveolar bone around the teeth is slowly and progressively lost. Unless addressed in timely manner, gum disease can advance in stages from a mild to a moderate and finally a severe form.

Periodontal disease is a chronic infection of the gum. Its manifestations include an increase in gingival sulcus (pocket or furrow) depth, loss of attachment of gums to teeth, inflamed gingival tissues, bleeding gums, loss of bone structure, bad breath and increase of plaque, calculus and a change in the bacterial flora resulting in an increase of harmful bacteria in the periodontal sulcus. The sulcus is the depth of the space below the visible gingival crest of the lower teeth and above the visible gingival crest of the upper teeth and the actual location of the gingival attachment to the tooth. It is to be noted that the spatial orientation of a person or of an upper and lower jaw does not affect the anatomical description of the sulcus and a diseased pocket where the gingival crest is always the top of a particular pocket. Sulcus depths of 1 mm to 3 mm are considered normal, greater than 3 mm and over are considered unhealthy and disease involved. Periodontal disease is commonly referred to as gum disease and is caused by the build-up and retention of dental plaque (namely, a sticky mass of harmful germs or bacteria) in the space between the gum and tooth. It is estimated that there are at least 700 different types of bacteria in one's mouth.

Figures 1A, 1B, 1C, 1D:
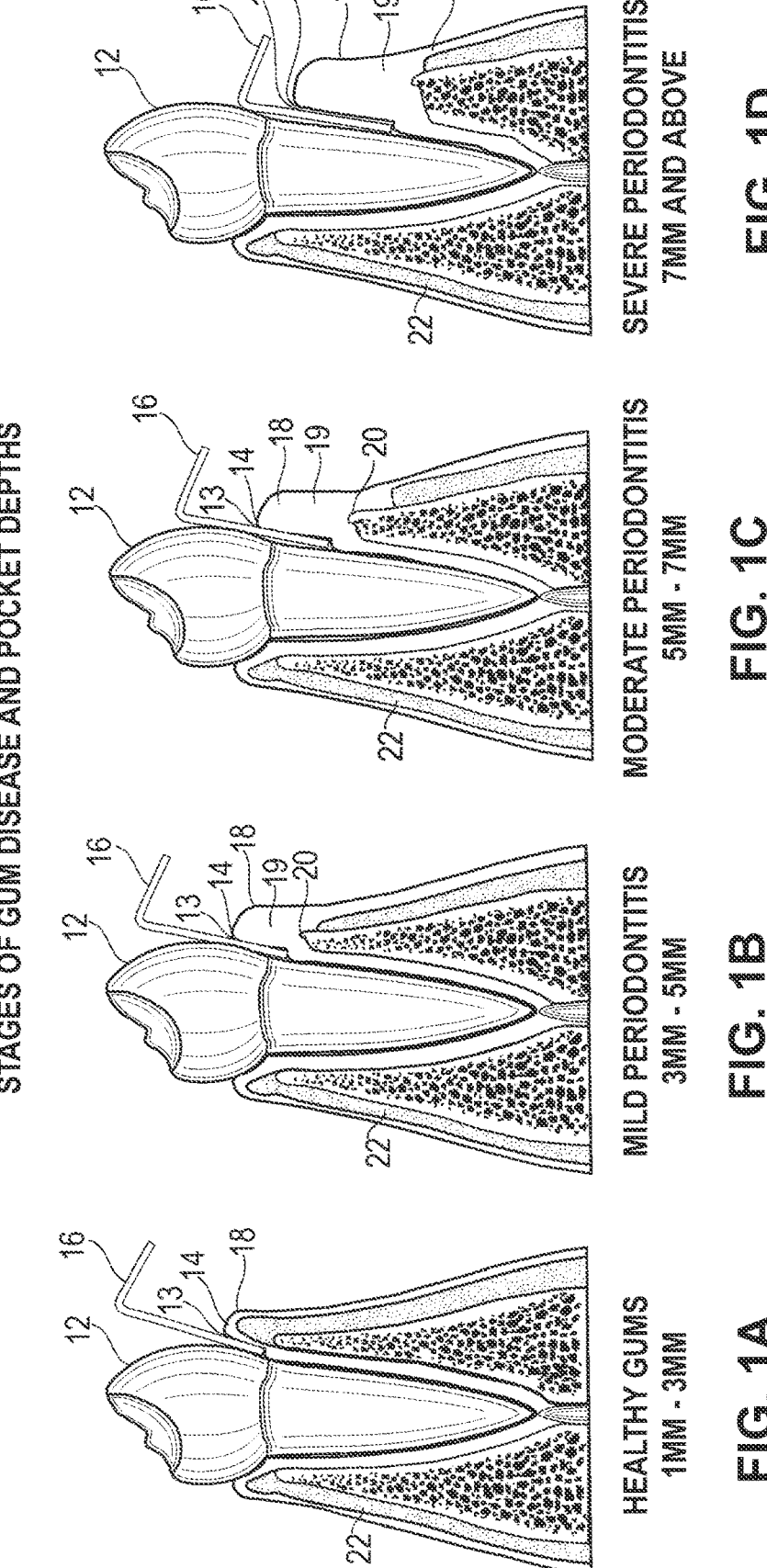
FIGS. 1A, 1B, 1C and 1D illustrate different stages of gum disease and pocket depths for healthy gums, gums afflicted with mild, moderate and severe periodontitis, respectively.

As illustrated in FIGS. 1A to 1D, dentists generally recognize four stages of gum disease. Initially, in the earliest stage of gum disease, as a result of accumulation of bacterial plaque, the gums become swollen, red and are accompanied sometimes by bad breath. In time, the bacterial plaque penetrates the sulcus, which is the space between the gum line and the tooth root. However, at this stage bone loss has not yet begun, and the damage done in this stage of gum disease is usually reversible with treatment and good oral hygiene. This initial stage is known as gingivitis and is considered by many dental professionals to be a pre-gum disease. At this stage, bacterial pockets around the teeth can be from greater than 3 mm deep to 4 mm deep. In fact, healthy gums as shown in FIG. 1A can have pocket depths from 1 to 3 mm deep.

If the pre-gum disease of gingivitis is not properly treated, periodontitis will develop that can advance from Type 1 and Type 2 of mild to moderate periodontal disease, respectively, to Type 3 of advanced or severe periodontal disease. In a slight or mild stage (Type 1) of periodontitis, there is increased gum redness, bleeding when flossing or brushing and more persistent bad breath. In a mild periodontitis, the bacterial or periodontal pockets around and between teeth deepen to from about 4 to about 5 mm as illustrated in FIG. 1B. In a moderate periodontitis stage (Type 2), the bacterial pocket can reach from about 5 to about 7 mm as shown in FIG. 1C.

In a severe or advanced periodontitis stage (Type 3), bone loss around the base of the teeth occurs and the teeth may begin to loosen as shown in FIG. 1D. Tooth loss is now possible if the disease is left untreated. In this stage, the gums are very red, swollen or inflamed, bleed easily, even when not brushing or flossing, and pus and other crevicular/sulcular fluids emanate from the periodontal pockets. In the advanced periodontitis stage, the bacterial or periodontal pockets are numerous and can reach from about 7 mm to 10 mm or more below the gum line as illustrated in FIG. 1D. From the above description, it is evident that the progression of periodontitis is incremental from the top of the gingival sulcus and progresses over time into formation of periodontal pockets of increasing depth in a top-down development. In fact, periodontal disease is diagnosed from the top-down by standard methods of assessment such as periodontal probings of the teeth at six points per tooth.

In practice, the severity of a patient's periodontal disease can be classified by any one of a variety of classification systems, such as by pocket depth that is accompanied by attachment loss; as the periodontal bleeding index; as class I, II, III or IV with class I being the least severe and class IV being the most severe. Class I periodontal bleeding index is determined when after 20 to 30 seconds of probing a single bleeding point is observed on the gums. Class II periodontal bleeding index is determined when after 20 to 30 seconds of probing a fine line of bleeding or several bleeding points are observed. Class III periodontal bleeding index is determined when after 20 to 30 seconds of probing the interdental triangle becomes more or less filled within blood. Class IV periodontal bleeding index is determined when after 20 to 30 seconds of profuse bleeding occurs.

It has been discovered that treating a gum or periodontal disease in the Top/Down method, a specific embodiment shown in FIG. 15 and FIG. 15A, in the same way that the disease usually progresses has unexpectedly beneficial results. An appliance such as an oral appliance custom fit to the specific geometries of a patient's oral cavity can deliver medication to the inflamed tissue surrounding a tooth afflicted with gingivitis and/or various stages of periodontitis. The oral appliance can contain medicament released from the porous material (e.g., a hydrogel) at discrete locations adjacent to and corresponding to the inflamed tissue present in the oral cavity. The bacteria in the periodontal pockets are predominantly aerobic at the surface and anaerobic in the depths. This bacterial gradient is attacked and modified over sustained treatments. Generally, oxygen kills anaerobic bacteria, so as the pocket shrinks, oxygen penetrates deeper into the shrinking pocket, aiding the healing process. The bacterial gradient now begins to change and contract and compress such that the good aerobes predominate further at the top and the bad anaerobes decrease in quantity at the bottom or base of the pocket. Further aiding this Top/Down method is the starvation of the anaerobes at the bottom from nutrients they get from the inflammatory response by the body since these bacteria feed on these inflammatory nutrients. As inflammation decreases and the inflammatory response decreases because of the Top/Down method, there are less nutrients for the anaerobes to feed on and therefore these bad bacteria starve and decrease. As it heals this gradient begins to shrink as more and more desirable aerobic bacteria start to dominate and the percentage of anaerobic bacteria decreases.

As these changes occur in the microbiome of the periodontal pocket, healing begins to occur in a top-down treatment and the original attachment apparatus which was damaged or destroyed by periodontitis begins to reform and reattach to the now healing bone and onto the tooth. The pocket begins to heal, and the inflamed tissues continue to shrink further. In the top-down treatment plan, treatments of the inflamed tissue can be sustained because there is now less inflammation to maintain.

Similarly, inflammation caused by viral, fungal and/or yeast infections can also be treated from the top of the inflammation down using the oral appliance of the current application.

Oral thrush or oral candidiasis is another condition in which the *Candida Albicans* fungus accumulates in the lining of the mouth causing inflammation of the oral cavity manifesting itself as creamy white lesions on the tongue, gums, inner cheeks, tonsils or the back of the throat. Oral thrush can affect anyone, but it is more prevalent in older adults having weakened immunity suppressed by other health conditions, for example, diabetes, excessive use of antibiotics, prednisone or inhaled corticosteroids. HIV/AIDS can also disturb the natural balance of microorganisms in the body including the oral cavity microbiome.

*Candida* is a fungus that naturally lives in our mouth, but when our oral microbiome is out of balance, it can grow unchecked and become a problem. Oral thrush is a common condition related to *candida* overgrowth. Oral thrush can result from excessive use of antibiotics. While antibiotics can kill harmless germs in the mouth, they do not kill *Candida*. This yeast can multiply faster when there are fewer bacteria to fight against. The same problem applies to excessively using an antibacterial mouthwash, poor nutrition and a high sugar diet. Sugar is an easy source of super-grow food for *Candida* so eating a lot of carbohydrates and sugar regularly can feed *Candida* and cause it to expand. Smoking creates an environment in the mouth that kills good bacteria but allows bad bacteria to thrive. This damages the natural balance needed to prevent *Candida* overgrowth. Oral thrush is another condition that can be treated by the oral appliances provided in this disclosure in a top-down treatment approach by placing the hydrogel or other medium not only on the inside of the appliance but also on the outside of the device and similarly as with periodontal pockets use the same concepts of sustained treatment over time and gradually change the microbiome from a diseased state to a healthy one by first attacking the *Candida* or Thrush, decreasing the inflammatory response which feeds the organisms and thus create a climate for a healthy biome to reestablish itself and flourish.

Generally, optimized supragingival oral hygiene can have a positive impact on controlling the subgingival microbiome. For example, for moderately deep periodontal pockets (4-5 mm), which generally represent a pathological state between gingivitis and Type I or mild periodontitis, oral hygiene may result in the decrease of such putative periodontal pathogens as *P. gingivalis* and spirochetes (see for example McNabb et al., J, Clin. Periodontol 1992, 19:348-356). The current application includes an oral appliance that directs medicament to the top portion of the periodontal pocket or supragingival plaque.

Targeted Medicament Delivery

In some embodiments, unlike orthodontic appliances, the present oral appliance is not designed to move teeth and is not an orthodontic appliance. Therefore, a plurality of oral appliances will be configured to fit the teeth in the same position as was imaged within the oral appliance. The tooth positions will not change. However, the medicament disposed in or on the oral appliance will be in the same or different areas at different stages of the treatment regimen with a variety of oral appliances. Thus, kits containing a plurality of oral appliances can be provided with different treatment plans. For example, as the patient condition improves, each oral appliance can have a decreasing amount of medicament or the medicament can change and be disposed at different positions (e.g., top portion or entrance of the periodontal pocket, middle or mid-level portion, bottom or apical portion, etc.) in the oral appliance adjacent to the improving inflamed tissue as the treatment of inflamed tissue in the oral cavity progresses.

In some embodiments, the present oral appliance can be utilized to adjunctively assist those orthodontic aligner appliances which are designed to move teeth and to treat the teeth and/or soft tissue area of the oral cavity with medicament disposed at discrete regions of the oral appliance without affecting the tooth movements those orthodontic aligner appliances effect. Therefore, a plurality of oral appliances can be configured to fit the inflamed soft tissues in the different positions as the teeth are moved.

In various embodiments, the oral appliance is monolithic or a single piece and the interior surface custom fit and formed to fit contours of the teeth and/or soft tissue areas inside the oral cavity of a patient in need of treatment. In some embodiments, the oral appliance of the present application has the medicament as part of the device and, in some embodiments, the medicament is not removable from it except by diffusion in the mouth. In certain embodiments, the oral appliance comprises, consists essentially of or consists of one, two, three, four, five or more oral appliances.

In various embodiments, the oral appliance is not monolithic or a single piece. The medicament is disposed on the inside and/or on the outside of the oral appliance, but as a separate component to the oral appliance. For example, the medicament can be disposed in porous material (e.g., polymer) that is configured to allow release of the medicament when the oral appliance is worn.

In some embodiments, oral appliances include, but are not limited to, oral trays, oral holders, oral covers, or the like that are designed to be placed within the oral cavity. The interior surface and/or exterior surface of the oral appliance contains a medicament disposed inside the porous portion of the polymer of the oral appliance and the medicament can be disposed anywhere within or on the oral appliance. In some embodiments, the exterior surface of the oral appliance is porous and allows medicament to be released to adjacent teeth and/or soft or hard tissue, or into the mouth in general.

Numerous different oral appliances can be made by the methods of the present application, including custom fit oral appliances that correspond to a digital scan taken from the patient's mouth or impression molds. Custom fit oral appliances are generally described in U.S. Pat. No. 9,649,182, to Peter J. Zegarelli, filed Jun. 18, 2015. The entire disclosure of this patent is herein incorporated by reference into the present disclosure.

The oral appliance, when worn, allows the interior and/or exterior surface of the oral appliance to be adjacent to the teeth and/or gums or other tissue in the oral cavity, including inflamed tissue associated with periodontal disease. In some embodiments, the oral appliance receives one or more teeth including one or more molars, premolars, incisors, cuspids, tooth implant, or combinations or portions thereof.

The contact of the oral appliance with the tissue, when the oral appliance contains medicament in the porous regions, will allow medicament to be released from the oral appliance to the inflamed target tissue areas in the oral cavity (e.g., gum, gum line, teeth, etc.) at the desired inflamed regions adjacent to the porous regions of the oral appliance. In this way, targeted therapy can be directed at the desired regions (e.g., top portion or entrance of the periodontal pocket, middle or mid-level portion, bottom or apical portion, etc.) afflicted with periodontal disease in the oral cavity. By providing an oral appliance with porous regions and non-porous regions, medicament release can be controlled to adjacent tissue or confined to those regions adjacent to the non-porous material reducing or eliminating medicament release to non-targeted areas of the mouth with sometimes deleterious effects.

In some embodiments, the oral appliance is predominantly porous (at least 51% or more) and non-porous material is coated on the oral appliance at discrete regions to make these discrete regions non-porous. In this way, medicament loading of the oral appliance and medicament release from the oral appliance is controlled as medicament will be released from the porous material at discrete regions and can target specific tissues in the oral cavity, for example, inflamed tissues associated with periodontal disease.

It will be understood that the medicament can be mixed with the polymer before, during or after the manufacture of the oral appliance.

In some embodiments, the oral appliance is made from a porous material that contains the medicament, and an agent that reduces porosity is applied to one or more discrete regions of the porous material to make the one or more discrete regions of the oral appliance non-porous as more particularly described in U.S. patent application Ser. No. 15/895,554 to Peter J. Zegarelli, filed on Feb. 13, 2018. The entire disclosure of this application is incorporated herein by reference into the present application. For example, a cross-linking agent can be used to reduce porosity of a porous oral appliance and make that region where the crosslinking agent is applied to, non-porous to reduce or eliminate medicament release from that region.

In some embodiments, the oral appliance can be made by controlling the density of the polymer during injection molding, 3D printing or additive manufacturing. For example, different polymers can be in the injection molding. A high-density polymer can be used (e.g., 50,000 MW) to form the non-porous regions of the oral appliance and a low-density polymer (e.g., 5,000 MW) having medicament can be disposed to make the oral appliance porous at discrete regions.

It will be understood that the oral appliance with discrete portions of the porous material and with discrete portions of non-porous material can be monolithic or a single piece having the same or different material. This type of oral appliance, in some embodiments, does not contain a porous insert after the oral appliance is made. Such porous inserts are described in U.S. Pat. No. 9,579,178, filed Jul. 12, 2013 to Peter J. Zegarelli. In some embodiments, the oral appliance can have the porous material as a separate insert disposed at discrete regions of the oral appliance as described in U.S. Pat. No. 9,579,178, filed Jul. 12, 2013 to Peter J. Zegarelli. The entire disclosure of this patent is herein incorporated by reference into the present disclosure.

Referring to FIGS. 1A-1D, 2B-2D, 3, 4 and 5, an oral appliance 10 is provided for delivering a medicament 26 to a least a portion of a tooth or teeth 12 and/or soft tissue areas inside an oral cavity, wherein the gum or gingiva 22 shows various degrees of periodontitis 14 as can be probed with a dental probe 16. As illustrated in FIGS. 1A-1D and 2A-2D, the depth of the gingival sulcus 13 varies as the periodontal disease progresses from healthy gums in FIGS. 1A and 2A to severe periodontitis in FIGS. 1D and 2D.

Figures 2A, 2B, 2C, 2D:
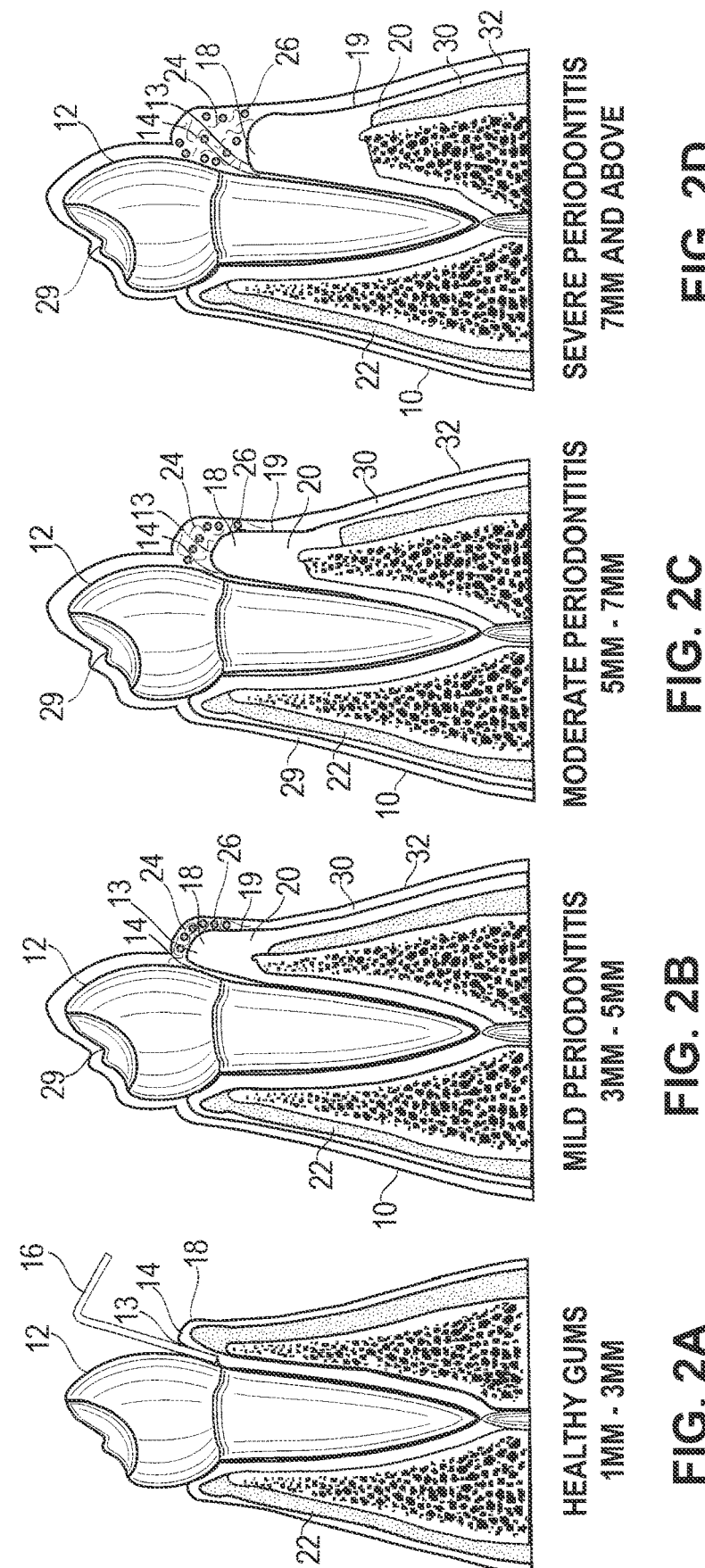
FIGS. 2A, 2B, 2C and 2D illustrate stages of targeted medicament treatment of gums afflicted with mild, moderate and severe periodontitis, respectively, with an oral appliance containing medicament in porous material located at discrete locations in the top portion of the diseased gum, all by comparison to a healthy gum illustrated in FIG. 2A. In this embodiment, the oral appliance targets the medicament to the top portion of the inflammation.

The oral appliance shown in FIGS. 2B-2D is a custom fit oral appliance, which can be formed to fit contours of and/or hold medicament in contact with at least a portion of the tooth or teeth and/or soft tissue areas, such as the gum 22 inside the oral cavity to deliver the medicament to the inflamed areas of the gum of one particular individual patient and will not fit any other person. Forensic dentistry teaches us that each mouth is legally and anatomically unique to one person. The oral appliance can be constructed from a digital data set or a physical model representing at least a portion of or all of the teeth and/or soft tissue areas inside the oral cavity. All or portions of an exterior surface 32 of FIGS. 2B-2D can be non-porous material, where the medicament will be disposed on or in the interior surface of the oral appliance to allow medicament to treat the inflamed tissue starting from the top portion of the inflammation. In this way, controlled and targeted medicament delivery can occur. The inflamed tissue can be immediately adjacent to and contacts the medicament (e.g., the medicament may be disposed on or in a porous material) to be released at the target tissue site, for example, the gingival margin, interior of the lip and the palates, floor of the mouth, the sublingual veins, the tongue, buccal mucosae and labial mucosae, generally any inflamed tissue in the oral cavity.

In some embodiments, in this application, the gingival margin of the teeth is targeted for delivery of the medicament. This is because periodontal disease (e.g., periodontitis) starts and, if left untreated, continues and is ongoing at the gingival margin of the teeth.

Figure 3:
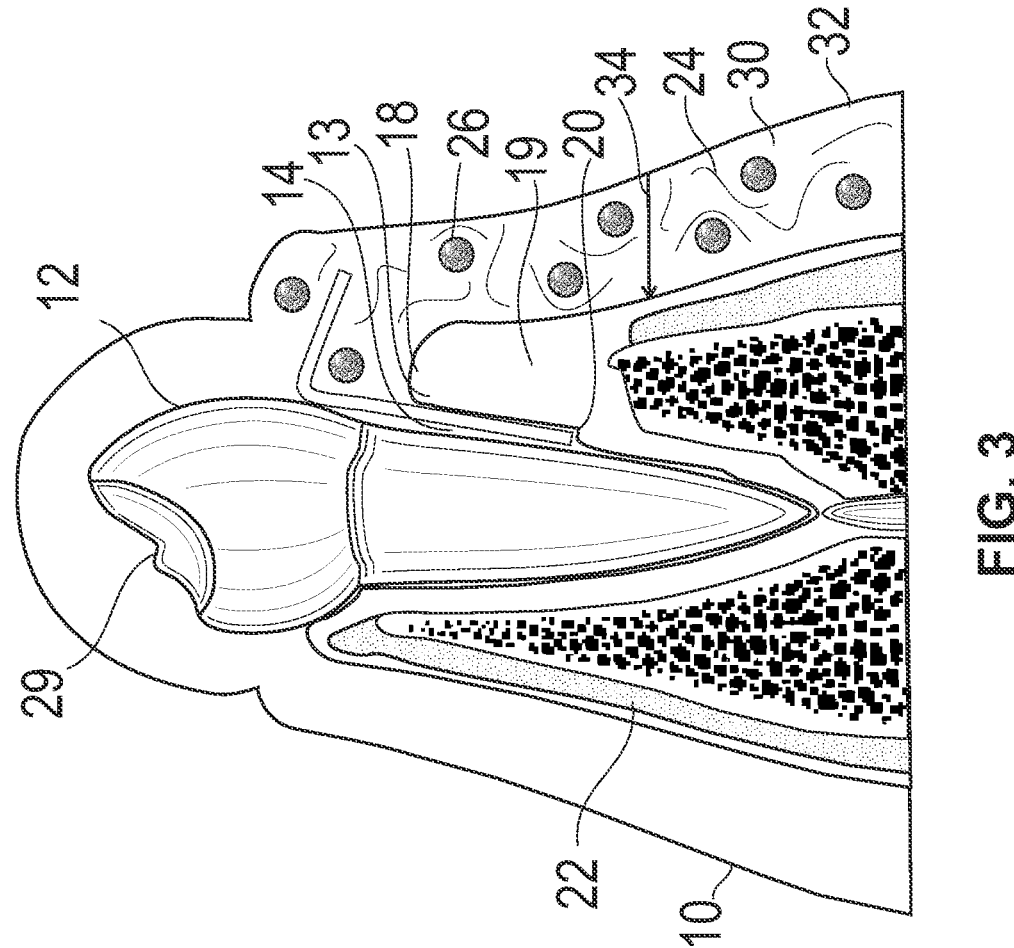
FIG. 3 illustrates the treatment of a tooth having inflammation with medication released from a porous material in a constant diffusion over time to treat the inflamed tissue. The hydrogel releases the medicament in a constant diffusion over time.

The oral appliance 10 comprises a porous material 24, in some embodiments, in the interior surface 30 of the oral appliance. The porous material 24 can be made from a polymer material such as a hydrogel or other material that will make all or portions of the oral appliance porous. The porous material can be mixed with the medicament 26 or the medicament can be added to the porous material 24 after manufacture. FIGS. 2B-2D, 3, 4 and 5 illustrate embodiments where medicament can be at discrete regions of the oral appliance. Shown are the oral appliances having the porous material disposed at discrete regions of the oral appliance adjacent to and corresponding to the top portion 18, middle portion 19 and bottom or base portion 20 of the periodontal pocket, which is the inflamed tissue exhibited by gums afflicted with periodontitis. As illustrated in FIG. 3, top portion of the pocket 18 is located at the top of the gingival crest or top of the pocket, the bottom portion of the pocket 20 is located at the bottom of the junctional epithelium or base of the pocket and the area in between top 18 and bottom 20 is middle portion of the pocket 19. In a patient with healthy gums, the top portion of the pocket can be from about 1 mm to about 3 mm in depth. In a patient having periodontitis, the top portion of the pocket is only about 1 mm in depth and the base of the pocket can vary from about 1 mm to about 4 mm. The middle portion of the pocket is the area between the top and base of the pocket. For example, in a periodontal pocket that is 7 mm in depth, the top portion of the pocket is about 1 mm, the base portion of the pocket is about 1 mm and the middle portion of the pocket is about 5 mm. If the 7 mm periodontal pocket shrinks with treatment and becomes for example about 5 mm, the middle portion of the pocket will become about 3 mm. The porous material 24 of the oral appliance is disposed in the interior of the oral appliance at discrete regions to make these discrete regions porous, while other parts of the oral appliance have non-porous material 28 as illustrated in FIG. 6. The porous material allows the medicament to be saturated within the polymer.

In various embodiments illustrated in FIGS. 2B-2D, and 3, the oral appliance 10 contains areas 29 without medicament. The areas having medicament 26 can be desirably located at discrete porous regions 24 inside the oral appliance adjacent to the top portion 18 of the gingiva 22 exhibiting periodontal disease, which can contact at least this area when worn.

In some embodiments, the present disclosure provides a system for delivering a medicament to an inflamed tissue inside an oral cavity. The system comprises a first set of oral appliances. Each of the first set of oral appliances has an interior surface 30 and an exterior surface 32. The interior surface 30 is configured to contour at least a portion of the teeth and/or soft tissue areas inside the oral cavity of a patient in need of treatment of inflamed tissue in the oral cavity. The interior surface of each of the first set of oral appliances has a medicament disposed at a discrete region of the interior surface of each of the first set of oral appliances. The medicament is configured to contact a top portion 18 of the inflamed tissue inside the oral cavity when the oral appliance is worn to cause delivery of the medicament to at least the top portion of the inflamed tissue in various stages of periodontitis as illustrated in FIGS. 2B-2D. As the oral appliance is worn, the inflamed tissue (e.g., gums) will heal and generally shrink and thus retract away from its original geometries thereby moving away from the oral appliance.

In many aspects, the first set of oral appliances can be disposable. In other embodiments, a second set of oral appliances is provided which can reflect the change in gum architecture as the gums shrink from healing in the top-down method with healing and decreased inflammation, new imaging may be required to accurately reflect the new contours so that the hydrogel may need to be altered through Dig2 to create wholly new devices such that each of the second set of oral appliances has an interior surface configured to contour at least the portion of teeth and/or soft tissue areas inside the oral cavity, the interior surface of each of the second set of oral appliances having a medicament disposed at a discrete region 38 of the interior surface 30 of each of the second set of oral appliances as illustrated in FIG. 6.

FIG. 3 illustrates the treatment of a tooth having inflammation with medication released from a porous material 24 in a constant diffusion over time to treat the inflamed tissue. The hydrogel releases the medicament 26 in a constant diffusion over time as indicated in FIG. 3 by arrow 34.

Figure 4:
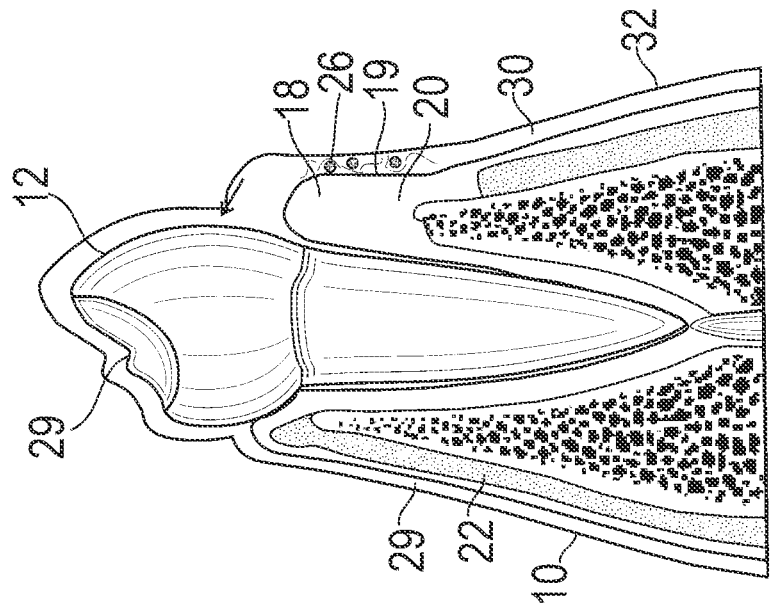
FIG. 4 illustrates an optional embodiment of the oral appliance being used to treat inflamed tissue, where the oral appliance contains medicament in porous material located at discrete locations in the middle or mid-level portion of the inflamed tissue. In this embodiment, the oral appliance targets the medicament to the middle or mid-level portion of the inflammation.

FIG. 4 illustrates an optional embodiment of the oral appliance 10 being used to treat inflamed tissue, the oral appliance containing medicament 26 in porous material located at discrete locations in the middle 19 or mid-level portion of the inflamed tissue. In this embodiment, the oral appliance targets the medicament to the middle or mid-level portion of the inflammation. This can be the second set of oral appliances used to treat the middle portion of the inflamed tissue after the patient has worn a first set of oral appliances, the first set targeting the top portion of the inflamed tissue.

Figure 5:
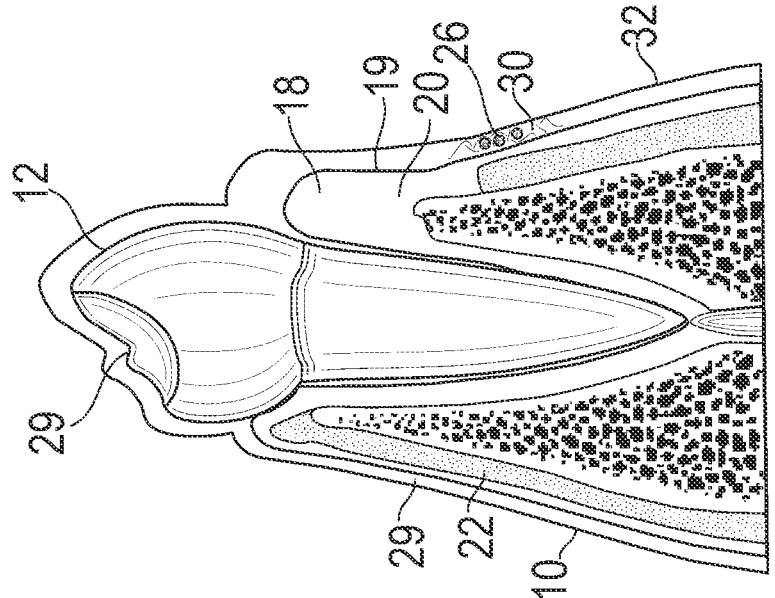
FIG. 5 illustrates an optional embodiment of an oral appliance containing medicament in porous material located at discrete locations in the base portion of the inflamed tissue. In this embodiment, the oral appliance targets the medicament to the base portion of the inflammation.
Figures 6, 7:
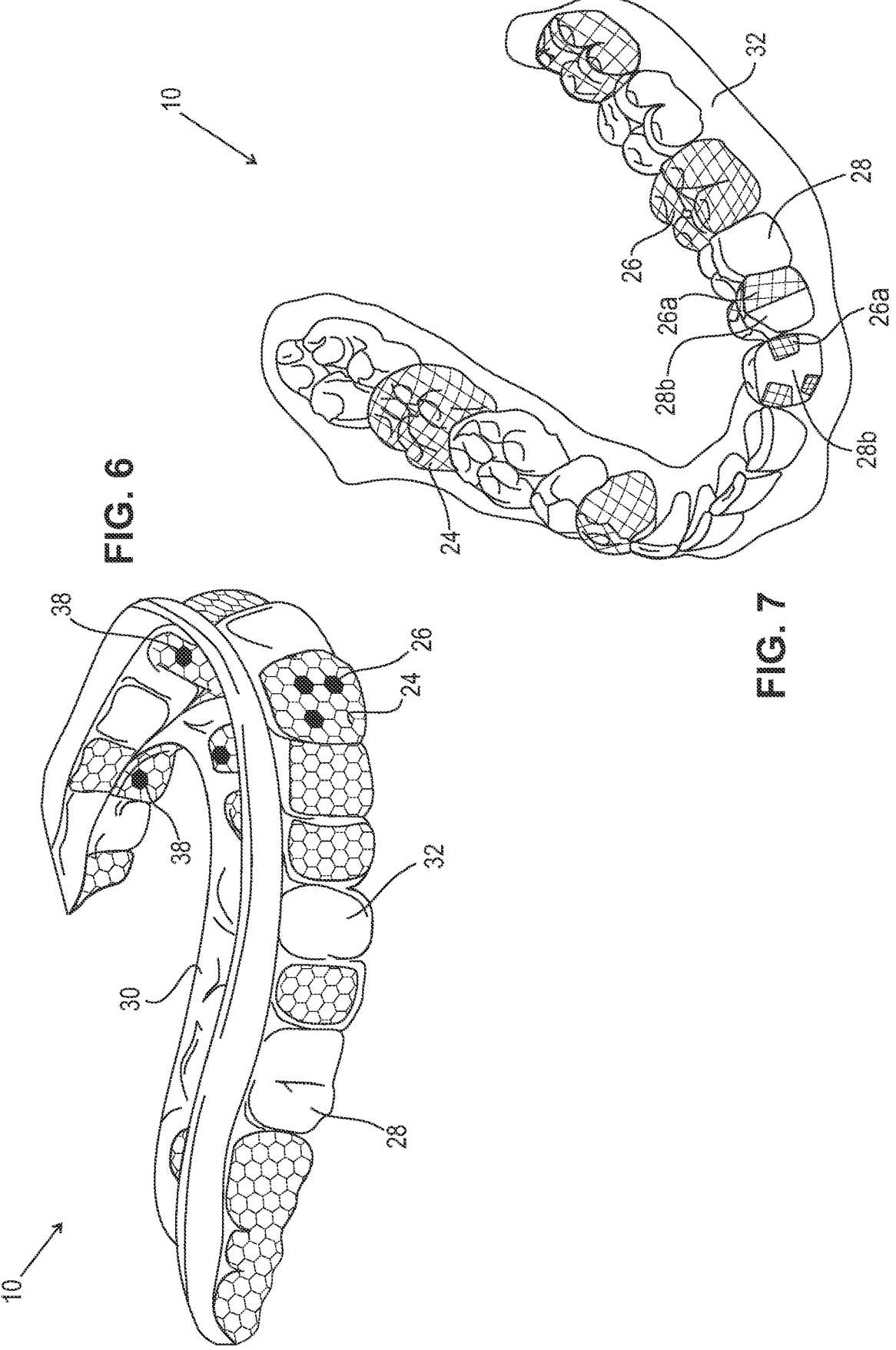
FIG. 6 illustrates a perspective view of an embodiment of the oral appliance, where the porous material comprises an open cell, lattice, honeycomb, or other random or geometric patterned configuration at discrete locations that can contain medicament to target its delivery to the oral cavity.
FIG. 7 illustrates a perspective view of the oral appliance of FIG. 6 covering the lower teeth and/or soft tissues including inflamed tissues of a patient. The oral appliance is custom-fit to contour the teeth and/or soft tissue areas of the oral cavity.
Figure 9:
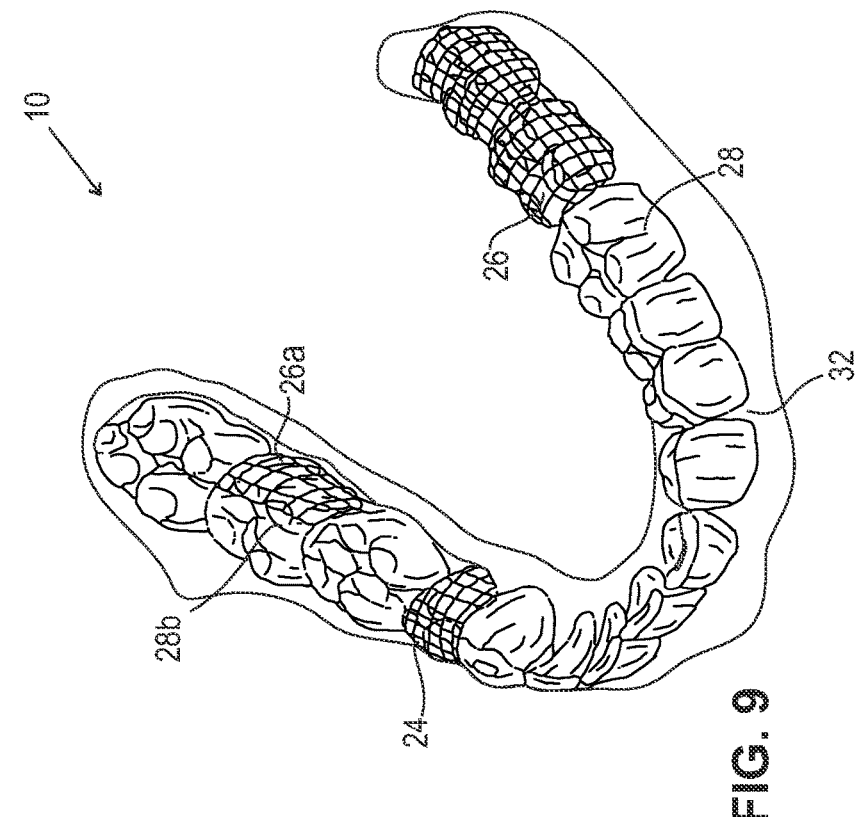
FIG. 9 illustrates a perspective view of the oral appliance of FIG. 6 covering the lower teeth and/or soft tissues including inflamed tissues of a patient.
Figure 8:
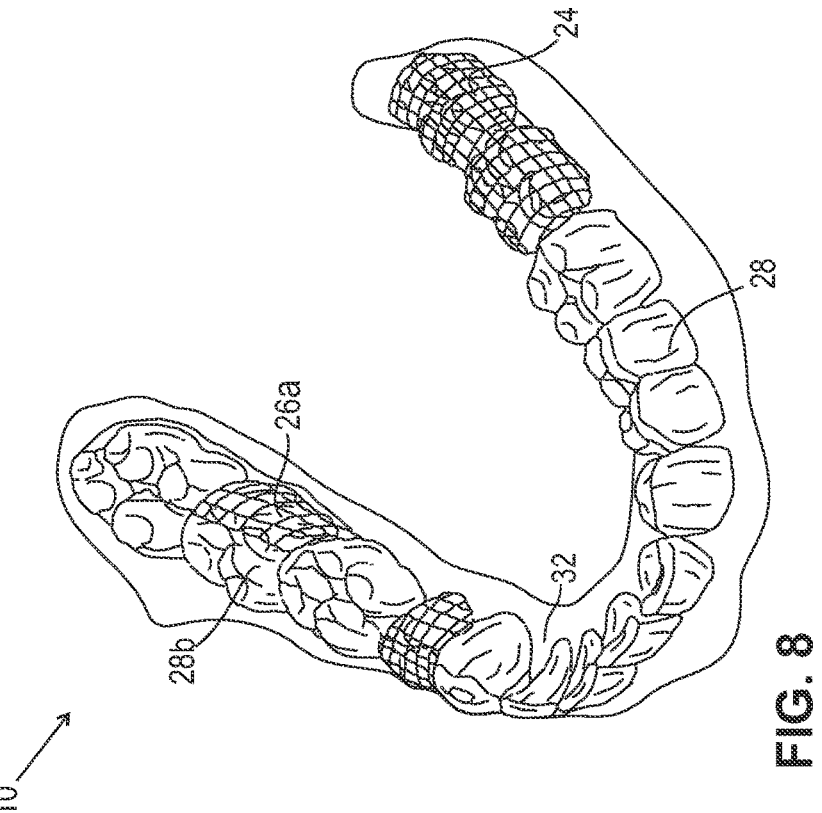
FIG. 8 illustrates a perspective view of the oral appliance of FIG. 6 covering the lower teeth and/or soft tissues including inflamed tissues of a patient.

FIG. 5 illustrates an optional embodiment of an oral appliance 10 containing medicament 26 in porous material located at discrete locations in the bottom portion 20 or apical portion of the inflamed tissue. In this embodiment, the oral appliance targets the medicament to the bottom portion of the inflammation. This can be the third set of oral appliances used to treat the bottom portion of inflamed tissue after the patient has worn a first set and second set of oral appliances targeting the top portion of the inflamed tissue and the middle of the inflamed tissue.

In various embodiments, the system for delivering a medicament to an inflamed tissue inside an oral cavity further comprises a fourth set of oral appliances, each of the fourth set of oral appliances having an interior surface configured to contour at least a portion of teeth and/or soft tissue areas inside the oral cavity, the interior surface of each of the fourth set of oral appliances having a medicament disposed at a discrete region 38 of the interior surface of each of the fourth set of oral appliances, wherein the medicament is a probiotic.

In some aspects, a system for treating inflamed gum tissue surrounding a tooth inside an oral cavity is provided, the system comprising a plurality of disposable oral appliances, each oral appliance having a shell or exterior surface over at least a portion of the tooth and inflamed gum tissue, each shell having an interior surface with cavities and material containing a medicament, the shell configured to collect crevicular/sulcular fluid, each appliance being formed to fit tightly over the inflamed gum tissue from one arrangement to a successive arrangement, each successive arrangement configured to fit tightly over a progressively less inflamed gum tissue relative to previously treated inflamed gum tissue area.

In other embodiments, a system for treating inflamed gum tissue surrounding a tooth inside an oral cavity, the system comprising a plurality of oral disposable appliances, each oral appliance comprising a shell over at least a portion of the tooth and inflamed gum tissue, each shell having material containing a medicament, the shell configured to collect crevicular/sulcular fluid, wherein the surfaces of successive shells are shaped to fit tightly over the inflamed gum tissue inside the oral cavity from one arrangement to a successive arrangement, each successive arrangement configured to fit tightly over the gum that is progressively less inflamed relative to previously treated inflamed gum tissue area. In many embodiments, the shell of the oral appliance comprises an internal surface having a porous material containing a medicament at discrete regions inside the oral appliance and a non-porous material disposed on or in one or more discrete regions of the porous material to make the one or more discrete regions of the oral appliance non-porous. The oral appliance is formed to fit contours of at least the portion of the teeth and/or inflamed gum tissue areas inside the oral cavity and is also configured for holding the medicament in contact with at least the portion of the tooth and/or inflamed gum areas inside the oral cavity to deliver the medicament thereto. The shell of the disposable oral appliance comprises a porous material containing a medicament and a non-porous material disposed on or in one or more discrete regions of the porous material to make the one or more discrete regions of the oral appliance non-porous, the oral appliance being formed to fit contours of at least the portion of the teeth and/or inflamed gum tissue areas inside the oral cavity and being configured for holding the medicament in contact with at least the portion of the tooth and/or inflamed gum areas inside the oral cavity to deliver the medicament thereto.

In some aspects, the porous material includes a polymer, which can be a hydrogel. The polymer allows the medicament to be saturated within the polymer. The porous material comprises from about 60% to about 99% by weight of the oral appliance. In some embodiments, the porous material comprises from about 65% to about 95%, from about 70% to about 90%, from about 75% to about 85%, or from about 80 to about 82% by weight of the oral appliance. In some embodiments, the porous material comprises from about 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 to about 99% by weight of the oral appliance. The porous material can cover a part or a portion of a tooth, as shown as 26a in FIGS. 6-9. The porous material can cover a part or a portion of a tooth or teeth and/or soft oral inflamed tissue such that those particular portions selected can be the only portions treated by the medicament.

The oral appliance can comprise a non-porous material 28 as illustrated in FIG. 6. The non-porous material is disposed on or in one or more discrete regions of the porous material to make the one or more discrete regions of the oral appliance non-porous. In some embodiments, the medicament is not added before or after manufacture to the non-porous regions of the oral appliance. The non-porous material reduces medicament release from the oral appliance. The non-porous material can be a cross-linked polymer. For example, the entire oral appliance can be made from a porous material and a polymer crosslinking agent can be applied to the oral appliance at discrete regions of the oral appliance to make these discrete regions non-porous. In various aspects, the porous material can comprise from about 60% to about 99% by weight of the oral appliance. In other aspects, the non-porous material can comprise from about 0.25% to about 10% by weight of the oral appliance.

FIG. 6 illustrates another embodiment of the oral appliance 10 made by controlling the print density of the polymer during injection molding, 3D printing or additive manufacturing. For example, the same polymer can be printed (e.g., using the same print head) by programming the computer to have the 3D printer print the polymer at a density of, for example, 0.25 g/cm$^3$ to 0.5 g/cm$^3$ at discrete regions to form the porous material regions 24 of the oral appliance, and the printer can be set to print the polymer at a higher density, for example, 0.8 g/cm$^3$ to 1.5 g/cm$^3$ to make the oral appliance non-porous at discrete regions with highly dense polymer printed to form the non-porous material 28 at discrete regions of the oral appliance.

Some printing densities of the polymer can be from about 0.25 g/cm$^3$, 0.3, 0.35, 0.4, 0.45, 0.5, 0.55, 0.6, 0.65, to about 0.7 g/cm$^3$ that can form the porous region of the oral appliance. This region can be saturated with medicament. The medicament can be mixed with the polymer before or during 3D printing or can be added to the porous regions after printing.

As shown in FIG. 6, the non-porous material 28 does not contain portions of open cells, lattices or honeycombs. It is solid with no porosity and thereby no spacing to hold or absorb medicaments. These regions of the oral appliance 10 will allow little or no medicament to contact the target tissue area in the mouth. In the embodiment shown, the oral appliance can have portions of open cells, lattices, honeycombs, or have sponge-like configurations as part of the oral appliance at discrete regions of it to target the areas to be treated. In some embodiments, the porous material 24, or discrete regions of the oral appliance includes or is manufactured to include carbon foam, polymer(s), or a combination thereof. The foam can be a carbon foam lattice, such as carbon resin DPR 10 (Carbon 3D, Inc. C.A.). In various embodiments, the porous material includes medicament 26. Shown in this figure is medicament disposed at discrete regions of the oral appliance so that the medicament can be delivered to hard tissue including the teeth.

In some embodiments, the non-porous material comprises from about 0.25, 0.3, 0.35, 0.4, 0.45, 0.5, 0.55, 0.6, 0.65, 0.7, 0.75, 0.8, 0.85, 0.9, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, to about 99% by weight of the oral appliance.

The non-porous material can be disposed on or in one or more discrete regions of the porous material such that the tooth, teeth and/or soft tissue areas that correspond to this region or regions is not treated with the medicament. In some embodiments, the non-porous material can cover a part or portion of a tooth, as shown as 28b in FIGS. 7-9. In some embodiments, the non-porous material is a coating that is applied to discrete regions of the oral appliance and/or porous material. Such coating for example can be a crosslinking agent, which allows crosslinking of the porous polymer to reduce or eliminate medicament release from the oral appliance and/or confine medicament to a portion of the teeth and/or gum that is adjacent to the non-porous region of the oral appliance.

In some embodiments, the non-porous material can be coated on the oral appliance at discrete regions of it and the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the medicament from the oral appliance. In some embodiments, the range of the coating on the oral appliance ranges from about 5 microns to about 250 microns or 5 microns to about 200 microns to delay release of the medicament from the oral appliance.

The oral appliance includes an interior surface 30 and an exterior surface 32. The interior and exterior surfaces are defined by the porous and non-porous materials of the oral appliance. The interior surface is custom formed to fit contours of at least a portion of the teeth and/or soft tissue areas inside the oral cavity and is configured for holding the medicament in contact with at least the portion of the teeth and/or soft tissue areas inside the oral cavity to deliver the medicament thereto. With reference to FIGS. 2B-2D, 3, 4 and 5, in various embodiments, the interior surface 30 of the oral appliance 10 has a medicament 26 disposed at a discrete region 24 of the interior surface 30 of the oral appliance 10, the medicament configured to contact a top portion 18 of the inflamed tissue inside the oral cavity when the oral appliance is worn to cause delivery of the medicament to at least the top portion 18 of the inflamed tissue of the gum. In other embodiments, the oral appliance 10 comprises the medicament 26 inside the interior surface of the oral appliance disposed at the middle portion 19 or mid-level portion of the inflamed tissue of the gum, shown in FIG. 4. In yet other embodiments, the oral appliance 10 has the medicament 26 inside the interior surface 30 of the oral appliance 10 disposed at the bottom portion 20 of the inflamed tissue of the gum, shown in FIG. 5.

As shown in FIG. 10, the oral appliance 10 can be formed of material containing the medicament 26, in which the oral appliance may have a shape contoured to fit the teeth and/or gums. In other embodiments, the discrete region of the interior surface of the oral appliance comprises one or more layers of porous material. In one embodiment, as illustrated in FIG. 10A, one layer of porous material comprises an antibiotic 23 (e.g., chlorhexidine), which can deplete the microbiome of the oral cavity of good bacteria. Another porous material adjacent to the layer of antibiotic comprises a probiotic 25, which can reconstitute the microbiome of the oral cavity.

In some embodiments, the non-porous material is the structural backbone of the oral appliance and is present throughout the oral appliance to give it form, shape and structural integrity. The porous material parts of the oral appliance are strategically placed about the oral appliance in order to deliver medicaments to those inflamed areas to be treated inside the oral cavity. These areas can be either internal or external to the oral appliance.

The oral appliance may have a porosity suitable for release of the liquid medicament upon application of the liquid medicament to the oral appliance. The porosity of the oral appliance ranges from about 1 micron to about 750 microns, from about 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740 to about 750 microns. In some embodiments, the oral appliance has a porosity ranging from about 100 microns to about 500 microns.

The oral appliance has a thickness of from about 0.06 inches to about 0.2 inches. In some embodiments, the oral appliance has a uniform thickness or a non-uniform thickness ranging from about 0.06, 0.07, 0.08, 0.09, 0.10, 0.11, 0.12, 0.13, 0.14, 0.15, 0.16, 0.17, 0.18, 0.19, to about 0.2 inches. The oral appliance can have a uniform or non-uniform thickness of about 0.2 to about 0.5 inches. In some embodiments, the oral appliance comprises a semi-solid construction.

Specific Embodiments of the Top Down Treatment of Periodontal Disease

Periodontal disease starts from the coronal portion of the gums (the "top" of the gums), and over time, makes its way apically subgingivally ("down" the gums). The disease progresses from the "top, down," forming a gradient of microbiota down the length of the pocket. Coronally, towards the top, exist more aerobic bacteria. Apically, towards the base of the pocket, exist more anaerobic bacteria. By treating the disease in its initial pattern of progression from the top-down, the gradient will shrink, iteratively narrowing the gradient until the pathologic anaerobic bacteria are inhibited. In this embodiment, a top-down method for treating periodontal disease is provided. This method allows patients to treat periodontal disease effectively at home, in adjunct with professional services.

Currently available treatment modalities for periodontal disease are either surface in nature (e.g., only reaching the first 3-4 mm of free gingiva) or target the base of the pocket. In this embodiment of the current application, periodontal treatment is targeted in the way the disease has progressed: treating periodontal disease from the top, down.

The top down method for treating periodontal disease mimics the periodontal disease model by targeting the bacterial infection present using an antimicrobial sustained regimen using the oral appliance as described herein. It is a progressive system which attacks the disease over a sustained period, daily and consistently in order to whittle away the dysbiotic biome and encourage the growth of a healthy biome. It views the healing process as a continuum just as the original disease process was a continuum of destruction that occurred daily, chronically in a sustained manner of a period of time.

Figure 13:
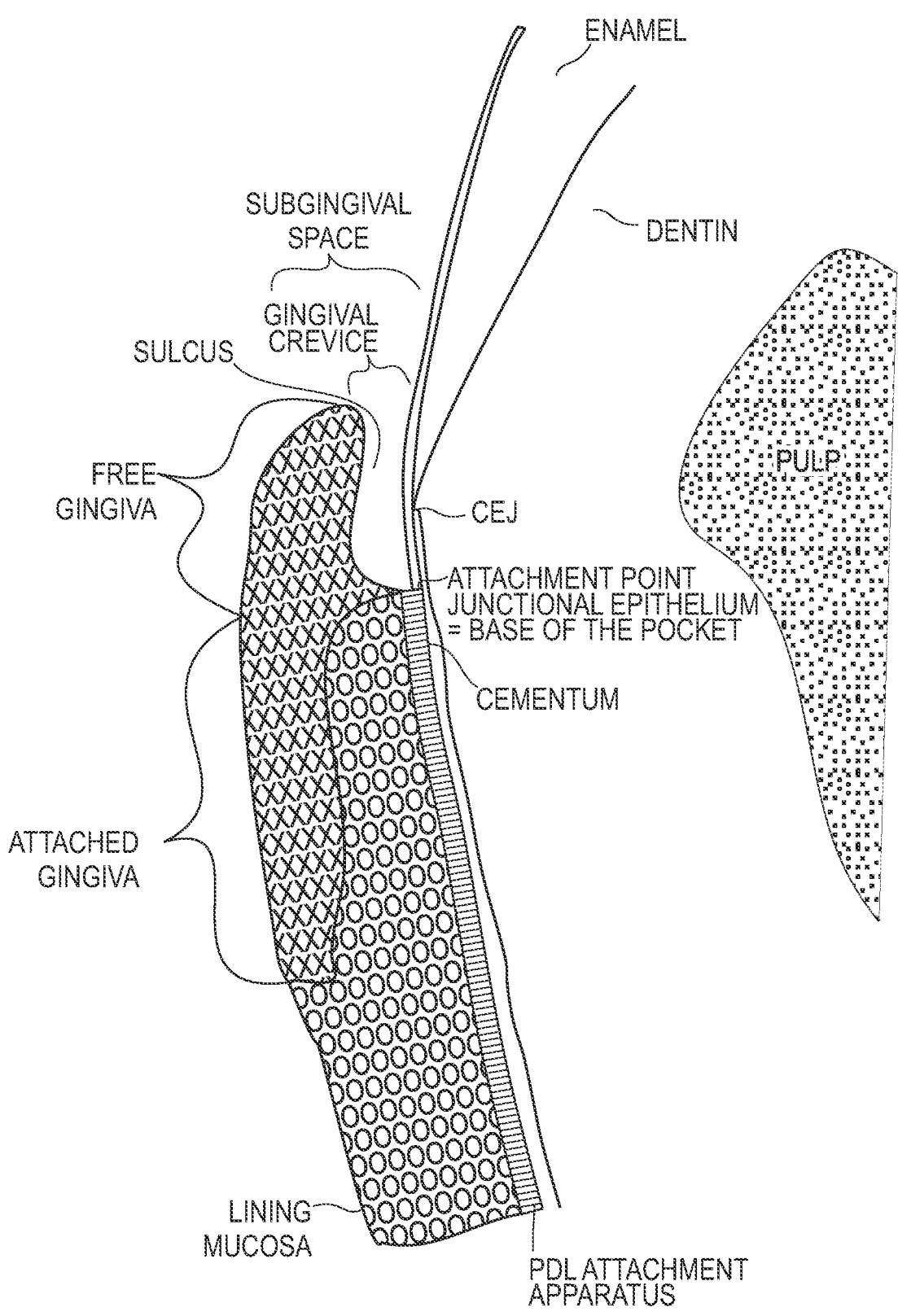
FIG. 13 illustrates an enlarged cross-sectional view of the anatomy of the gums and a tooth including free gingiva, attached gingiva, lining mucosa, the periodontal pocket or crevice, the cementoenamel junction (CEJ), periodontal ligament, cementum, the enamel, dentin, pulp and the junctional epithelium which is the base or bottom of the pocket. In some embodiments, the periodontal pocket is targeted for delivery. The design of the medicament of the oral appliance is to target the periodontal pocket or crevice of the sulcus and extrude the medicament into the entrance of the periodontal pocket.

FIG. 13 illustrates an enlarged cross-sectional view of the anatomy of the gums and a tooth including free gingiva, attached gingiva, lining mucosa, the periodontal pocket or crevice, the cementoenamel junction (CEJ), periodontal ligament (PDL), cementum, the enamel, dentin, pulp and the junctional epithelium or base of the pocket. In some embodiments, at the beginning of treatment, the top portion of the periodontal pocket is targeted for delivery of the medicament in a top down approach.

In some embodiments, the oral appliance contains porous material (e.g., a hydrogel), which can contain a medicament (e.g., chlorhexidine), which is released for a sustained period of time until the infection is reduced and is brought under greater control. The oral appliance described herein serves multiple purposes. It holds the medicament in place with no or limited dilution by saliva or contamination by oral liquids, and it keeps medicament at the top portion of the periodontal pocket. As the hydrogel is squeezed when the oral appliance is worn, the medicament diffuses into the top portion of the pocket. The oral appliance design, characterized by the hydrogel placement over the gingival crevice, is akin to an encapsulation device, sealing off the opening of the pocket from outside contamination by saliva and other liquids, and forcing the hydrogel containing medicament into the pocket entrance.

By encapsulating the gingival crevice, which is the entrance to the periodontal pocket, the oral appliance assures that the captured fluids, which are those fluids coating and surrounding the teeth and soft tissues when the tray is inserted, are pushed away from the crevice entrance and kept away by the encapsulating hydrogel over the crevice. Further, as the hydrogel is emptied of medicament, Gingival Crevicular Fluids (GCFs) are wicked up and absorbed by the hydrogel in a fluid exchange, removing this contaminated exudate from the infected periodontium. GCFs include exudate fluids containing bacteria, dead cellular structures, interstitial fluids, inflammatory factors, etc. The greater the degree of inflammation due to the periodontal disease, the greater the rate of flow of the GCF. Removing the GCF from the pocket creates space for the medicament and/or hydrogel to occupy. This will result in decreased inflammation and thus decreased GCF flow. As the gingiva at the top portion of the periodontal pocket begins to respond to the medicament (e.g., antimicrobial), the surface inflammation will decrease, and the pocket will also shrink in depth. Once the antimicrobial treatment regimen has adequately reduced the pathologic microbiome, other avenues of treatment can be initiated to combat the other aspects of the periodontal disease sequence.

FIG. 14 illustrates an enlarged cross-sectional view of a portion of the oral appliance 400 that can be used in the top down approach. In the embodiment shown, medicament is disposed in a porous material 402 that is a hydrogel 404 at a discrete region of the oral appliance. The hydrogel is shown in an uncompressed state 405 and when worn with slight pressure, the hydrogel will be compressed against, among other things, the gingival crevice or periodontal pocket causing a seal of the entrance of the gingival crevice or periodontal pocket, which prevents other oral fluids (e.g., saliva, exudates, foreign liquids) from entering the crevice or pocket, which allows release of the medicament in the gingival crevice or periodontal pocket and allows the hydrogel to absorb or wick fluid from the crevice or pocket. In this embodiment, the hydrogel is disposed at a discrete region of the oral appliance and is sized to be greater than the height, width, and length of the entrance of the periodontal pocket or crevice. In this way, when the device is worn, the hydrogel will contact the entrance of the periodontal pocket or crevice and encapsulate and seal it. In some embodiments, when the device is worn there will be a gap formed between the entrance of the periodontal pocket or crevice (top portion) and the bottom or apical portion of the pocket by the junctional epithelium or base of the pocket that will allow, among other things, medicament to leach out of the hydrogel and treat the top portion of the periodontal pocket.

FIG. 15 illustrates an enlarged cross-sectional view of a portion of the oral appliance 400 being worn that is placed adjacent to the teeth and gums using the top down approach to treating periodontal disease. In the embodiment shown, medicament is disposed in a porous material 402 that is a hydrogel 404 at a discrete region of the oral appliance. The hydrogel is shown in a compressed state 407, where the device is worn and the hydrogel is compressed against, among other things, the gingival crevice or periodontal pocket causing a seal 413 of the entrance of the gingival crevice or the top of the periodontal pocket, which prevents oral fluids (e.g., saliva, exudates, foreign liquids, etc.) from entering the crevice or pocket. There is a gap 415 between the junctional epithelium or the base of the pocket and the entrance 411 or top portion of the crevice or pocket, which is now sealed by the hydrogel. This gap allows the hydrogel to release medicament in the gingival crevice or periodontal pocket to treat deep down into the inflamed tissue. The medicament release is shown by the down arrows 406. The hydrogel also absorbs or wicks oral fluids from the crevice or pocket which aides healing, shown by the up arrows 408. The hydrogel is placed in the oral appliance and it is configured to create a seal at the entrance or top portion of the periodontal pocket so that there will be a bulge of hydrogel at the entrance or top portion to cause such a seal 413.

As the medicament is leached out of the hydrogel, empty hydrogel spaces open up and become available to absorb and remove crevicular/sulcular fluids from the environment. In this way, the hydrogel has dual ability to deliver medicament and wicking action to remove crevicular/sulcular fluids from the environment. This dual action of wicking which then creates a negative crevicular fluid flow, allows the medicaments under pressure, shown by pressure points A, B and C, to enter the top portion of the pocket to fill the resultant negative pressure void, thus inserting the medicaments further into the pockets. Over sustained daily treatment regimens, the inflammation at the top portion of the pocket decreases and with decreased inflammation there is decreased swelling and therefore decreased pocket depth. The entrance 411 is located at the gingival margin of the tooth having the periodontal pocket measured more specifically from the gingival crest 418 to the depth of the pocket at the junctional epithelium or the base of the pocket 420 as illustrated in FIGS. 15 and 15A. It is well known that periodontal disease (e.g., periodontitis) starts at the gingival margin and, if left untreated, continues and is ongoing until loss of connective tissue of the supporting or surrounding structure of teeth with loss of attachment occurs. The top-down targets the gingival margin where the periodontitis starts, and if left untreated, continues to attack the gums. However, in the top down treatment method, by targeting the gingival margin for treatment over an ongoing period of time, the periodontitis is continuously treated until there is a reduction in inflammation or the pocket shrinks and the gums shrink back to their normal, healed state size and become pink and firm.

In some embodiments, the oral appliance is disposable because once the medicament completely diffuses out of the hydrogel, the hydrogel then fills up with the crevicular/sulcular fluids, which can be disposed. The medicament is now delivered into the periodontal pockets that are now open due to the absorption void created by the departure of crevicular/sulcular fluid. This process, in some embodiments, can be repeated every day and over time each periodontal pocket begins to shrink at the top portion. The inflamed tissue over time gradually shrinks and the outward flow of crevicular/sulcular fluids emanating from the periodontal pockets also decreases because of decreased inflammation. This improved pressure cycling further allows deeper penetration of the medicaments into ever greater depths of the pocket in a gradual top down approach.

In some embodiments, the patient's oral cavity can be rescanned, and a second oral appliance can be created, in which the oral appliance geometries are changed according to new data imaging in order to constantly readapt the oral appliance and the hydrogel to assure prevention of fluid contamination.

In some embodiments, the physical characteristics and measurements of the periodontal pockets can be recorded as well as other assay features such as bleeding points, probings, and bacterial counts to generate data points. These data points can be used to then coordinate one or more medicaments for the oral appliance to provide a suitable environment for healing the periodontal pocket. In this way, different and personalized medicament treatments in the oral appliance can be customized according to each individual patient's profile and response to treatment.

In some embodiments, there can be a cocktail of medicaments in the hydrogel to treat periodontal disease from different avenues to not only kill bacteria but also to promote healing at the same time. At this time, the antimicrobial use might be decreased and other anti-inflammatory medicaments would be used to promote this healing phase of the top down treatment. Further, when the microbiome of the periodontal pocket is sufficiently healed, for example, the antimicrobial use would be discontinued and the oral appliance can contain a probiotic of good bacteria to recolonize the periodontal pocket since use of the antimicrobial at this point would kill the good probiotic bacteria. In some embodiments, the patient's own tissue (e.g., gingiva) can be placed in the oral appliance at a discrete region and used to seed and cultivate the patient's own good bacteria in the oral cavity. This can be used as the patient's own site-specific biocompatible probiotic. In some embodiments, the patient's own tissue can be used as an autograft in the oral cavity.

FIG. 15A illustrates an enlarged cross-sectional view of a portion of the oral appliance 400 that is placed adjacent to the teeth and gums. In the embodiment shown, medicament is disposed in a porous material 402 that is a hydrogel 404 at a discrete region of the oral appliance. The hydrogel, with slight pressure (shown as pressure points A, B and C), when the device is worn is in a compressed state 407, where the hydrogel is compressed against, among other things, the gingival crevice or periodontal pocket causing medicament to be released shown by the down arrows 406 through the gingival crevice or periodontal pocket to treat the inflamed tissue. The hydrogel is placed in the oral appliance and it is configured to create an encapsulation or seal at the entrance of the periodontal pocket so that there will be a bulge of hydrogel at the entrance to cause such a seal 413. The hydrogel also seals the entrance 411 of the gingival crevice or periodontal pocket, which prevents oral fluids (e.g., saliva, exudate, foreign fluids, etc.) from entering the crevice or pocket. There is a gap 415 between the junctional epithelium and the entrance 411 of the crevice or pocket, which is now sealed by the hydrogel. This gap allows the hydrogel to release medicament through the gingival crevice or periodontal pocket to treat deep down into the inflamed tissue. The hydrogel also absorbs or wicks GCFs from the crevice or pocket, which aides healing as the medicament is released from the hydrogel. The hydrogel can be layered with different concentrations of medicament.

In FIG. 15A, the hydrogel has an upper surface 403 and a lower surface 409 that will contain less medicament as it interacts with the more prolific fluid amounts of the captured fluids in the tray and the saliva entering through the edges of the tray, which allows more GCFs to be absorbed shown by the up arrows 408 by the hydrogel, as compared to the middle surface 405 of the hydrogel that has a higher concentration of medicament than the upper and lower surfaces of the hydrogel which have been emptied quicker.

In the embodiment of FIG. 15B, the enlarged cross-sectional view of a portion of the oral appliance 400 is illustrated with respect to the top, middle and bottom portions of the periodontal pocket being treated. In FIG. 15B, top portion 418 of the pocket is located at the gingival crest, the bottom portion 420 of the pocket is located at the bottom of the junctional epithelium and the area in between is considered the middle 419 of the periodontal pocket. In a healthy gum, the top portion 418 is about 1 mm to about 3 mm in depth down the pocket. In gum afflicted with periodontitis, the top portion 418 and the bottom portion 420 of the periodontal pocket can still be 1 mm, however, the middle portion 419 can vary depending on the depth of the pocket. As the periodontal pocket is treated the middle portion 19 shrinks in depth.

The resulting higher concentration of the middle surface of the hydrogel allows the middle surface to have better medicament delivery ability as compared to the upper and lower surfaces that have a lower concentration of medicament. These upper and lower surfaces may have, in some embodiments, better wicking ability to wick contaminating fluid away from the pocket, while the middle surface has better medicament delivery ability. The hydrogel is placed in the oral appliance and it is configured to create a seal at the entrance of the periodontal pocket so that there will be a bulge of hydrogel at the entrance to cause such a seal 413. This seal, in some embodiments, can be used to reduce or prevent medicament from staining the teeth.

In some embodiments, the oral appliance facilitates leaching of medicament into the subgingival space (e.g., the gingival sulcus or gingival crevice or periodontal pocket) by enhancing pressure gradients, diffusion, and capillary action. This maintains an effective concentration of medicament in the periodontal pocket to treat the disease.

Oral Appliance Materials

The oral appliance can be made of any materials that can hold and release the medicament. In various embodiments, the material from which the oral appliance can be made from includes swellable polymers, such as, for example hydrogels, gels, polymer brushes or combinations thereof.

In some embodiments, suitable polymers for use to make the oral appliance include, for example, polyacrylates, polyamide-imide, phenolic, nylon, nitrile resins, petroleum resins, fluoropolymers, copolyvidones (copovidones), epoxy, melamine-formaldehyde, diallyl phthalate, acetal, coumarone-indene, acrylics, acrylonitrile-butadiene-styrene, alkyds, cellulosics, polybutylene, polycarbonate, polycaprolactones, polyethylene, polyimides, polyphenylene oxide, polypropylene, polystyrene, polyurethanes, polyvinyl acetates, polyvinyl chloride, poly(vinyl alcohol-co ethylene), styrene acrylonitrile, sulfone polymers, saturated or unsaturated polyesters or combinations thereof.

In some embodiments, the polymer comprises, consists essentially of or consists of an amount from about 5% to about 100% by weight, from about 5%, 10%, 15%, 20%, 25%, 30%, 35%, 40%, 45%, 50%, 55%, 60%, 65%, 70%, 75%, 80%, 85%, 90%, 95% to about 100% by weight, from about 10% to about 15% by weight, from about 15% to about 20% by weight, from about 20% to about 25% by weight, from about 25% to about 30% by weight, from about 30% to about 35% by weight, from about 35% to about 40% by weight, from about 40% to about 45% by weight, from about 45% to about 50% by weight, from about 50% to about 55% by weight, from about 55% to about 60% by weight, from about 60% to about 65% by weight, from about 65% to about 70% by weight, from about 70% to about 75% by weight, from about 75% to about 80% by weight, from about 80% to about 85% by weight, from about 85% to about 90% by weight, from about 90% to about 95% by weight, or from about 95% to about 100% by weight of the oral appliance. In some embodiments, the oral appliance is substantially all polymer from about 80% to about 99.9% by weight. The medicament comprises, consists essentially of or consists of an amount from about 0.01% to about 50%, from about 0.1% to about 20% by weight, from about 0.5% to about 10%, or from about 1% to about 7% by weight of the oral appliance.

In various embodiments, the molecular weight of the polymer can be a wide range of values. The average molecular weight of the polymer can be from about 1000 to about 10,000,000 g/mol; or about 1,000 to about 1,000,000; or about 5,000 to about 500,000; or about 10,000 to about 100,000; or about 20,000 to about 50,000 g/mol.

In some embodiments, when the oral appliance is made from one polymer, the density of the polymer can vary such that the non-porous and porous regions are formed in the oral appliance from a single material.

In some embodiments, when different molecular weight polymers are used, the polymer can be dense and have a higher molecular weight such that the polymer is non-porous. In some embodiments, the polymer can be less dense and have a lower molecular weight such that the polymer is porous. In some embodiments, the oral appliance can be made from multiple polymers, as described above. The multiple polymers can have the same or different densities. The polymers can have an average molecular weight of from about 1000 to about 10,000,000 g/mol; or about 1,000 to about 1,000,000; or about 5,000 to about 500,000; or about 10,000 to about 100,000; or about 20,000 to about 50,000 g/mol.

The polymer can have a modulus of elasticity (Young's modulus) in the range of about $1 \times 10^{-2}$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

The polymer may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethyl methacrylate), poly-(methoxyethyl methacrylate), poly(methoxyethoxyethyl methacrylate), polymethylmethacrylate (PMMA), methyl methacrylate (MMA), gelatin, polyvinyl alcohols, propylene glycol, mPEG, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, the polymer can comprise a hydrogel that is or is not infused with at least one medicament. Suitable hydrogels for use in the oral appliance, include natural hydrogels, such as for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly(acrylonitrile-acrylic acid), polyurethanes, polyethylene glycol (for example, PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrolidone), acrylates such as poly(2-hydroxy ethyl methacrylate) and copolymers of acrylates with N-vinyl pyrrolidone, N-vinyl lactams, polyacrylonitrile or combinations thereof.

In some embodiments, cross-linking agents used to make the porous material non-porous include, but are not limited to, 1-hydroxycyclohexyl phenyl ketone, glutaraldehyde, formaldehyde, epoxy, compounds, dialdehyde, sodium borate/boric acid, glyoxal, oxidized dextrins, epichlorohydrin, endogen polyamine spermidine, oxidized alginate, zinc, borax, ethylene glycol dimethacrylate (EGDMA), N, N'-methylenebisacrylamide, derivatives of ethylene glycol di(meth)acrylate, derivatives of methylenebisacrylamide, formaldehyde-free crosslinking agent including N-(1-Hydroxy-2,2-dimethoxyethyl)acrylamide, or a combination thereof.

In some embodiments, it may be difficult for the medicament to move in and out of the oral appliance. In some embodiments, a porosity reducing agent such as a cross-linking agent is used to generate a non-porous region on the polymer oral appliance.

In some embodiments, the oral appliance can be transparent so that a user can see the teeth. The oral appliance may be disposable and sterilizable. In various embodiments, one or more components of the oral appliance is sterilized by radiation in a terminal sterilization step in the final packaging. Terminal sterilization of a product provides greater assurance of sterility than from processes such as an aseptic process, which require individual product components to be sterilized separately and the final package assembled in a sterile environment. Other methods may also be used to sterilize one or more components of the oral appliance, including, but not limited to, E-beam radiation, gamma radiation, gas sterilization, such as, for example, with ethylene oxide or steam sterilization.

Medicaments

The oral appliance contains one or more medicaments coated or layered on it, or impregnated within it, at the same or different areas, to form the oral appliance. The medicament can be disposed on a porous material that can be separated from the oral appliance. Alternatively, the medicament can be disposed on or in the interior of the oral appliance. In various embodiments, some areas of the polymer material of the oral appliance do not contain one or more medicaments, and the polymer material may function to hold or lock a portion of the polymer material in place so that other portions of the polymer material can contact the appropriate target site. Thus, in some embodiments, the polymer material may contain one or more medicaments disposed at discrete regions on the interior surface of the oral appliance. In other embodiments, one or more portions of the oral appliance do not contain any medicament disposed in or on it (e.g., the non-porous regions of the oral appliance). The term "medicament" as used herein is generally meant to refer to any substance that alters the physiology of a patient. The term "medicament" may be used interchangeably herein with the terms "medicine", "medication", "drug" "therapeutic agent", "therapeutically effective amount", or "active pharmaceutical ingredient". It will be understood that a "medicament formulation" may include more than one therapeutic agent, wherein exemplary combinations of therapeutic agents include a combination of two or more medicaments. The medicament can also include cells, where the device (e.g., oral appliance) can be seeded with the cells, for example, gingival cells or gingival tissue, bone cells, cartilage cells or bone tissue so that the device can repair or replace tissue in the treatment area. Other bacterial or other life forms in toto or in part(s) may also be loaded as well as bacterial phages.

The medicament may be in powder, liquid, solid, solution, or suspension (e.g., gel) form and disposed on or impregnated in the oral appliance. This may occur during manufacture of the oral appliance or it may occur after the oral appliance is made. For example, on the core polymer material of the oral appliance, the medicament may be layered by solution or suspension layering or powder layering techniques. In solution or suspension layering, the medicament and any inactive ingredients (excipients, binders, etc.) are suspended or dissolved in water or an organic solvent. The resulting liquid is sprayed onto the outside of the oral appliance to make the polymer material have the desired potency. Solution or suspension layering may be conducted using a wide variety of process techniques, for example, by fluidized bed, Wurster bottom spray techniques, or the like. When the desired potency has been achieved, the polymer material is dried to the desired residual moisture content. Powdered layering involves the application of a dry powder to the oral appliance. The powder may contain the drug, or may include excipients such as a binder, flow aid, inert filler, and the like. In the powder layering technique, a pharmaceutically acceptable liquid, which may be water, organic solvent, with or without a binder and/or excipient, is applied to the oral appliance while applying the dry powder until the desired potency is achieved. When the desired potency has been achieved, the oral appliance may be dried to the desired moisture content.

In various embodiments, the medicament is in liquid form and is capable of diffusing through and within the polymer material. In various embodiments, the liquid medicament may flow or diffuse from one portion of the oral appliance to another portion. In some embodiments, the liquid medicament may not flow or diffuse within the oral appliance. In some embodiments, the liquid medicament is confined within the regions of the oral appliance corresponding to the treatment area. The liquid medicament is not capable of flowing or diffusing into the non-porous regions of the oral appliance. In some embodiments, the liquid medicament may flow or diffuse into the non-porous regions; however, the medicament cannot easily flow or diffuse out of the non-porous regions. In various aspects, the medicament located at discrete regions in the interior surface of the oral appliance is free of hydrogen peroxide.

Examples of medicaments include, but are not limited to, anti-inflammatory agents, antimicrobial agents (e.g., antiviral, antibacterial, antibiotic, antifungal agents, etc.), antiseptic, tissue and bone growth factors, pain management medication (e.g., analgesics, anesthetics, etc.), tooth whitening agents, breath fresheners, anticalculus agents, antiseptics, anticaries agents, nutrients, vitamins, minerals, herbal products, probiotics, immunologic agents, astringents, an ointment or liniment or mixtures thereof.

Suitable anti-inflammatory agents to treat and/or reduce inflammation include steroidal and/or non-steroidal anti-inflammatories. Exemplary anti-inflammatory agents include by way of example and not limitation, alclofenac; alclometasone dipropionate; algestone acetonide; alendronate sodium; alpha amylase; amcinafal; amcinafide; amcinonide; amfenac sodium; amiprilose hydrochloride; anakinra; anirolac; anitrazafen; apazone; balsalazide disodium; beclomethasone diproprionate; bendazac; benoxaprofen; benzydamine hydrochloride; betamethasone; bromelains; broperamole; budesonide; carprofen; cicloprofen; cintazone; cliprofen; clobetasol propionate; clobetasone butyrate; clopirac; cloticasone propionate; cormethasone acetate; cortisone acetate; cortodoxone; deflazacort; desonide; desoximetasone; dexamethasone dipropionate; diclofenac potassium; diclofenac sodium; diflorasone diacetate; diflumidone sodium; diflunisal; difluprednate; diftalone; dimethyl sulfoxide; drocinonide; endrysone; enlimomab; enolicam sodium; epirizole; etodolac; etofenamate; felbinac; fenamole; fenbufen; fenclofenac; fenclorac; fendosal; fenpipalone; fentiazac; flazalone; fluazacort; fludrocortisone; flufenamic acid; flumizole; flunisolide acetate; flunixin; flunixin meglumine; fluocinonide; fluocinolone acetonide; fluocortin butyl; fluorometholone acetate; fluquazone; flurandrenolide; flurbiprofen; fluretofen; fluticasone propionate; furaprofen; furobufen; halcinonide; halobetasol propionate; halopredone acetate; hydrocortisone; ibufenac; ibuprofen; ibuprofen aluminum; ibuprofen piconol; ilonidap; indomethacin; indomethacin sodium; indoprofen; indoxole; intrazole; isoflupredone acetate; isoxepac; isoxicam; ketoprofen; lofemizole hydrochloride; lomoxicam; loteprednol etabonate; meclofenamate sodium; meclofenamic acid; meclorisone dibutyrate; medrysone; mefenamic acid; mesalamine; meseclazone; methylprednisolone suleptanate; momiflumate; nabumetone; naproxen; naproxen sodium; naproxol; nimazone; nilutamide; olsalazine sodium; orgotein; orpanoxin; oxaprozin; oxyphenbutazone; pamidronate disodium; paramethasone; paranyline hydrochloride; pentosan polysulfate sodium; phenbutazone sodium glycerate; pirfenidone; piroxicam; piroxicam cinnamate; piroxicam olamine; pirprofen; prednazate; prednisolone; prifelone; prodolic acid; proquazone; proxazole; proxazole citrate; rimexolone; romazarit; salcolex; salnacedin; salsalate; sanguinarium chloride; seclazone; sermetacin; sudoxicam; sulindac; suprofen; talmetacin; talniflumate; talosalate; tebufelone; tenidap; tenidap sodium; tenoxicam; tesicam; tesimide; tetrydamine; tiopinac; tixocortol pivalate; tolmetin; tolmetin sodium; triamcinelone; triclonide; triflumidate; zidometacin; zomepirac sodium or combinations thereof.

Anti-inflammatory agents include steroidal agents or glucocorticosteroids. Phospholipase A2 ("PLA2") is a lipolytic enzyme that has been implicated as a possible mediator of inflammation. Specifically, PLA2 hydrolyses the 2-acyl position of glycerophospholipids, liberating free-fatty acids, mainly arachidonic acid. Subsequently, it is believed that arachidonic acid is converted into a variety of proinflammatory cicosanoids. Glucocorticosteroids are known to stop or reduce the suggested mechanisms of inflammation that involves the activation of the arachidonic acid cascade, which results in the liberation of a variety of proinflammatory eicosanoids by inducing lipocortin that inhibits PLA2. This provides a significant advantage over non-steroidal anti-inflammatory agents that enter the cascade much later.

Suitable glucocorticosteroids include, but are not limited to, alclometasone diproprionate, alendronate sodium, amcinonide, beclomethasone diproprionate, betamethasone, budesonide, clobetasol propionate, cortisone, dexamethasone, diflorasone diacetate, hydrocortisone, fludrocortisone; flunisolide acetate, fluocinolone acetonide, fluocinonide, fluorometholone acetate, flurandrenolide, halcinonide, medrysone; methylprednisone suleptanate, pamidronate, paramethasone, prednisolone, nilutamide, triamcinelone, or combinations thereof.

Dexamethasone is of particular interest for use as an anti-inflammatory to treat orofacial diseases. Besides its anti-inflammatory property, dexamethasone can be delivered to up-regulate certain enzyme activities. Specifically, dexamethasone can be used to increase or up-regulate alkaline phosphotase activity in regenerating human periodontal cells.

Exemplary anti-infective agents to treat infection include by way of example and not limitation, antibacterial agents; quinolones and in particular fluoroquinolones (e.g., norfloxacin, ciprofloxacin, lomefloxacin, ofloxacin, levofloxacin, delafloxacin, etc.), aminoglycosides (e.g., gentamicin, tobramycin, etc.), glycopeptides (e.g., vancomycin, etc.), lincosamides (e.g., clindamycin), cephalosporins (e.g., first, second, third generation) and related beta-lactams, macrolides (e.g., azithromycin, erythromycin, clarithromycin, etc.), nitroimidazoles (e.g., metronidazole), penicillins, polymyxins, tetracyclines, triamcinolone, triclosan or combinations thereof.

Other exemplary antibacterial agents include, by way of illustration and not limitation, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbapenem, carbenicillin disodium; carbenicillin indanyl sodium; carbenicillin phenyl sodium; carbenicillin potassium; carumonam sodium; cefaclor, cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; monobactams; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl;

sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

Exemplary analgesics include, but are not limited to, acetaminophen; alfentanil hydrochloride; aminobenzoate potassium; aminobenzoate sodium; anidoxime; anileridine; anileridine hydrochloride; anilopam hydrochloride; anirolac; antipyrine; aspirin; benoxaprofen; benzydamine hydrochloride; bicifadine hydrochloride; brifentanil hydrochloride; bromadoline maleate; bromfenac sodium; buprenorphine hydrochloride; butacetin; butixirate; butorphanol; butorphanol tartrate; carbamazepine; carbaspirin calcium; carbiphene hydrochloride; carfentanil citrate; ciprefadol succinate; ciramadol; ciramadol hydrochloride; clonixeril; clonixin; codeine; codeine phosphate; codeine sulfate; conorphone hydrochloride; cyclazocine; dexoxadrol hydrochloride; dexpemedolac; dezocine; diflunisal; dihydrocodeine bitartrate; dimefadane; dipyrone; doxpicomine hydrochloride; drinidene; enadoline hydrochloride; epirizole; ergotamine tartrate; ethoxazene hydrochloride; etofenamate; eugenol; fenoprofen; fenoprofen calcium; fentanyl citrate; floctafenine; flufenisal; flunixin; flunixin meglumine; flupirtine maleate; fluproquazone; fluradoline hydrochloride; flurbiprofen; hydromorphone hydrochloride; ibufenac; ibuprofen; indoprofen; ketazocine; ketorfanol; ketorolac and ketorolac tromethamine; letimide hydrochloride; levomethadyl acetate; levomethadyl acetate hydrochloride; levonantradol hydrochloride; levorphanol tartrate; lidocaine, bupivacaine, lofemizole hydrochloride; lofentanil oxalate; lorcinadol; lomoxicam; magnesium salicylate; mefenamic acid; menabitan hydrochloride; meperidine hydrochloride; meptazinol hydrochloride; methadone hydrochloride; methadyl acetate; methopholine; methotrimeprazine; metkephamid acetate; mimbane hydrochloride; mirfentanil hydrochloride; molinazone; motrin; morphine sulfate; moxazocine; nabitan hydrochloride; nalbuphine hydrochloride; nalmexone hydrochloride; namoxyrate; nantradol hydrochloride; naproxen; naproxen sodium; naproxol; nefopam hydrochloride; nexeridine hydrochloride; noracymethadol hydrochloride; ocfentanil hydrochloride; octazamide; olvanil; oxetorone fumarate; oxycodone; oxycodone hydrochloride; oxycodone terephthalate; oxymorphone hydrochloride; pemedolac; pentamorphone; pentazocine; pentazocine hydrochloride; pentazocine lactate; phenazopyridine hydrochloride; phenyramidol hydrochloride; picenadol hydrochloride; pinadoline; pirfenidone; piroxicam olamine; pravadoline maleate; prodilidine hydrochloride; profadol hydrochloride; propiram fumarate; propoxyphene hydrochloride; propoxyphene napsylate; proxazole; proxazole citrate; proxorphan tartrate; pyrroliphene hydrochloride; remifentanil hydrochloride; salcolex; salethamide maleate; salicylamide; salicylate meglumine; salsalate; sodium salicylate; spiradoline mesylate; sufentanil; sufentanil citrate; talmetacin; talniflumate; talosalate; tazadolene succinate; tebufelone; tetrydamine; tifurac sodium; tilidine hydrochloride; tiopinac; tonazocine mesylate; tramadol hydrochloride; trefentanil hydrochloride; trolamine; veradoline hydrochloride; verilopam hydrochloride;

volazocine; xorphanol mesylate; xylazine hydrochloride; zenazocine mesylate; zomepirac sodium; zucapsaicin or combinations thereof.

Antifungal agents that can be used in the oral appliance include, but are not limited to, nystatin, clotrimazole, griseofulvin, ketoconazole, itraconazole, fluconazole, terbinafine, or a combination thereof.

Exemplary antiseptics include chlorhexidine, chlorhexidine gluconate, chlorhexidine acetate, chlorhexidine hydrochloride, hexetidine, hydrogen peroxide, sodium hypochlorite, cetylpyridinium chloride, triclosan, methyl salicylate, povidone-iodine and the like. Astrigents, for example, zinc chloride are also useful medicaments for the oral appliances described in this disclosure.

Oral appliances are provided that can deliver medicaments and/or tissues to at least a portion of the teeth and/or soft tissues inside the oral cavity in a three-dimensional way. One advantage of the oral appliance is that it is custom made to fit only one patient. As used herein a "custom fit" oral appliance refers to an oral appliance prepared to correspond to at least a portion of the teeth or all of the teeth and soft tissues of a specific patient. Typically, the custom fit appliance is prepared by a dental care professional (e.g., dentist, oral surgeon, medical doctor, other health care professional, technician, manufacturer, etc.). The custom fit oral appliance can be made from an impression mold or using an analog or digital image capturing device. The oral appliance provided by this disclosure is not a boil-and-bite prefabricated device or a stock oral appliance, which can be manipulated by the consumer himself/herself with fingers to shape it against the teeth and gums but which cannot possibly be shaped to properly align the medication with the proper geographic anatomy.

In some embodiments, the oral appliance can contain medicament separately in a cargo area or sponge or placed as a liquid in the oral appliance. The oral appliances disclosed herein are custom fit, disposable, and manufactured in one continuous step, pre-loaded with medicament in or on at least a portion of the interior and/or exterior surfaces of the appliance and can deliver medicaments or graft tissues three dimensionally. In some embodiments, the oral appliance can be transparent. Still another advantage of the oral appliance is that, in various embodiments, it can be easily manufactured and is comfortable for the patient to use. Other advantages of the oral appliances provided by this disclosure include greater efficacy over conventional oral therapies based on two dimensional systems, user convenience, enhanced patient compliance, lower dosage requirements, less dilution of medicament and enhanced applied pressure to gums.

In one embodiment, there is an oral appliance for delivering a medicament to at least a portion of teeth and/or soft tissue areas inside an oral cavity, the oral appliance comprising an interior surface having a medicament disposed in or on at least a portion of and/or all of the interior surface of the oral appliance, the interior surface being formed to fit contours of at least the portion of the teeth and/or soft tissue, including inflamed soft tissue areas inside the oral cavity and being configured for holding the medicament in contact with at least the portion of the teeth and/or soft tissue areas inside the oral cavity to deliver the medicament thereto.

The soft tissue of the inside of the mouth includes, but is not limited to, any soft tissue adjacent or between the teeth including, but not limited to, the papilla, tissue of the upper and lower dental arches, marginal gingiva or gingival margin, gingival sulcus, inter-dental gingiva, gingival gum structure on lingual and buccal surfaces up to and including the muco-gingival junction and/or the upper palate and/or the floor of the mouth.

In various embodiments, the soft tissue area inside the oral cavity includes the muco-buccal folds, hard and soft palates, lining mucosa, the tongue (one or all surfaces of the tongue) and/or attached gingival tissue, all of which may occasionally become inflamed as caused by any number of conditions. In various embodiments, the oral appliance receives one or more teeth including one or more molars, premolars, incisors, cuspids, tooth implant, or combination or portions thereof. In other embodiments, the medicament contained in the oral appliance can be disposed anywhere in or on the interior or exterior surface of the oral appliance adjacent to the gum and/or other soft tissue areas of the oral cavity including the front, back, occlusal surfaces of one or more teeth.

In various embodiments, the oral appliance may contain more than one medicament. However, in another embodiment, combination therapy will involve use of a single, safe and effective amount of the medicament. For example, the method may further comprise subsequently administering one or more additional oral appliances, each containing a medicament that is different from the medicament contained in the earlier oral appliance. In this way, a series of customized treatment regimens can be provided to the patient. This provides for a "mix and match" medicament regimen with dose adjustment capability and provides the added advantage of allowing the health professional complete control to administer only those medicaments at the desired strength believed to be appropriate for the disease or condition being treated to a particular individual.

In some embodiments, one or more oral appliances can be administered to a patient to treat inflammation and/or pain or other conditions associated with inflammation.

The amount of medicament contained within the oral appliance, will vary widely depending on the effective dosage required and rate of release from the polymer material and the length of the desired delivery interval. The dosage administered to the patient can be single or multiple doses and will vary depending upon a variety of factors, including the agent's pharmacokinetic properties, patient conditions and characteristics (sex, age, body weight, health, size, etc.), extent of symptoms, concurrent treatments, frequency of treatment and the effect desired. These factors can readily be determined by those of ordinary skill in the art.

In various embodiments, the polymer material of the oral appliance is designed to release the medicament as a bolus dose of the medicament, a single dose of the medicament, or multiple doses of the medicament all preloaded with a specific dosage at the manufacturing facility.

In some embodiments, the medicament described herein is in the oral appliance in an amount of from about 0.01, 0.02, 0.03, 0.04, 0.05, 0.06, 0.07, 0.08, 0.09, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, to about 50% by weight of the oral appliance.

In some embodiments, when the medicament is in liquid form, the polymer oral appliance is submerged in the liquid medicament. The polymer oral appliance will then absorb the liquid medicament into the porous material of the oral appliance. In some embodiments, the medicament and the polymer material are mixed together, and the mixture is made into the oral appliance. In some embodiments, the oral appliance has a non-porous coating disposed on selected areas of the oral appliance that is impenetrable by the liquid medicament. In some embodiments, some portions of the oral appliance comprise non-porous materials that are impenetrable by the medicament.

In some embodiments, the medicament can be disposed anywhere in or on the interior or exterior surface of the oral appliance adjacent to the gum and/or other soft tissue areas of the oral cavity including the front, back, occlusal surfaces of one or more teeth, including any inflamed tissue inside the oral cavity. Some portions of teeth that do not require the medicament are sealed with the non-porous material which can be a coating, cross-linked with porosity reducing agent or comprise non-porous material such that the medicament cannot penetrate said portions. In some embodiments, the medicament may be disposed in or may enter the non-porous region. However, the medicament disposed in the non-porous region will not release the medicament or will release the medicament at a reduced rate.

In some embodiments, the medicament may enter the non-porous regions, but the medicament will release slowly from these regions. For example, the medicament can be disposed at discrete non-porous regions adjacent to the treatment area or uniformly disposed throughout the device. In this example, the medicament will not be released to other regions that do not correspond with the treatment area, for example, inflamed tissue inside the oral cavity.

In some embodiments, the medicament may flow into the non-porous regions but the medicament in the non-porous regions will release the medicament at a slower rate than that of the porous regions. As the interior and/or exterior surface of the oral appliance contacts the oral cavity, the medicament is released from the polymer such that all or parts of the oral appliance will degrade over time by the action of enzymes, by hydrolytic action and/or by other similar mechanisms in the oral cavity. In various embodiments, the degradation can occur either at the surface of the oral appliance at discrete positions (heterogeneous or surface erosion) or uniformly throughout the oral appliance (homogeneous or bulk erosion). In some embodiments, all or discrete portions of the interior surface will degrade and release medicament at or near the target site in the oral cavity. The oral appliance will cover at least a portion of the teeth and or gums, by applying the device over axis to cover the area of the teeth and or gums, and the oral appliance will be adjacent to the gingival sulcus or other soft tissue or hard tissue areas, which will allow the medicament, if desired, to be released from the polymer to these areas.

Probiotics

In some embodiments, the oral appliance can contain a probiotic at discrete regions of the oral appliance. Probiotics are beneficial agents that can be used to repopulate the flora or the oral microbiome with microbes. Probiotics, which are healthy microorganisms that can be ingested, may help to improve oral health. Probiotics, which are defined as live microbes that confer health benefits to a host when consumed in sufficient quantities, may offer a low-risk, easy-to-use treatment option for periodontal diseases.

Probiotics are referred to as living microorganisms, principally bacteria, that are safe for humans and have beneficial effects on human health. Oral probiotics maintain a balanced oral microbiome, which can prevent cavity development, maintain fresh breath, and keep gum disease at bay.

Good bacteria may help reduce plaque, which is a source of cavities and gum disease such as gingivitis and periodontitis. A selection of probiotics includes, in some aspects, *Bifidobacterium longum, Lactobacillus plantarum, Bifidobacterium bifidum, Lactobacillus casei,* and *Lactobacillus acidophilus, Lactobacillus salivarius, Lactobacillus sporo-*

*genes* or a blend thereof can be placed at discrete regions in the interior surface of the oral appliance described in this disclosure where the probiotics come into contact with a top portion of the inflamed tissue inside the oral cavity. In other optional embodiments, the oral appliance is configured to contact the middle portion or mid-level portion or the bottom portion of the inflamed tissue inside the oral cavity. Unlike a lozenge or a mouthwash containing probiotics, which immediately get diluted by saliva and other oral fluids and are dispersed throughout the mouth and swallowed, the probiotics used in the oral appliances of this disclosure have an immediate and sustained high contact maintaining a high concentration with the specific targeted inflamed or treated tissue that has been depleted of microbes present in a healthy microbiome. In various embodiments, the probiotics can be grown at discrete regions in the interior surface of the oral appliance.

The blend of probiotics can contain approximately equal parts of each of the species. In some embodiments, the colony forming unit (CFU) of the probiotic blend should range from approximately 100,000 CFUs to about 6,000,000,000 CFUs per tablet, from approximately 20,000 CFUs for each species to about 1,200,000,000 CFUs for each species. In other embodiments, the probiotic blend should range from approximately 2,000,000,000 CFUs per tablet to approximately 500,000,000 CFUs for each species.

In other embodiments, exemplary probiotics useful for treatment of chronic periodontitis with the oral appliances described in this disclosure include without limitations, *Lactobacillus brevis, Lactobacillus salivarius, Lactobacilus reuteri, Lactobacillus acidophilus, Lactobacillus rhamnosus, L. sporogens* or a blend thereof.

In some aspects, ATCC 55730 and ATCC PTA 5289, $1\times10^8$ CFU of *L. reuteri*, placed at discrete hydrogel regions inside the surface of the oral appliance and applied to inflamed tissue inside the oral cavity of patients suffering from gingivitis twice a day for 10 minutes for a period of 3 weeks can reduce the production of pro-inflammatory cytokines while promoting regulatory T cell development and function and decrease bleeding on probing of the inflamed gums. Additionally, the probiotics can be seeded on either the inside or outside or both so as to allow the timed release of said microbes to populate the entire gastro-intestinal tract.

In other embodiments, CD2, $1\times10^9$ CFU *Lactobacillus brevis* is used three times a day for 2 weeks in the oral trays described in this disclosure on gums afflicted with gingivitis. It is found the probiotic reduced the inflammation and bleeding of the gums.

In another embodiment, DSM 17938 and ATCC PTA 5289, $1\times10^8$ CFU of *L. reuteri*, placed at discrete hydrogel regions inside the surface of the oral appliance is applied to inflamed tissue inside the oral cavity of patients suffering from periodontitis twice a day for 10 minutes for a period of 12 weeks can reduce plaque index, gingival index, bleeding on probing, the periodontitis pocket depth and attachment gain to the tooth is also observed. In another embodiment, WB 21, $6.7\times10^8$ CFU *Lactobacillus salivarius*, placed at discrete hydrogel regions inside the surface of the oral appliance of this disclosure is applied to inflamed tissue inside the oral cavity of patients suffering from periodontitis every day for 10 minutes for a period of 8 weeks can reduce plaque index, gingival index, bleeding on probing, the periodontitis pocket depth and attachment gain to the tooth is also observed. Similar tests are conducted with KJ3 *Streptococcus oralis*, KJ2 *Streptococcus uberis*, and JH145, $1\times10^8$ CFU *Streptococcus rattus* on patients suffering from chronic periodontitis. The oral appliance containing these probiotics is applied once a day for 3 or 6 months resulting in a significantly lower plaque index at the 12- or 24-week evaluation.

Finally, non-limiting examples of strains of the probiotic microorganisms suitable for use in the oral appliance according to the present disclosure may include, but are not limited to, *Lactococcus lactis* NCC2211, *Lactobacillus rhamnosus GG, ATCC53103* (LGG), *Bifidobacterium longum* BB536, *Lactobacillus delbrueckii* subspecie *Bulgaricus* 2038, *Streptococcus salivarius* subsp *Thermophilus* 1131, *Lactobacillus casei* Shirota, *Bifidobacterium breve* Yakult, *Bifidobacterium lactus* FK120, *Bifidobacterium lactis* LKM512, *Lactobacillus acidophilus* CK92, *Lactobacillus acidophilus* La5, *Lactobacillus herbeticus* CK60, *Lactobacillus casei* SBR1202, *Lactobacillus paracasei* F19, *Lactobacillus paracasei* F19, *Lactobacillus paracasei* DSMZ16671, *Lactobacillus gaseeri* SP, *Lactobacillus salivarius* W24, *Bifidobacterium* SP, *Lactobacillus casei* NY1301, *Lactobacillus* LC1, *Bifidobacterium lactis* Bb-12, *Lactobacillus reuteri* ATCC PTA 6475, *Lactobacillus lactis* NCC221, *Streptococcus* thermophiles NCC1561, *Streptococcus Salivarius* Mia, *Saccharomyces boulardii*, *Lactobacillus rhamnosus* GG, *Lactobacillus plantarum* 299v, *Lactobacillus reuteri* PTA 5289, *Lactobacillus reuteri* SD2112, and combinations thereof.

Without wishing to be bound by any particular theory, it is contemplated that the probiotic microorganisms used in the oral appliances of this disclosure may have beneficial effects on the oral environment by controlling colonization of cariogenic streptococci, *Candida albicans*, and other harmful microflora. Although the biochemical mechanism by which this occurs is not fully understood, it is contemplated that the probiotic microorganisms used in the present disclosure may provide beneficial effects by reducing bacterial adhesion, modulating the surrounding pH, and producing antibacterial agents to restore the microbiome of the oral cavity.

For example, when introduced into the oral cavity, the disclosed probiotic microorganisms may, reduce the number of bacteria or harmful biofilms present in the oral cavity, may decrease gum bleeding, gingivitis, and plaque formation, may induce remission of chronic symptoms of periodontitis in the inflamed tissues of the oral cavity.

Methods of Making the Oral Appliance

The oral appliance is custom made to fit a specific patient. The custom-made oral appliance may be prepared by a dental care professional including, but not limited to a dentist, oral surgeon, medical doctor, health care provider or technician or manufacturer. The oral appliance can be made from an impression mold, or by using an analog or digital image capturing device. The oral appliance disclosed herein is not a boil and bite prefabricated device or a stock tray which can be manipulated by the consumer himself/herself with fingers to shape it against the teeth and gums. The oral appliance disclosed herein is custom fit, disposable, and monolithic that is pre-loaded with medicament in or on at least a portion of the porous interior and/or porous exterior surfaces of the appliance and can deliver medicaments. The medicament can be pre-loaded as part of the oral appliance or infused into the polymer of the oral appliance after the oral appliance is made.

The processes described herein can produce oral appliances with a variety of different properties. Hence in some embodiments the oral appliances are rigid; in other embodiments the products are flexible or resilient. In some embodiments, the oral appliances are a solid; in other embodiments, the oral appliances are a gel such as a hydrogel or have layers of such. In some embodiments, the oral appliances have a shape memory (that is, return substantially to a previous shape after being deformed, so long as they are not deformed to the point of structural failure).

3D Printing of Oral Appliance

In one embodiment, a computer-implemented system for producing an oral appliance by 3D printing or additive manufacturing is provided, as shown in FIG. 16. In this embodiment, an input device or is used to scan the oral cavity of and thus generate a digital record of the patient's mouth. The scanner can be an MRI scanner, a CT scanner, a PET scanner, a digital scanner, an X-Ray machine, or an intra-oral scanner, magnetic resonance imaging (MRI) scanner, coordinate measuring machine, destructive scanner or ultrasound scanner for example. In various embodiments, the scanner can scan the patient's teeth, soft tissue, or both to obtain a digital data set of the teeth and/or soft tissue areas inside the mouth from which is generated. The digital data can be stored in a database, such as for example a computer that has a processor 62, which sends the digital data to its memory 64 and/or can display it in a virtual 3D image display 66 of the processor. The database and/or processor can comprise an input device (e.g., keyboard, touch screen, voice activation, etc.) to allow a user to enter, display, edit, and/or transmit data. The input device can control the print heads being used, the print density of the printer head, the type of polymer being used, and whether one, two, or more print heads with different polymer weights to make the porous and/or non-porous material is used. The processor comprises logic to execute one or more instructions to carry instructions to the computer system (e.g., transmit instructions to a 3D printer 68). The logic for executing instructions may be encoded in one or more tangible media for execution by the processor. For example, the processor may execute codes stored in a computer-readable medium such as the memory. The computer-readable medium may be, for example, electronic (e.g., RAM (random access memory), ROM (read-only memory), EPROM (erasable programmable read-only memory)), magnetic, optical (e.g., CD (compact disc), DVD (digital video disc)), electromagnetic, semiconductor technology, or any other suitable medium.

In various embodiments, an authorized user can input, edit data and approve or prescribe a treatment plan. This can be displayed at the user interface of the computer processor and/or another treating computer networked with the computer processor. Although the components of the system of FIG. 16 are shown as separate, they may be combined in one or more computer systems. Indeed, they may be one or more hardware, software, or hybrid components residing in (or distributed among) one or more local or remote computer systems. It also should be readily apparent that the components of the system as described herein may be merely logical constructs or routines that are implemented as physical components combined or further separated into a variety of different components, sharing different resources (including processing units, memory, clock devices, software routines, logic commands, etc.) as required for the particular implementation of the embodiments disclosed. Indeed, even a single general-purpose computer (or other processor-controlled device) executing a program stored on an article of manufacture (e.g., recording medium or other memory units) to produce the functionality referred to herein may be utilized to implement the illustrated embodiments. It also will be understood that a plurality of computers or servers can be used to allow the system to be a network based system having a plurality of computers linked to each other over the network or Internet or the plurality of computers can be connected to each other to transmit, edit, and receive data via cloud computers.

The computer (e.g., memory, processor, storage component, etc.) may be accessed by authorized users. Authorized users may include at least one dentist or dental specialist, dental hygienist, oral surgeon, physician, surgeon, nurse, patient, and/or health care provider, manufacturer, etc. The authorized user may, in some embodiments, be artificial intelligence or machine intelligence, configured to perform tasks such as visual perception, and decision-making. The artificial intelligence can control the computer that can manufacture the device, or the artificial intelligence can manufacture the device directly.

The term "processing device" as used herein is intended to include any processor, such as, for example, one that includes a CPU (central processing unit) and/or other forms of processing circuitry. Further, the term "processing device" may refer to more than one individual processor. The term "memory" is intended to include memory associated with a processor or CPU, such as, for example, RAM (random access memory), ROM (read only memory), a fixed memory device (for example, hard drive), a removable memory device (for example, diskette), a flash memory and the like. In addition, the display device(s), input device(s), cursor control device(s), signal generation device(s), etc., can be collectively referred to as an "input/output interface," and is intended to include one or more mechanisms for inputting data to the processing device(s), and one or more mechanisms for providing results associated with the processing device(s). Input/output or I/O devices including but not limited to keyboards (e.g., alpha-numeric input device (s), display device(s), and the like) can be coupled to the system either directly (such as via bus) or through intervening input/output controllers (omitted for clarity).

In an integrated circuit implementation of one or more embodiments of the disclosure, multiple identical die are typically fabricated in a repeated pattern on a surface of a semiconductor wafer. Each such die may include a device described herein and may include other structures and/or circuits. The individual dies are cut or diced from the wafer, then packaged as integrated circuits. One skilled in the art would know how to dice wafers and package die to produce integrated circuits. Any of the exemplary circuits or method illustrated in the accompanying figures, or portions thereof, may be part of an integrated circuit. Integrated circuits so manufactured are considered part of this specification. Suitable 3D printing technology is described in U.S. Pat. No. 9,649,182, to Peter J. Zegarelli, filed Jun. 18, 2015. The entire disclosure of this patent is herein incorporated by reference into the present disclosure.

In some embodiments, methods, systems and apparatuses for the generally continuous production of a three-dimensional oral appliance are provided. In these methods, systems and apparatuses, the three-dimensional oral appliance can be produced from a liquid interface, which is often referred to as "continuous liquid interphase printing", which are suitable methods, systems and apparatuses for making the oral appliance. Suitable operation parameters for the continuous production of the oral appliance using 3D printing technology is described in U.S. Pat. No. 9,205,601 assigned to Carbon3D, Inc. The entire disclosure of this patent is herein incorporated by reference into the present disclosure.

In some embodiments, a method of manufacturing an oral appliance is provided, as shown in FIG. 16A. First, a patient's teeth are scanned (200) into a set of digital data, which shows the layout of the patient's teeth and soft tissues. The scanned image (the scan) is then used to generate a non-porous polymer oral appliance that contours the patient's teeth (202) and soft tissues. Simultaneously or at a later time, the dental practitioner identifies a region in the patient's oral anatomy where the tissue is inflamed and requires the medicament (204). A porous material is then added to this identified region (206). The porous material can be applied onto the oral appliance so that these identified regions of inflamed tissue are penetrated by the medicament. The oral appliance is then filled with medicament (208).

In various embodiments, oral appliances disclosed herein can be manufactured as more particularly described below. Generally, a patient's mouth is first ideally scanned utilizing a digital data acquisition tool. The data obtained in this manner can be used to form an initial digital record, the Base Image (BI) and that image is retained in a database. A dental professional can also obtain an initial record of the patient's oral cavity by taking an analog impression using alginate or other impression materials from which the analog model or impression will be scanned thus yielding the same BI. It is from this initial record of the patient's mouth, the Base Image (BI) that future oral appliances can be made. This image can be used as a permanent record of the patient's mouth which can then be digitally manipulated yielding a three-dimensional representation of the tissues to be treated through the platform carrier, Dig1, and for various treatment modalities, Dig2. A virtual or real oral appliance, Dig3 is thereby formed by merging the additive digital image, Dig1, with the segmentally manipulated image, Dig2, to create the final treatment image, Dig3. The Dig1 image merged with the Dig2 image creates the Dig3 image from which the oral appliance can be created.

The Base Image provides an outline of at least a portion of and/or all the surfaces of the teeth, gingiva and/or other soft tissues, which a dental practitioner may wish to treat, including a top portion, middle portion or mid-level and/or bottom portion and/or all the inflamed tissue surrounding and/or supporting the teeth inside the oral cavity. Other soft tissues of the oral cavity include without limitations, the palate, muco-buccal and muco-labial tissues, floor of the mouth, tongue, buccal and labial mucosae, and any other oral tissues. An authorized user can generate Dig1 by using software to create a layer over the teeth and gingiva which tightly approximate these tissues. The original image is now digitally enhanced to have a layer over it. Digital image Dig1 resembles a virtual oral appliance, which can be used to create a real oral appliance. Dig1 is the platform carrier from which all future appliances will be based. With respect to Dig1, the Base Image of the patient's teeth and gums has not been manipulated or modified by the computer at this point but has had a digitally represented overlay of teeth and soft tissues. The additive process can be varied such that the platform carrier (e.g., oral appliance) can be made thicker in some areas for stiffness and retention, such as over the teeth and thinner in other areas for flexibility and comfort such as over the soft tissues. The platform carrier can also vary chemically in different regions such that it may have a chemically stiffer polymer in one region and a more flexible one in another region. Or the edge of the platform carrier can have a swellable hydrogel to press against the soft tissues and thereby lock in the medications and lock out the saliva thus preventing medicament leakage out and salivary leakage in. Other chemical or elastic formulations and permutations thereof can be mixed and matched to suit a desired result. The current analog model of manufacturing may not yield these variations.

In some embodiments, Dig1 comprises the virtual image of portions of the oral appliance. By using virtual 3D imaging and 3D printing, one can utilize a gradient of physical and chemical characteristics to modify the oral appliance itself. The printer can make portions of the oral appliance thicker for stiffness or thinner for flexibility and comfort. This is programmable in the computer system. In some embodiments, the oral appliance can modulate to give stiff or flexible variations while keeping the oral appliance at a uniform thickness.

The digital image is stored in the computer readable data storage media of the computer. Computer readable media, for example, store data that is accessible by a computer, such as magnetic cassettes, flash memory cards, digital video disks, Bernoulli cartridges, random access memories (RAMs), read only memories (ROMs) or the like and may also be used in the exemplary operating environment. Computer readable media does not include signals.

Using computer software, an authorized user can next generate a second digital image referred to as Dig2. The software generating Dig2 includes points or discrete regions on the teeth and/or gingiva as boundaries corresponding to areas in the oral cavity that the dental practitioner may wish to treat, for example, the whole or parts including a top portion, middle portion or mid-level portion and/or bottom portion or apical portion of inflamed tissue surrounding and/or supporting the teeth inside the oral cavity. As used herein the "gingival margin area" comprises an area within the oral cavity, which includes the gum line and the attached gingiva, including the sulcus of the gums. The gingival margin area comprises about 2 to 3 mm of tooth above the gum line.

In some embodiments, the points or the discrete regions may include buccal surfaces of the teeth, surrounding gingival tissue, occlusal surfaces of the teeth, lingual surfaces of the teeth, and/or adjacent gingival tissue on a lingual side of the teeth, including the whole or parts of inflamed tissue including a top portion, middle portion or mid-level portion and/or bottom portion of inflamed tissue surrounding and/or supporting the teeth inside the oral cavity. Through software manipulation of the image of a patient's mouth, Dig2 can be subtracted according to point boundaries to a predetermined depth which corresponds to the desired thickness of the layer to be merged with Dig1. For example, in some embodiments, Dig2 can have a thickness layer of about 0.5 mm. The resulting Dig2 image would be as if the dental professional took a scalpel blade and precisely removed the gums or gum line to a depth of 0.5 mm and/or cut the teeth to a depth of 0.5 mm in one piece. This is a subtractive programming of virtual tissue, the slice of which is then merged precisely onto Dig1 in the exact area from which it was virtually removed. It is digital image Dig2, which holds the medicaments required to treat a selected pathology. Additionally, this segmented piece can vary in width so as to apply pressure in greater or lesser amounts to the inflamed tissues so as to facilitate healing.

In some embodiments, the medicament in the hydrogel can be specifically designed to target the pocket or crevice of the subgingival space. As treatment progresses, a plurality of scans of the oral cavity and treatment areas can be used to create Dig1, Dig2, and/or Dig3 and subsequent oral appliances can be created with medicament to target the changing dimensions of the periodontal pocket or crevice. Each subsequent series of Dig1, Dig2 and Dig3 is predicated on a new Base Image and thus cannot be mixed and matched with previous Base Images and their respective Dig1, Dig2 and Dig3 iterations.

FIG. 11 illustrates a virtual image of the polymer containing the medicament for the oral appliance. This illustrates the subtractive programming In this case the virtual 3D image 50 can be made by inputting data into the computer as to where the medicament is to be disposed at discrete regions corresponding to the treatment areas of the oral appliance. The computer system can generate the interior surface 52 of the device where medicament will be disposed in the polymer and, in some embodiments, at discrete regions adjacent to the treatment area, including the whole or parts of inflamed tissue including a top portion, middle portion or mid-level portion and/or bottom portion of inflamed tissue surrounding and/or supporting the teeth inside the oral cavity. The 3D image can be generated by subtracting from the Base Image (BI) the soft and/or hard tissues to be treated in a precise pattern, yielding an image of the targeted area, Dig2, to be merged with the original Dig1 platform device image. In some embodiments, the virtual 3D image 50 of the oral appliance will not have a floor to it 55. This is because, in some embodiments, the 3D image generated will only have the discrete regions where the medicament is to be disposed (Dig2). The remainder of the virtual image of the device can be constructed using a spatial geometric pattern 54 that can be used to add the virtual 3D image of the floor of the oral appliance and the exterior surface of the oral appliance. This includes height, width and depth to the virtual image. By utilizing the Dig2 software, a treatment system can be created in which medicaments can be delivered to targeted teeth and/or tissues in a precise three-dimensional manner. To date, previous systems for delivering medicaments to the oral cavity have been two dimensional. For example, rinses, pastes and lotions, delivered with either a finger, an applicator, toothbrushes, trays or other oral appliance system, either pre-loaded or patient loaded with medicaments, all wash or coat the teeth and/or tissues vertically and laterally. By adding the dimension of depth to the vertical and lateral dimension, an oral appliance modeled upon Dig2 can deliver medicaments also in a third dimension. The above Dig2 image is a precise subtraction of the targeted tissue accomplished through computer programming, which is then saved to be used as further described below.

Once digital image Dig1 and digital image Dig2 have been generated, they can be merged via computer modeling to generate a third and final digital image, Dig3. In this manner, a virtual platform carrier oral appliance (Dig1) generated on the Base Image (BI) can be combined with a virtual digital image of the treatment area generated including at least a portion of the periodontal pocket or crevice based on Dig2 such that the Dig2 image is precisely merged onto the Dig1 platform appliance on the inside of the Dig1 oral appliance to correspond to the exact area from which it was removed. As a result, through an additive process Dig1 can be merged with a subtractive process Dig2 to create a final computer enhanced image Dig3 which is a unique virtual three dimensional image of the oral appliance containing all or a portion of the oral appliance that contains medicament in the areas adjacent to the treatment areas including at least a portion of the periodontal pocket or crevice of the oral cavity that are unique to a given patient. In some embodiments, it is contemplated that only the surfaces of the teeth will be treated and not the gums or only the gums will be treated.

Figure 12A:
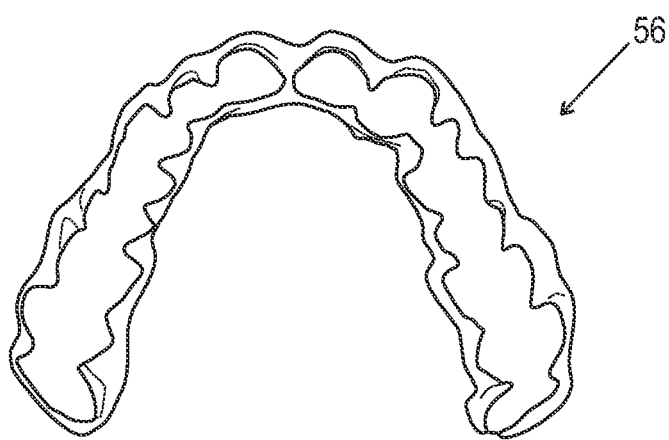
FIG. 12A illustrates an enlarged view of a virtual image (Dig2) of the regions along the sulcus (gumline) where the medicament of the oral appliance will be loaded in a polymer gel material.

FIG. 12A illustrates an enlarged view of a virtual image (Dig2) of the regions along the sulcus (gumline) 56 where the medicament of the oral appliance will be loaded in a polymer gel material.

Figure 12B:
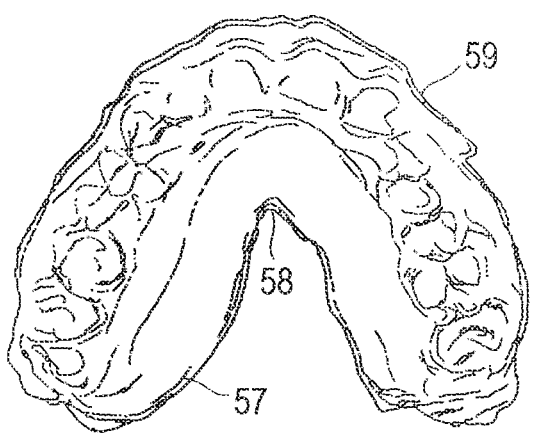
FIG. 12B illustrates an enlarged interior view of a virtual image (Dig1) of the oral appliance that is made by taking the Base Image (BI) of the oral cavity and creating a digital image that additively layers over the oral cavity including the teeth, gums, soft tissue areas and/or the palate. Dig1 does not have the virtual image of where the medicament is to be disposed.

FIG. 12B illustrates an enlarged view of a virtual image (Dig1) of the oral appliance 59 that is made by taking a baseline digital image of the oral cavity and creating a digital image that corresponds to or layers over the oral cavity including the teeth, gums, soft tissue areas and/or the palate. Dig1 does not have the virtual image of where the medicament is to be disposed. The lower portion 58 of the virtual oral appliance corresponds to and will contact portions of the tongue and hard palate 58 as well as the soft palate 57.

Figure 12C:
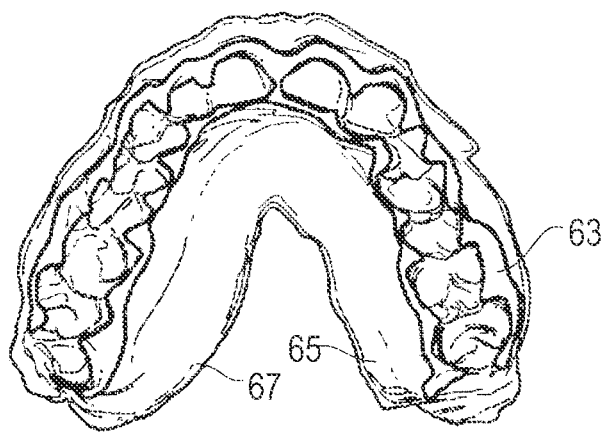
FIG. 12C illustrates an enlarged interior view of a virtual image (Dig1) of the oral appliance. The virtual image is the merging of the additive Dig1 data and the subtractive data of Dig2, from which the oral appliance can be produced that has regions along the sulcus (gumline) where the medicament of the oral appliance will be loaded in a polymer gel material.

FIG. 12C illustrates an enlarged view of a virtual image (Dig3) of the oral appliance. The virtual image is the merging of the additive Dig1 data and the subtractive data of Dig2 from, which the oral appliance can be produced that has regions along the sulcus (gumline) 63 where the medicament of the oral appliance will be loaded in a polymer gel material. The lower portion of the virtual oral appliance corresponds to and will contact portions of the tongue and hard palate as well as the soft palate 65 and 67 along each side of the oral cavity. It is from Dig 3 that the oral appliance can be manufactured.

In some embodiments of the applications described above, once the Dig3 virtual oral appliance is generated in whatever iteration, a virtual 3D image is sent to a stereolithography machine with at least two print heads to print or otherwise manufacture a treatment oral appliance. One print head of the stereolithography machine can print the Dig1 portion of Dig3 and the other can print the Dig2 portion of Dig3 simultaneously. Thus, in one step, an entire oral appliance can be monolithically manufactured according to the instruction provided by Dig3. In various embodiments, the print heads can use different chemical compositions. For example, in certain embodiments, the chemical composition for Dig1 portion can be stiffer in order to better hold onto the teeth and gums and be devoid of absorptive qualities while the Dig2 portion can be made of a different chemical composition which has absorptive qualities and can swell more easily. Useful chemical compositions comprise gels, hydrogels, polymer brushes and other swellable chemicals. These can be mixed uniformly with medicament, or alternately infused into Dig2 material after printing of Dig3.

Stereolithography printing allows the two different chemical compositions of Dig1 and Dig2 to combine simultaneously into one manufactured oral appliance, Dig3, without the use of adhesives or mechanical bonding. This is possible because the chemistry to allow the wedding of Dig1 and Dig2 has been worked out prior the manufacture and printing of Dig3. Additionally, since the hydrogel or other chemical used as a matrix for Dig2 is already loaded with the desired medicaments, the entire Dig3 oral appliance can be manufactured in only one sequence. There will be no soaks, dips, baths, sprays, or medicament rinses to load the appliance. However, it is recognized that the loading of the medicaments may require subsequent separate steps.

In some embodiments, the computer program uses an axis graph with physical properties on one axis and chemical properties on the other. These data are sent to print heads for manufacturing the device. The different print heads though holding different formulations will have chemical compatibility between them such that when printed simultaneously the formulations will seamlessly meld together as one piece thus allowing the Dig3 oral appliance to be fabricated at one time without the use of adhesives, glues or mechanical locking devises. In some embodiments, the medicament can be loaded and printed concurrently with the overall oral appliance.

With this digital model the oral appliance manufactured in accordance with Dig 3 is now ready to be placed in the oral cavity of the patient either in a wet or dry form. The hydrogel portion of the Dig3 oral appliance will expand if dry when wetted or can be already expanded if wet. In either case, the Dig2 portion of Dig3, which is the three-dimensional representation of the area to be treated will release its medicaments to the affected area in a three-dimensional manner once the oral appliance is inserted.

Once the oral appliances are printed or manufactured, the oral appliances are dried, packed and shipped to a dental professional who will deliver them to the patient with instructions for their use. The patient then performs a single use treatment and thereafter, after treatment, disposes of the oral appliance. A new tray is used for each treatment according to a prescribed regimen.

In some embodiments, oral appliances manufactured according to a three-dimensional model described herein can also be utilized to treat periodontal or gum diseases. In gum disease the initial form of the gums is often reddened and swollen. As such, the gums are larger than normal. As they heal, the gums shrink back to their normal, healed state size and become pink and firm. In order to generate a Dig2 system to treat gum diseases, Dig2 can be modified to consider the anticipated shrinking of the gums to ensure that the medicament layer is always in apposition to the diseased tissue. In some embodiments, if the gums are swollen by 2 mm, there can be a two week or 14 oral appliance treatment period. The first oral appliance for use on the first day can have an initial Dig2 thickness of 0.6 mm identified as Dig2A. The second oral appliance, identified as Dig2B, can have a thickness of 0.7 mm and can be used by the patient on the second day. On the third day, the patient can use Dig2C oral appliance, which can have a thickness of 0.8 mm. The process repeats itself until day 14 when the thickness of Dig2N can be 2 mm, thus fully accounting for the shrinkage of the gums and also allowing the medicaments to be always in direct contact with the gums. If this approach were not followed, the patient could end up with a situation where there would either be a gap between Dig2 and the gums or the gums would not shrink completely. This is a progressive system in which the Dig3 oral appliances are manufactured to account for daily and/or weekly changes to the desired therapy. Thus, in certain embodiments, the thickness of surface oral appliance is incrementally configured for treatment of a gum disease. Such a precise approach could not be accomplished with analog devices used in a conventional two-dimensional system or the patient can be reimaged and a whole new data set made with new trays reflecting real time healing.

In various embodiments, the oral appliance has a thickness of from about 0.06 inches to about 0.2 inches, a depth of at least about 1 mm to about 5 mm and a width of from about 1 mm to about 10 mm In certain embodiments, the thickness of surface of the oral appliance is incrementally configured for treatment of a gum disease.

Computer Implemented System

In various embodiments, the present disclosure provides a computer implemented method of making an oral appliance. The method comprises creating a digital record of a patient's oral cavity, the Base Image (BI), by obtaining a digital image of at least a portion of the teeth, and/or soft tissue of the oral cavity by using an imaging device. The Base Image is additively overlaid to create a first digital image, Dig1. Subsequently, a second digital image, Dig2, comprising at least a portion of the teeth and/or soft tissue of the oral cavity in need of treatment is subtractively generated. Thereafter, the first digital image, Dig1, and the second digital image, Dig2, are combined to form a third digital image, Dig3, of the oral cavity treatment area and the third digital image is then stored in the computer and used for manufacture.

In some embodiments, there is a computer implemented method of producing an oral appliance pre-loaded with at least one medicament using a computer, comprising: using the Base Image of the digital image of the patient's mouth, generating first digital data representing an overlay of at least a portion of the teeth and/or soft tissues areas of the oral cavity of a patient, generating second digital data by performing a digital segmentation of at least a portion of the teeth and/or soft tissues areas of the oral cavity to determine discrete regions of the oral cavity in need of treatment, combining the first digital data and the second digital data to form third digital data from which the oral appliance can be produced, wherein the third digital data comprises positions for at least one medicament to be placed at the discrete regions in the oral cavity in need of treatment.

In other embodiments, a computer-implemented method is provided for creating a treatment plan for delivering a medicament to at least a portion of the teeth and/or soft tissue areas inside the oral cavity. The computer-implemented method comprises generating a first digital data, Dig1, representing at least a portion or all of the teeth and/or soft tissues areas of the oral cavity of a patient from the Base Image. Subsequently, a second digital data, Dig2, is generated by performing via the computer a digital segmentation of at least a portion of the teeth and/or soft tissues areas of the oral cavity comprising discrete regions of the oral cavity in need of treatment. The first digital data, Dig1, and the second digital data, Dig2, are then combined via computer to form the third digital data, Dig3, from which the oral appliance can be produced, wherein the oral appliance has at least one medicament positioned at the discrete regions requiring treatment in the oral cavity.

In various embodiments, a computer-based system further comprises creating a virtual 3D image of the oral appliance indicating the discrete regions requiring treatment in the oral cavity; displaying on a display the virtual 3D image and performing interactive treatment plans including the selection of the at least one medicament Imaging devices utilized to generate the various digital data sets include, without limitations, a digital camera, X-ray device, hand-held 3-D scanner, laser scanner, computerized tomography (CT) scanner, magnetic resonance imaging (MRI) scanner, coordinate measuring machine, destructive scanner or ultrasound scanner, generating first digital data, Dig1, representing at least a portion of the teeth and/or soft tissues areas of the oral cavity of a patient based on an imaging device image (Base Image), generating second digital data, Dig2, by performing via the computer a digital segmentation of at least a portion of the teeth and/or soft tissues areas of the oral cavity comprising discrete regions of the oral cavity in need of treatment, combining via the computer the first digital data, Dig1, and the second digital data, Dig2, to form third digital data, Dig3, from which the oral appliance can be produced having at least one medicament positioned at the discrete regions requiring treatment in the oral cavity.

In other embodiments, the three-dimensional representation of the third digital data, Dig3, is stored in a format suitable for use by a manufacturer to produce the oral appliance pre-loaded with at least one medicament at areas targeted for treatment. A stereolithography apparatus comprising at least two print heads can be used to manufacture the oral appliances described in this disclosure. As discussed above, the first print head can be configured to deliver a first chemical composition according to the first digital data, Dig1, and the second print head can be configured to deliver a second chemical composition according to the second digital data, Dig2. The two combined merge and represent the image of the third digital data, Dig3. At least one of the chemical compositions includes a medicament while the other can be a polymer gel, hydrogel, brush polymer, another medicament or combinations thereof.

Referring to FIG. 16, it illustrates an embodiment of the computer-implemented system for producing an oral appliance. An input device or scanner 60 is used to scan the oral cavity of and thus generate a digital record of the patient's mouth (BI). The scanner can be an MRI scanner, a CT scanner, a PET scanner, a digital scanner, an X-Ray machine, or an intra-oral scanner, for example. In various embodiments, scanner 60 can scan the patient's teeth, soft tissue, or both to obtain a digital data set of the teeth and/or soft tissue areas inside the mouth from which is generated the Base Image. The digital data can be stored in a database, such as for example a computer that has a processor 62, which sends the digital data to its memory 64 and/or can display it in a virtual 3D image display 66 of processor 62. The database and/or processor can comprise an input device (e.g., keyboard, touch screen, voice activation, etc.) to allow a user to enter, display, edit, and/or transmit one or more images from Dig1, Dig2, Dig3. The processor 62 comprises logic to execute one or more instructions to carry instructions of the computer system (e.g., transmit instructions to the 3D printer, etc.). The logic for executing instructions may be encoded in one or more tangible media for execution by the processor 62. For example, the processor 62 may execute codes stored in a computer-readable medium such as memory 64. The computer-readable medium may be, for example, electronic (e.g., RAM (random access memory), ROM (read-only memory), EPROM (erasable programmable read-only memory)), magnetic, optical (e.g., CD (compact disc), DVD (digital video disc)), electromagnetic, semiconductor technology, or any other suitable medium. Based on memory 64, processor 62 can generate Dig2 and Dig3 and thereafter send a 3D image to the 3D printer 68 of a stereolithography apparatus.

In various embodiments, an authorized user can input, edit data and approve or prescribe a treatment plan based on the virtual 3D images displayed at the user interface of the computer processor 62 and/or another treating computer networked with computer processor 62. Although the components of the system of FIG. 16 are shown as separate, they may combine in one or more computer systems. Indeed, they may be one or more hardware, software, or hybrid components residing in (or distributed among) one or more local or remote computer systems. It also should be readily apparent that the components of the system as described herein may be merely logical constructs or routines that are implemented as physical components combined or further separated into a variety of different components, sharing different resources (including processing units, memory, clock devices, software routines, logic commands, etc.) as required for the particular implementation of the embodiments disclosed. Indeed, even a single general-purpose computer (or other processor-controlled device) executing a program stored on an article of manufacture (e.g., recording medium or other memory units) to produce the functionality referred to herein may be utilized to implement the illustrated embodiments. It also will be understood that the a plurality of computers or servers can be used to allow the system to be a network based system having a plurality of computers linked to each other over the network or Internet or the plurality of computers can be connected to each other to transmit, edit, and receive data via cloud computers.

The computer (e.g., memory, processor, storage component, etc.) may be accessed by authorized users. Authorized users may include at least one dentist or dental specialist, dental hygienist, oral surgeon, physician, surgeon, nurse, patient, and/or health care provider, manufacturer, etc.).

The user can interface with the computer via a user interface that may include one or more display devices (e.g., CRT, LCD, or other known displays) or other output devices (e.g., printer, etc.), and one or more input devices (e.g., keyboard, mouse, stylus, touch screen interface, or other known input mechanisms) for facilitating interaction of a user with the system via user interface. The user interface may be directly coupled to database or directly coupled to a network server system via the Internet or cloud computing. In accordance with one embodiment, one or more user interfaces are provided as part of (or in conjunction with) the illustrated systems to permit users to interact with the systems.

The user interface device may be implemented as a graphical user interface (GUI) containing a display or the like, or may be a link to other user input/output devices known in the art. Individual ones of a plurality of devices (e.g., network/stand-alone computers, personal digital assistants (PDAs), WebTV (or other Internet-only) terminals, set-top boxes, cellular/phones, screen phones, pagers, blackberry, smart phones, iPhone, iPad, table, peer/non-peer technologies, kiosks, or other known (wired or wireless) communication devices, etc.) may similarly be used to execute one or more computer programs (e.g., universal Internet browser programs, dedicated interface programs, etc.) to allow users to interface with the systems in the manner described. Database hardware and software can be developed for access by users through personal computers, mainframes, and other processor-based devices. Users may access and data stored locally on hard drives, CD-ROMs, stored on network storage devices through a local area network, or stored on remote database systems through one or more disparate network paths (e.g., the Internet).

The database can be stored in storage devices or systems (e.g., Random Access Memory (RAM), Read Only Memory (ROM), hard disk drive (HDD), floppy drive, zip drive, compact disk-ROM, DVD, bubble memory, flash drive, redundant array of independent disks (RAID), network accessible storage (NAS) systems, storage area network (SAN) systems, etc.), CAS (content addressed storage) may also be one or more memory devices embedded within a CPU, or shared with one or more of the other components, and may be deployed locally or remotely relative to one or more components interacting with the memory or one or more modules. The database may include data storage device, a collection component for collecting information from users or other computers into centralized database, a tracking component for tracking information received and entered, a search component to search information in the database or other databases, a receiving component to receive a specific query from a user interface, and an accessing component to access centralized database. Receiving component is programmed for receiving a specific query from one of a plurality of users. The database may also include a processing component for searching and processing received queries against data storage device containing a variety of information collected by collection device.

The disclosed system may, in some embodiments, be a computer network-based system. The computer network may take any wired/wireless form of known connective technology (e.g., corporate or individual LAN, enterprise WAN, intranet, Internet, Virtual Private Network (VPN), combinations of network systems, etc.) to allow a server to provide local/remote information and control data to/from other locations (e.g., other remote database servers, remote databases, network servers/user interfaces, etc.). In accordance with one embodiment, a network server may be serving one or more users over a collection of remote and disparate networks (e.g., Internet, intranet, VPN, cable, special high-speed ISDN lines, etc.). The network may comprise one or more interfaces (e.g., cards, adapters, ports) for receiving data, transmitting data to other network devices, and forwarding received data to internal components of the system (e.g., 3D printers, printer heads, etc.).

In accordance with one embodiment of the present application, the data may be downloaded in one or more textual/graphical formats (e.g., RTF, PDF, TIFF, JPEG, STL, XML, XDFL, TXT etc.), or set for alternative delivery to one or more specified locations (e.g., via e-mail, fax, regular mail, courier, etc.) in any desired format (e.g., print, storage on electronic media and/or computer readable storage media such as CD-ROM, etc.). The user may view viewing the search results and underlying documents at the user interface, which allows viewing of one or more documents on the same display.

In various embodiments, the computer software can create a 2D or 3D digital image of the patient's oral cavity to allow the treatment provider to review and discuss the proposed treatment with the patient. In another embodiment, the software can process the scanned data and provide the user/operator with useful data including tooth measurements (e.g. arch width, arch length, tooth size, angulations, sulcus size, etc.) to assist the user in fine-tuning the treatment plan. The computer can then provide the operator with options in staging the treatment plan from one stage to another stage, or it can completely generate all stages ranging from the initial to final desired stage. The staging can be done automatically.

FIG. 17 is a flow chart illustrating the logic steps followed by processor 62 of FIG. 16. The first step 70 comprises generating a Base Image (BI) of at least a portion of the teeth and/or soft tissues by using an imaging device. In step 72, the BI is stored in the memory of the processor. In step 74, a first data set (Dig1) is generated by the computer additively layering over the BI of at least a portion of the teeth and/or soft tissues. The Dig1 is stored.

In step 76, a second data set (Dig2) is generated by digitally segmenting at least a portion of the teeth and/or soft tissues from the Base Image. Thereafter, in step 78, the processor can decide if all discrete regions of the oral cavity in need of treatment have been identified or if they have not been, then the digital segmentation step will occur again. Dig2 will also be checked for accuracy.

If all the desired discrete regions have been identified, then in step 80, the processor stores the data, which includes the discrete regions in need of treatment as a separate set corresponding to Dig2. The first and second data sets are combined in step 82 to generate a third data set corresponding to Dig3. The third data set is stored in step 84 and then sent to a 3D printer in step 86.

FIG. 18 is a flow chart illustrating an embodiment of the computer-implemented system for treating a patient utilizing an oral appliance produced according to this disclosure. As described above, the oral cavity of the patient is scanned, and a mold may be generated in step 90. Based on the information gathered in step 90, Dig1 is generated in step 92. Subsequently, a second digital data set is generated via digital segmentation and Dig2 is obtained in step 94. As discussed above, Dig1 and Dig2 digital data sets are combined in step 96 to generate Dig3, which provides the logic and instructions to a 3D printer to print Dig3 in step 98. The oral appliances produced by a stereolithography are then rinsed and loaded with medicaments in step 100. The oral appliances are then dried and packed in step 102 and shipped to a dental professional in step 104. Alternatively, there may be no rinse step or medicament loading as the stereolithography machine may have the medicaments already loaded in its print head. In step 106, the patient receives the oral appliances and inserts them as required in a daily process in step 108. After the treatment period of step 110 is completed, each oral appliance is removed and discarded, daily, in step 112. Alternatively, if a diagnosis needs to be made or biologic markers need to be assessed for healing, the oral appliances can be sent to a laboratory for testing and then the oral appliances disposed of by the laboratory.

In various embodiments, the present disclosure provides a computer implemented method of making a system for treating inflamed gum tissue surrounding at least one tooth inside an oral cavity. The method comprises obtaining a first set of digital data representing a first layer overlying and conforming to a Base Image (BI), which is a digitally stored topography of an oral cavity having inflamed gum tissue surrounding the at least one tooth, the Base Image produced by an imaging device to form a first digital image (Dig1); obtaining a second set of digital data representing a second virtual layer circumscribed by the at least one treatment surface area and including a volume extending into said topography, the second set defining at least one surface area of inflamed gum tissue including discrete regions of the oral cavity of a patient from the Base Image to form a second digital image (Dig2), automatically and/or with the aid of an operator interaction; combining the first digital image (Dig1) with the second digital image (Dig2) to obtain a third digital image (Dig3) from the first and second digital data sets, the third digital image representing the first set of digital data with said second set of digital data added onto the surface and being configured to direct a 3D printer; creating a virtual 3D oral appliance containing the at least one medicament or at the least an inflamed gum tissue for grafting from the third digital image (Dig3); displaying the virtual 3D oral appliance on a computer screen using a user interface; performing interactive treatment plans including the selection of the at least one medicament or the at least an inflamed gum tissue for disposing at target areas of the patient's oral cavity; and directing the 3D printer to produce the oral disposable appliance containing the at least one medicament.

In other embodiments a computer implemented method of producing a disposable oral appliance pre-loaded with at least one medicament for treating inflamed gum tissue surrounding at least one tooth of a patient using a computer is provided. The method comprises generating a first digital data representing at least a portion of the teeth and/or inflamed gum tissue areas of the oral cavity of the patient, the first digital data generated from an imaging device having a base image of the oral cavity; generating a second digital data from the base image by performing a digital segmentation of at least a portion of the at least one tooth and/or inflamed gum tissue areas of the oral cavity to determine discrete regions of the oral cavity that are in need of treatment; combining the first digital data (Dig1) and the second digital data (Dig2) to form third digital data (Dig3) from which the oral appliance can be produced, wherein the third digital data comprises positions for at least one porous agent to be placed at the discrete regions of inflamed gum tissue in the oral cavity in need of treatment. The computer implemented method further comprises creating a virtual 3D image of the disposable oral appliance indicating the discrete regions not requiring treatment in the oral cavity; displaying on a display the virtual 3D image; and performing interactive treatment plans including the selection of the at least one medicament.

In many aspects, the present disclosure also provides a method of treating inflamed gum tissue surrounding a tooth inside an oral cavity. The method of treating comprises placing a first disposable oral appliance over at least a portion of a tooth and inflamed gum tissue, the first oral appliance having a shell having cavities and material containing a medicament, the shell configured to collect crevicular/sulcular fluid, the first oral appliance formed to fit tightly over the inflamed gum tissue in a first inflamed gum arrangement. The method of treating also includes removing the first disposable oral appliance after an effective amount of crevicular/sulcular fluid was collected; placing a successive disposable oral appliance over at least the portion of a previously treated tooth, the treated tooth having a progressively less inflamed gum tissue relative to the first inflamed gum arrangement to obtain a successive less inflamed gum arrangement; and removing the successive disposable oral appliance after an effective amount of crevicular/sulcular fluid was collected; repeating the previous steps until a healthy gum tissue is obtained.

Having now generally described the invention, the same may be more readily understood through reference to the following examples, which are provided by way of illustration and are not intended to limit the present invention unless specified.

This Example is contemplated.

Example

Top Down Treatment

It has not been appreciated that periodontal disease constantly replenishes and nourishes the base of the pocket from the microbiome above it. The disease starts from the coronal portion of the gums (the "top" of the gums), and over time, makes its way apically subgingivally ("down" the gums). The disease progresses "top-down," forming a gradient of microbiota down the length of the pocket. Coronally, towards the top, exist more aerobic bacteria. Apically, towards the base of the pocket, exist more anaerobic bacteria. By treating the disease in its initial pattern of progression, the gradient will shrink, iteratively narrowing the gradient until the pathological anaerobic bacteria are inhibited. Additionally, for the chemical therapies, such as Arestin®, which contains minocycline microspheres, and PerioChip®, which is a biodegradable chip containing chlorhexidine, the materials introduced into the pocket are foreign bodies which need to be absorbed and resorbed, creating a foreign body reaction which results in even more inflammation, thus aggravating the situation. This bottom up theory of treatment often does not work. What is introduced in the current application is a top/down method for treating periodontal disease. This method allows patients to treat periodontal disease effectively at home, in adjunct with professional services, which has not been available before.

Many current treatment modalities are either surface in nature (only reaching the first 3-4 mm of free gingiva) or attack the base of the pocket. What is introduced in the current application is a treatment of periodontal disease the way it has always progressed: treat periodontal disease from the top, down. And since periodontal disease is a chronic inflammatory disease, treat it like other chronic inflammatory diseases such as Rheumatoid Arthritis—chronically, in a sustained manner.

The top down method for treating periodontal disease mimics the periodontal disease model by first attacking the bacterial infection present using antimicrobials in a daily, sustained regimen, preferably using the oral appliance described herein. The oral appliance or tray contains porous material, hydrogel, which is impregnated with antiseptic, chlorhexidine, which is released for a sustained period of time until that infection abates and is brought under greater control. The oral appliance containing the hydrogel serves multiple purposes. It holds the medicament in place without dilution by saliva or contamination by oral liquids, and it keeps medicament at the top portion of the pocket by encapsulating the entrance to the pocket. As the hydrogel is squeezed, the medicament diffuses into the top portion of the pocket. The oral appliance design, characterized by the hydrogel placement over the gingival crevice, is akin to a capping device, sealing off the opening to the pocket from outside contamination by saliva and other liquids, and forcing the hydrogel-laden medicament in the pocket entrance. By encapsulating the gingival crevice, which is the entrance to the periodontal pocket, the oral appliance assures that the captured fluids, which are those fluids coating and surrounding the teeth and soft tissues when the tray is inserted, are pushed away from the crevice entrance and kept away by the encapsulating hydrogel over the crevice. Further, as the hydrogel is emptied of medicament, GCFs are wicked up and absorbed by the hydrogel in a fluid exchange, removing this contaminated exudate from the infected periodontium. GCFs are exudate fluids comprised of bacteria, dead cellular structures, interstitial fluids, inflammatory factors, etc. The greater the degree of inflammation due to the periodontal disease, the greater the rate of flow of the GCF. Therefore, removing the GCF from the pocket creates space for the medicament to occupy. This will result in decreased inflammation and thus decreased GCF flow. As the gingiva at the top portion of the pocket begins to respond to the anti-microbials, the surface inflammation will decrease, and the pocket will also shrink in depth as some healing and regenerating processes occur. Just as periodontal disease progresses incrementally, the healing process is also incremental. First, the pathologic bacteria are reduced, then using appropriate drugs the inflammatory response is reduced and then healing will initiate will some fibers reforming and attaching the teeth to the gums and/or bone and bone regeneration will occur. This continuum of healing is a prolonged process which the top down system seeks to mimic and encourage. Finally, when the climate for the tissue is appropriate and sufficiently healed, probiotics can be introduced to recolonize the area with good bacteria when their success at recolonization is assured.

Once the antimicrobial treatment regimen has adequately reduced the pathologic microbiome, other avenues of treatment can be initiated to combat the other aspects of the periodontal disease sequence. For instance, H2 blockers, or other medicaments used in chronic stomach ulcers can be used to decrease the inflammatory response. Other treatment modalities such as SRP, dental cleaning, brushes, floss, waterpiks, toothpastes, rinses, etc. will serve several purposes in addition to getting the patient off the antimicrobials and letting the good bacteria try to repopulate the microbiome. These other medicaments will assist the host in the healing process so the body can begin to take over a now more manageable inflammatory condition. Now it is recognized that each phase of treatment may involve a "cocktail regimen" of combining different drugs that may work synergistically to further attack the periodontal disease (PD) and simultaneously encourage healing. However, in all instances, the line of attack is to work from the top down in a systematic fashion over time to gradually and increasingly project medicaments ever deeper into the healing and shrinking pockets.

In order to monitor the sequencing and timing of medicaments, a regimen of criteria will be monitored to assist the health care practitioner in evaluating the healing status of the patient. When the patient is first evaluated, records of the patient's clinical data such as pocket depths, bleeding analysis, photos of the texture of the gingiva showing swelling and plaque accumulations and attachment levels are all recorded. Further, other tests such as bacterial assays can be measured. At periodic times after treatment is initiated, a reanalysis is performed and compared with the original. As the architecture of the gums improves and the texture and the surface real estate of the gums changes, new imaging of the mouth will be performed in order to have new trays made with altered placement of the hydrogel in order to better cap off the gingival crevice which may move over time. The capping of the crevice is essential to the proper infusion of the medicaments into the pocket. Also, based on improvements in the data, the pharmacologic treatment may be altered to initiate different avenues of attack against the inflammation. For instance, if the bacterial profile has improved, then anti-inflammatory medicaments may be used to assist the body in healing. The oral appliance architecture and the medicament profile will change according to all this monitored data. It is similar to managing a systemic disease by following a patient's changing blood test profile. Other patient data, such as allergies, can also be used to better individualize pharmacologic treatments to each individuals' periodontal profile.

This healing process will also serve another purpose and that is that the pathogenic microbiome first described above with aerobic bacteria predominately at the top and anerobic bacteria predominately at the bottom, with a gradient mixture in between, will now get compressed with the result that the virulence of the infection will decrease overall. In this improved micro-environment, O2 will be able to penetrate to a greater degree further increasing healing by killing the anaerobes. The exudate quality and quantity will also improve by being less toxic and less copious. All of this is an exact mirrored reversal of the original PD process.

Near the end of the treatment phase, probiotics can be introduced to subgingivally flood a more receptive microbiome with good bacteria, in order to positively repopulate the system.

The top down method of treatment treats periodontal disease in a sequenced fashion to maximize the body's healing potential. It does not seek to treat the bottom first and work its way up to the top as with the older methods of treatment.

Further, it will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An oral appliance for delivering a medicament to an inflamed tissue of an oral cavity, the oral appliance having an interior surface configured to contour at least a portion of teeth and/or soft tissue areas of the oral cavity, the interior surface of the oral appliance having a medicament disposed in a porous material at a region of the interior surface of the oral appliance, the porous material having a projection configured to contact the soft tissue of the oral cavity including a top portion of the inflamed tissue of a gingival and/or periodontal pocket of the oral cavity when the oral appliance is worn to cause delivery of the medicament to at least the top portion of the inflamed tissue, wherein the oral appliance, when worn, is configured to compress the porous material against the gingival and/or periodontal pocket and form a seal at an entrance of the gingival and/or periodontal pocket so as to allow the projection which is sized and shaped to extend into the gingival and/or periodontal pocket to prevent oral fluid from entering therein and to allow a gap to form between the projection of the porous material and the inflamed tissue within the gingival and/or periodontal pocket so as to allow delivery of the medicament from the projection inside the seal to the inflamed tissue within the gingival and/or periodontal pocket and also allow wicking of oral fluid into the projection, and wherein the porous material has an upper surface having a low concentration of the medicament, a middle surface having a high concentration of the medicament and a lower surface having a low concentration of the medicament such that when the oral appliance is worn, the middle surface having the high concentration of medicament is located immediately adjacent to the gingival and/or periodontal pocket and the upper surface and the lower surface having the low concentration of medicament are located away from the entrance of the periodontal pocket.

2. The oral appliance of claim 1, wherein the porous material is sized to be greater than the height, width, and length of the entrance of the gingival and/or periodontal pocket to cause the medicament to be released inside the seal within the gingival and/or periodontal pocket compared to outside the periodontal pocket.

3. The oral appliance of claim 1, wherein the porous material that forms the seal at the entrance of the gingival and/or periodontal pocket has a higher concentration of the medicament as compared to porous material opposite and outside the seal.

4. The oral appliance of claim 1, wherein the inflamed tissue comprises periodontal disease.

5. The oral appliance of claim 1, wherein the porous material absorbs crevicular, sulcular fluid, exudate or a combination thereof from the inflamed tissue.

6. The oral appliance of claim 1, wherein the porous material is a hydrogel.

7. The oral appliance of claim 1, wherein the oral appliance comprises an exterior surface that is non-porous.

8. The oral appliance of claim 1, wherein the medicament comprises an antimicrobial agent, an anti-inflammatory agent, an antiseptic agent, a probiotic, an immunologic agent, an astringent agent, or a mixture thereof.

9. The oral appliance of claim 8, wherein the probiotic comprises a bacterium which comprises *L. brevis, B. lactis, B. longum, L. acidophilus, L. reuteri, L. salivarius, L. sporogens, S. oralis, S. uberis, S. rattus, L. rhamanosus* or a mixture thereof.

10. The oral appliance of claim 8, wherein the medicament is free of hydrogen peroxide.

11. The oral appliance of claim 8, wherein the antiseptic is chlorhexidine.

12. The oral appliance of claim 1, wherein the oral appliance is disposable.

13. The oral appliance of claim 1, wherein the medicament is chlorhexidine, which is disposed in a porous material comprising a polymer.

14. A system for delivering a medicament to an inflamed tissue of an oral cavity, the system comprising a first set of oral appliances, each of the first set of oral appliances having an interior surface configured to contour at least a portion of the teeth and/or soft tissue areas of the oral cavity, the interior surface of each of the first set of oral appliances having a medicament disposed in a porous material at a region of the interior surface of each of the first set of oral appliances, the porous material having a projection configured to contact the soft tissue of the oral cavity including a top portion of the inflamed tissue of a gingival and/or periodontal pocket of the oral cavity when the oral appliance is worn to cause delivery of the medicament to at least the top portion of the inflamed tissue, wherein the oral appliance, when worn, is configured to compress the porous material against the gingival and/or periodontal pocket and form a seal at an entrance of the gingival and/or periodontal pocket so as to allow the projection which is sized and shaped to extend into the gingival and/or periodontal pocket to prevent oral fluid from entering therein and to allow a gap to form between the projection of the porous material and the inflamed tissue within the gingival and/or periodontal pocket so as to allow delivery of the medicament inside the seal to the inflamed tissue within the gingival and/or periodontal pocket; and a second set of oral appliances, each of the second set of oral appliances having an interior surface configured to contour at least the portion of teeth and/or soft tissue areas of the oral cavity, the interior surface of each of the second set of oral appliances having a medicament disposed in a porous material at a region of the interior surface of each of the second set of oral appliances, the porous material having a projection configured to contact the soft tissue of the oral cavity including a middle portion of the inflamed tissue of a gingival and/or periodontal pocket of the oral cavity so as to allow the projection which is sized and shaped to extend into the gingival and/or periodontal pocket when the oral appliance is worn to cause delivery of the medicament from the projection to at least the middle portion of the inflamed tissue and also allow wicking of oral fluid into the projection, and wherein the porous material has an upper surface having a low concentration of the medicament, a middle surface having a high concentration of the medicament and a lower surface having a low concentration of the medicament such that when the oral appliance is worn, the middle surface having the high concentration of medicament is located immediately adjacent to the gingival and/or periodontal pocket and the upper surface and the lower surface having the low concentration of medicament are located away from the entrance of the periodontal pocket.

15. The system of claim 14, wherein the system further comprises a third set of oral appliances, each of the third set of oral appliances having an interior surface configured to contour at least the portion of teeth and/or soft tissue areas of the oral cavity, the interior surface of each of the third set of oral appliances having a medicament disposed at a region of the interior surface of each of the third set of oral appliances, the medicament configured to deliver to a bottom portion of the inflamed tissue inside the oral cavity when the oral appliance is worn to cause delivery of the medicament to at least the bottom portion of the inflamed tissue.

16. The system of claim 15, wherein the system further comprises a fourth set of oral appliances, each of the fourth set of oral appliances having an interior surface configured to contour at least the portion of teeth and/or soft tissue areas inside the oral cavity, the interior surface of each of the fourth set of oral appliances having a medicament disposed at a region of the interior surface of each of the fourth set of oral appliances, wherein the medicament is a probiotic.

17. The system of claim 14, wherein the medicament comprises an antimicrobial agent, an anti-inflammatory agent, an antiseptic agent, a probiotic, an immunologic agent, an astringent agent, or a mixture thereof.

* * * * *